(12) United States Patent
Sato et al.

(10) Patent No.: US 11,406,788 B2
(45) Date of Patent: Aug. 9, 2022

(54) INFORMATION PROCESSING APPARATUS AND METHOD

(71) Applicant: SONY CORPORATION, Tokyo (JP)

(72) Inventors: Naoyuki Sato, Tokyo (JP); Atsushi Iwamura, Tokyo (JP); Ryoji Miyazaki, Chiba (JP); Shigeru Sugaya, Kanagawa (JP); Masakazu Ukita, Kanagawa (JP); Yoshiyuki Kobayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 226 days.

(21) Appl. No.: 16/635,237

(22) PCT Filed: Jul. 26, 2018

(86) PCT No.: PCT/JP2018/028031
§ 371 (c)(1),
(2) Date: Jan. 30, 2020

(87) PCT Pub. No.: WO2019/031257
PCT Pub. Date: Feb. 14, 2019

(65) Prior Publication Data
US 2020/0368488 A1    Nov. 26, 2020

(30) Foreign Application Priority Data

Aug. 8, 2017   (JP) .............................. JP2017-153128

(51) Int. Cl.
*A61B 5/16* (2006.01)
*A61M 21/02* (2006.01)
(Continued)

(52) U.S. Cl.
CPC ............. *A61M 21/00* (2013.01); *A61B 5/165* (2013.01); *A61B 5/486* (2013.01); *A61B 5/4812* (2013.01);
(Continued)

(58) Field of Classification Search
CPC ............ A61M 21/00–02; A61B 5/165; A61B 5/4806–4815; G16H 20/70; G16H 50/30; G06F 2203/011
See application file for complete search history.

(56) References Cited

U.S. PATENT DOCUMENTS

2001/0049471 A1   12/2001   Suzuki et al.
2006/0142968 A1   6/2006    Han et al.
(Continued)

FOREIGN PATENT DOCUMENTS

JP   2001-344352 A   12/2001
JP   2006-246437 A   9/2006
(Continued)

OTHER PUBLICATIONS

International Search Report and Written Opinion of PCT Application No. PCT/JP2018/028031, dated Oct. 9, 2018, 10 pages of ISRWO.

*Primary Examiner* — Thaddeus B Cox
(74) *Attorney, Agent, or Firm* — Chip Law Group

(57) ABSTRACT

The present technology relates to information processing apparatus and method, and a program that make a stress level controllable depending on circumstances. A stress level measuring unit measures a stress level of a user on the basis of a result of detection by various types of sensors included in an input unit. A stress factor specifying unit specifies a factor causing an increase or decrease in the stress level on the basis of an action of the user in a period in which the stress level is increased or decreased. The present technology is applicable to a stress control system, for example.

18 Claims, 41 Drawing Sheets

(51) Int. Cl.
   *A61M 21/00*      (2006.01)
   *A61B 5/00*       (2006.01)
(52) U.S. Cl.
   CPC .............. *A61B 5/741* (2013.01); *A61B 5/742* (2013.01); *A61M 21/02* (2013.01); *A61M 2021/005* (2013.01); *A61M 2021/0027* (2013.01); *A61M 2021/0083* (2013.01)

(56) References Cited

U.S. PATENT DOCUMENTS

| | | | | |
|---|---|---|---|---|
| 2009/0264711 | A1* | 10/2009 | Schuler | A61B 5/16 600/300 |
| 2012/0130196 | A1* | 5/2012 | Jain | A61B 5/681 600/300 |
| 2014/0085101 | A1* | 3/2014 | Rahman | G16H 40/67 340/870.01 |
| 2015/0112158 | A1* | 4/2015 | He | A61B 5/7278 600/301 |
| 2015/0342511 | A1* | 12/2015 | Goldberg | A61B 5/165 434/236 |
| 2016/0157776 | A1* | 6/2016 | Mestha | A61B 5/02438 600/479 |
| 2016/0354027 | A1* | 12/2016 | Benson | A61B 5/0533 |
| 2017/0209053 | A1* | 7/2017 | Pantelopoulos | A61B 5/02125 |
| 2017/0293727 | A1* | 10/2017 | Klaassen | A61B 5/6898 |
| 2018/0164108 | A1* | 6/2018 | Rahal-Arabi | G01C 21/3484 |
| 2018/0196922 | A1* | 7/2018 | Abuelsaad | G16H 10/60 |

FOREIGN PATENT DOCUMENTS

| | | |
|---|---|---|
| JP | 2012-120206 A | 6/2012 |
| JP | 2012-249797 A | 12/2012 |
| JP | 2015-160050 A | 9/2015 |
| JP | 2016-209404 A | 12/2016 |

\* cited by examiner

FIG. 6

| TYPES | DATA TO BE USED | OBTAINING METHOD |
|---|---|---|
| ONE-DIMENSIONAL DISCRETE QUANTITY | TRANSPORTATION MEANS (STANDSTILL, WALKING, TRAIN, ...) | ANALYZING VIBRATIONAL PATTERN BY ACCELERATION SENSOR |
| | APPLICATION IN USE | OBTAINING FOREGROUND APPLICATION |
| | MUSIC BEING LISTENED TO | OBTAINING SONG BEING PLAYED ESTIMATING SONG FROM SOUNDS COLLECTED BY MICROPHONE |
| | TV PROGRAM BEING VIEWED | ESTIMATING PROGRAM FROM SOUNDS COLLECTED BY MICROPHONE |
| | COMPANION | POSITION INFORMATION OF USERS BY GPS IS MUTUALLY CLOSE BOTH USERS ARE WITHIN SCANNING RANGE OF BLUETOOTH BOTH USERS ARE WITHIN WI-FI SCANNING RANGE |
| | TIME ZONES (MORNING, AFTERNOON, EVENING, ...) | BUILT-IN CLOCK |
| | SEASONS | BUILT-IN CLOCK |
| ONE-DIMENSIONAL CONTINUOUS QUANTITY | NOISE LEVEL | OBTAINING SOUND PRESSURE BY MICROPHONE |
| | BRIGHTNESS LEVEL | OBTAINING BRIGHTNESS BY ILLUMINATION SENSOR |
| | EXERCISE INTENSITY | ANALYZING VIBRATIONAL PATTERN BY ACCELERATION SENSOR |
| POSITION INFORMATION | CURRENT LOCATION | STORING HISTORY BY GPS STORING ENTRY/EXIT HISTORY BY MAP APPLICATION |

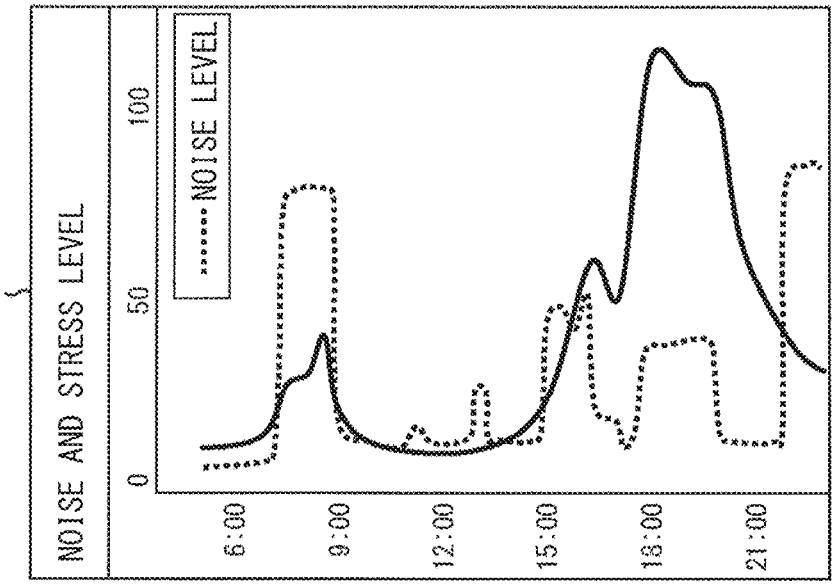

FIG. 25

| | STRESS LEVEL | REASON | PRESENTATION OF STRESS-RELIEVING ACT |
|---|---|---|---|
| WAKE UP AT 8:00 A.M. | HIGH | USER WANTED TO SLEEP A LITTLE LONGER, BUT WAS WOKEN UP BY FAMILY | • DIFFUSE FAVORITE AROMA<br>• PLAY FAVORITE MUSIC OR SHOW FAVORITE TELEVISION PROGRAM |
| MORNING ACTION | HIGH | USER WANTS TO GO SHOPPING BUT HAS TO CLEAN UP | • REFRESH BY TAKING A DOG WALK<br>• GET INVOLVED IN CLEANING BY PLAYING MUSIC SUITABLE FOR SIMPLE TASK<br>• SUGGEST DRINKING COFFEE AFTER CLEANING |
| LUNCH | HIGH | USER IS GOING TO LUNCH WITH RELATIVES WHO DO NOT GET ALONG WITH USER FOR SOCIAL REASON | • PRESENT DISH THAT IS FAVORITE AND ALLOWS STRESS TO BE RELIEVED<br>• IF FRIEND WHO GET ALONG WITH USER IS IN NEIGHBORHOOD, PRESENT DRINKING COFFEE WITH FRIEND AFTER LUNCH<br>• PRESENT WALKING HOME AND MAKING STOP AT RELAXING PLACE |
| AFTERNOON ACTION | HIGH | USER WANTS TO HAVE NAP, BUT IS ASKED TO GO SHOPPING | • SUGGEST NAPPING<br>• PLAY FAVORITE MUSIC DURING TRAVELING FOR SHOPPING<br>• SUGGEST GOING TO SHOP THAT IS EVEN A LITTLE ENJOYABLE FOR USER<br>• SUGGEST BUYING SWEETS AND COFFEE FOR BREAK AFTER SHOPPING |
| NIGHTTIME ACTION | HIGH | USER WANTS TO WATCH FAVORITE TELEVISION PROGRAM, BUT CHILD TAKES OVER TELEVISION | • DISPLAY CONTENTS THAT ARE ENJOYABLE FOR CHILDREN AND ADULTS TO FAMILY<br>• SUGGEST GAME OR THE LIKE THAT IS ENJOYABLE FOR FAMILY |

FIG. 26

| | STRESS LEVEL | REASON | PRESENTATION OF STRESS-RELIEVING ACT | DOES INPUT STRESS LEVEL EXCEED THRESHOLD VALUE? | HOW TO OBTAIN USER'S SITUATION | AUTOMATIC EXECUTION OF STRESS-RELIEVING ACT | GUIDANCE ON THE STRESS-RELIEVING ACT |
|---|---|---|---|---|---|---|---|
| WAKE UP AT 6:00 A.M. | HIGH | SLEEP DURATION WAS SHORT BECAUSE OF WORK | • DIFFUSE FAVORITE AROMA | PULSE METER OF SMART WATCH DETECTS THAT STRESS IS HIGHER THAN USUAL | RECOGNIZE WHERE USER IS BY CAMERA AT HOME | IT IS RECOGNIZED THAT USER IS IN BEDROOM, SO AUTOMATICALLY EXECUTE STRESS-RELIEVING ACT IN BEDROOM ON BASIS OF PAST DATA | |
| | | | • PLAY FAVORITE MUSIC | SAME AS ABOVE | SAME AS ABOVE | IT IS RECOGNIZED THAT USER IS IN LIVING ROOM, SO AUTOMATICALLY EXECUTE STRESS-RELIEVING ACT IN LIVING ROOM ON BASIS OF PAST DATA | |
| | | | • SHOW FAVORITE TELEVISION PROGRAM | SAME AS ABOVE | SAME AS ABOVE | SAME AS ABOVE | |
| COMMUTE | HIGH | TRAIN IS MORE CROWDED THAN USUAL DUE TO TRAIN DELAY | • PRESENT FAVORITE TELEVISION PROGRAM ON SMARTPHONE | SAME AS ABOVE | RECOGNIZE THAT USER IS RIDING ON TRAIN BY GPS OR ACCELEROMETER OF SMARTPHONE/RECOGNIZE THAT TRAIN IS CROWDED FROM INFORMATION OF TRAIN COMPANY. SMARTPHONE IS ALLOWED TO OPERATE SMARTPHONE BY OPENED SCREEN OF SMARTPHONE | | LIST STRESS-RELIEVING ACTS ON SMARTPHONE FROM PAST DATA/NOTIFY USER THAT FAVORITE TELEVISION PROGRAM CAUSING GREATEST EFFECT IS ALLOWED TO BE WATCHED ON SMARTPHONE |
| | | | • PRESENT WALKING TO OFFICE WHILE RELIEVING STRESS BY LIGHT EXERCISE, BECAUSE IT IS FOUND THAT IT DOES NOT TAKE LONG EVEN IF USER WALKS TO OFFICE | SAME AS ABOVE | RECOGNIZE THAT USER IS RIDING ON TRAIN BY GPS OR ACCELEROMETER OF SMARTPHONE/RECOGNIZE THAT TRAIN IS CROWDED FROM INFORMATION OF TRAIN COMPANY/IT IS POSSIBLE TO WALK TO OFFICE FROM POSITION INFORMATION AND SCHEDULE TABLE | | PAST DATA INDICATES THAT WALKING DECREASES STRESS, SO NOTIFY USER BY SMARTPHONE TO WALK TO OFFICE |

FIG. 27

| STRESS LEVEL | REASON | PRESENTATION OF STRESS-RELIEVING ACT | DOES INPUT STRESS LEVEL EXCEED THRESHOLD VALUE? | HOW TO OBTAIN USER'S SITUATION | AUTOMATIC EXECUTION OF STRESS-RELIEVING ACT | GUIDANCE ON THE STRESS-RELIEVING ACT |
|---|---|---|---|---|---|---|
| WORK IN MORNING / HIGH | WORKS CLOSE TO DEAD-LINES | • GET INVOLVED IN WORK WHILE PLAYING FAVORITE MUSIC | PULSE METER OF SMART WATCH DETECTS THAT STRESS IS HIGHER THAN USUAL | RECOGNIZE THAT NO ONE IS AROUND BY MICROPHONE OF SMARTPHONE RECOGNIZE THAT WORKS ARE PILED UP FROM SCHEDULE TABLE | IT IS KNOWN FROM PAST DATA THAT IT IS POSSIBLE TO CONCENTRATE WHEN FAVORITE MUSIC IS PLAYED, SO PLAY FAVORITE MUSIC | |
| | ARE PILED UP | • PRESENT ASKING QUESTION ABOUT WORK TO SOMEONE WHO GET ALONG WITH USER | SAME AS ABOVE | RECOGNIZE THAT PC IS OPEN, BUT WRITING ETC. IS NOT PERFORMED FREQUENTLY OR BROWSER RESEARCH IS CONDUCTED | | SUGGESTION FOR ASKING QUESTION TO FRIEND WHO GETS ALONG WITH USER IS DISPLAYED ON PC |
| | | • PRESENT DELIVERING SUBMISSION USING STAIRS | SAME AS ABOVE | RECOGNIZE THAT THERE IS SUBMISSION FROM SCHEDULE TABLE | | IT IS KNOWN FROM PAST DATA THAT TAKING EXERCISE DECREASES STRESS, SO SUGGESTION FOR DELIVERING SUBMISSION ON FOOT IS DISPLAYED ON SMART WATCH UPON GETTING UP FROM SEAT |

FIG. 28

| | Stress Level | Reason | Presentation of Stress-Relieving Act | Does Input Stress Level Exceed Threshold Value? | How to Obtain User's Situation | Automatic Execution of Stress-Relieving Act | Guidance on the Stress-Relieving Act |
|---|---|---|---|---|---|---|---|
| LUNCH | HIGH | LUNCH WITH TROUBLESOME CLIENT | • PRESENT DISH THAT IS FAVORITE AND ALLOWS STRESS TO BE RELIEVED | INCREASE IN STRESS IS PREDICTED FROM SCHEDULE TABLE | RECOGNIZE MEETING WITH TROUBLESOME CLIENT FROM SCHEDULE TABLE (RECOGNIZE TROUBLESOME CLIENT FROM PAST DATA) | | IT IS KNOWN THAT EATING FAVORITE DISH DECREASES STRESS, SO CONTACT RESTAURANT REGARDING FAVORITE MENU, AND NOTIFY USER |
| | | | • IF FRIEND WHO GETS ALONG WITH USER IS IN NEIGHBORHOOD, PRESENT DRINKING COFFEE WITH FRIEND AFTER LUNCH | PULSE METER OF SMART WATCH DETECTS THAT STRESS IS HIGHER THAN USUAL | RECOGNIZE THAT FRIEND IS IN NEIGHBORHOOD FROM GPS OF SMARTPHONE AND POSITION INFORMATION OF FRIEND | | IT IS KNOWN FROM PAST DATA THAT SPEAKING WITH FRIEND DECREASES STRESS SO IF USER HAS SPARE TIME IN SCHEDULE TABLE, NOTIFY USER BY SMARTPHONE UPON LEAVING RESTAURANT |
| | | | • PRESENT WALKING TO HOME AND MAKING STOP AT RELAXING PLACE | SAME AS ABOVE | RECOGNIZE POSITION INFORMATION BY GPS OF SMARTPHONE | | IF USER HAS SPARE TIME IN SCHEDULE TABLE, SUGGESTION FOR GOING TO RELAXING PLACE IS DISPLAYED ON SMARTPHONE |
| | | | • SUGGEST NAPPING | SAME AS ABOVE | RECOGNIZE POSITION INFORMATION BY GPS OF SMARTPHONE | | IF USER HAS SPARE TIME IN SCHEDULE TABLE, RECOMMEND HAVING NAP |

FIG. 29

| | STRESS LEVEL | REASON | PRESENTATION OF STRESS-RELIEVING ACT | DOES INPUT STRESS LEVEL EXCEED THRESHOLD VALUE? | HOW TO OBTAIN USER'S SITUATION | AUTOMATIC EXECUTION OF STRESS-RELIEVING ACT | GUIDANCE ON THE STRESS-RELIEVING ACT |
|---|---|---|---|---|---|---|---|
| WORK IN AFTER-NOON | HIGH | MEETING WITH TROUBLE-SOME SUPERIOR | • DIFFUSE FAVORITE AROMA BEFORE MEETING | INCREASE IN STRESS IS PREDICTED FROM SCHEDULE TABLE | RECOGNIZE FROM SCHEDULE TABLE THAT THERE IS MEETING WITH TROUBLESOME SUPERIOR (RECOGNIZE TROUBLESOME SUPERIOR FROM PAST DATA) / RECOGNIZE POSITION BY GPS OF SMARTPHONE | WHEN IT IS RECOGNIZED THAT NO OTHER PERSON IS AROUND BY MICROPHONE ETC., DIFFUSE FAVORITE AROMA | |
| | | | • HAVE MEETING WITH COLLEAGUE WHO GETS ALONG WITH USER BEFORE MEETING | SAME AS ABOVE | RECOGNIZE FROM SCHEDULE TABLE THAT USER HAS SPARE TIME BEFORE MEETING WITH TROUBLESOME SUPERIOR | | IT IS KNOWN THAT TALKING WITH COLLEAGUE WHO GETS ALONG WITH USER DECREASES STRESS, SO NOTIFY USER TO SET MEETING WITH COLLEAGUE BEFORE MEETING WITH TROUBLESOME SUPERIOR |
| | | | • IF USER IS READY FOR MEETING, LET USER DO ANOTHER TASK TO FORGET MEETING | SAME AS ABOVE | RECOGNIZE THAT USER IS READY FOR MEETING FROM PROGRESS OF CREATION OF MATERIALS AND SELF-TALK SUCH AS "FINALLY FINISHED" | RECOGNIZE FROM SCHEDULE TABLE THAT USER HAS SPARE TIME BEFORE MEETING WITH TROUBLESOME SUPERIOR / IT IS KNOWN FROM PAST DATA THAT CONCENTRATION DECREASES STRESS, SO HIGHLIGHT TASK REGISTERED IN TO DO LIST TO LET USER DO TASK (SUPERIOR MAY BE NOTIFIED THAT USER IS AVAILABLE) | |

INFORMATION PROCESSING APPARATUS AND METHOD

CROSS REFERENCE TO RELATED APPLICATIONS

This application is a U.S. National Phase of International Patent Application No. PCT/JP2018/028031 filed on Jul. 26, 2018, which claims priority benefit of Japanese Patent Application No. JP 2017-153128 filed in the Japan Patent Office on Aug. 8, 2017. Each of the above-referenced applications is hereby incorporated herein by reference in its entirety.

TECHNICAL FIELD

The present technology relates to information processing apparatus and method, and a program, and specifically to information processing apparatus and method, and a program that make a stress level controllable depending on circumstances.

BACKGROUND ART

As a method of measuring stress, there has been proposed a method of estimating a stress level by analyzing heartbeat of a user (refer to PTL 1). In addition, a method of reducing stress depending on the stress level has also been proposed.

CITATION LIST

Patent Literature

Japanese Unexamined Patent Application Publication No. 2012-120206

SUMMARY OF THE INVENTION

Problems to be Solved by the Invention

However, the proposals described above only consider the stress level, and do not consider what is a factor of stress. In order to control stress more precisely, it is desirable to make stress controllable depending on the factor of stress.

The present technology has been devised in view of such circumstances, and makes a stress level controllable depending on circumstances.

Means for Solving the Problem

An information processing apparatus according to one aspect of the present technology includes: a stress level measuring unit that measures a stress level of a user on the basis of a result of detection by a sensor; and a stress factor specifying unit that specifies a factor causing an increase or decrease in the stress level on the basis of an action of the user in a period in which the stress level is increased or decreased.

An information processing method according to one aspect of the present technology includes the processes of: measuring a stress level of a user on the basis of a result of detection by a sensor; and specifying a factor causing an increase or decrease in the stress level on the basis of an action of the user in a period in which the stress level is increased or decreased.

A program according to one aspect of the present technology causes a computer to serve as: a stress level measuring unit that measures a stress level of a user on the basis of a result of detection by a sensor; and a stress factor specifying unit that specifies a factor causing an increase or decrease in the stress level on the basis of an action of the user in a period in which the stress level is increased or decreased.

In one aspect of the present technology, the stress level of the user is measured on the basis of the result of detection by the sensor, and the factor causing the increase or decrease in the stress level is specified on the basis of the action of the user in the period in which the stress level is increased or decreased.

Effect of the Invention

According to the present technology, the stress level is controllable depending on circumstances.

It is to be noted that the effects described here are not necessarily limited, and any of the effects described in the present disclosure may also be included.

BRIEF DESCRIPTION OF THE DRAWINGS

FIG. 6 is a diagram illustrating an example of data used to specify a factor causing stress.

FIGS. 11A and 11B are diagrams illustrating a second display screen example for the smartphone for presenting the factor causing stress.

FIG. 25 is a diagram illustrating a specific example of a stress-relieving act on a holiday.

FIG. 26 is a diagram illustrating a specific example of a stress-relieving act on a weekday.

FIG. 27 is a diagram illustrating a specific example of a stress-relieving act on a weekday.

FIG. 28 is a diagram illustrating a specific example of a stress-relieving act on a weekday.

FIG. 29 is a diagram illustrating a specific example of a stress-relieving act on a weekday.

MODES FOR CARRYING OUT THE INVENTION

The following describes modes for carrying out the present technology (hereinafter referred to as "embodiments"). Description is given in the following order.

0. Summary of Present Technology
1. Configuration Example of Stress Control System
2. Configuration Examples of Input Unit And Output Unit
3. Configuration Example of Processing unit
4. Example of Data Used to Specify Factor Causing Stress
5. Display Screen Examples for Presenting Result of Analysis of Factor Causing Stress
6. Other Presentation Examples
7. Processing Example of Stress Control System
8. Specific Presentation Examples
9. Specific Configuration Examples of Stress Level Increase/decrease Processing Unit
10. Example of Stress Level Increase/decrease Processing
11. System Configuration
12. Hardware Configuration <Summary of Present Technology>

Figure 1:
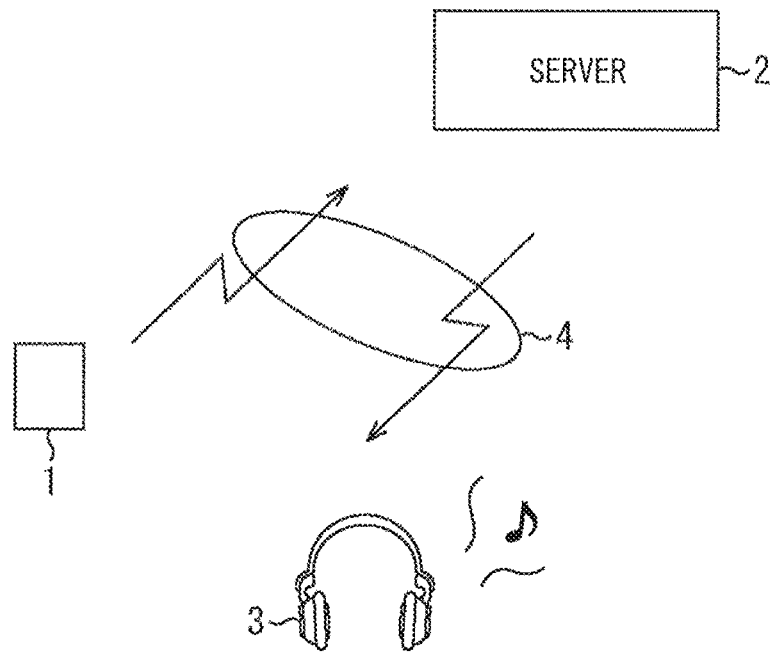
FIG. 1 is a diagram illustrating a basic configuration example of a stress control system to which the present technology is applied.

FIG. 1 is a diagram illustrating a basic configuration example of a stress control system to which the present technology is applied.

The stress control system illustrated in FIG. 1 includes a portable terminal 1, a server 2, and an output device 3.

The portable terminal 1 carried by a user includes a plurality of sensors. The portable terminal 1 transmits sensor data obtained from the plurality of sensors to the server 2 via a network 4. The portable terminal 1 includes a portable device such as a smartphone, a smart watch, or a tablet terminal.

The server 2 receives the sensor data transmitted from the portable terminal 1, and measures a stress level of the user with use of the received sensor data. The stress level is repeatedly measured by the server 2 every time the sensor data is transmitted from the portable terminal 1.

The server 2 specifies a factor causing an increase or decrease in the stress level of the user on the basis of user's action information and the like in a period in which the stress level is increased or decreased, and executes an event corresponding to the specified factor.

In a case where the stress level is higher than a predetermined threshold value, and stress of the user is therefore to be relieved, for example, the server 2 controls headphones as the output device 3 worn by the user and outputs a song that allows the user to relax. For example, in a case where there is a period in which the stress level is low in the past and it has been specified that the user listening to a certain song is a factor contributing to the low stress level, the same song as the song that the user was listening to at that time is played to reduce stress.

Further, in a case where the stress level is lower than the predetermined threshold value, and a sense of tension of the user is therefore to be increased, the server 2 controls the headphones and outputs a song that increases the sense of tension. For example, in a case where there is a period in which the sense of tension (the stress level) is high in the past, and it is specified that the user listening to a certain song is a factor contributing to the high stress level, the same song as the song that the user was listening to at that time is played to increase the sense of tension.

As described above, in the stress control system in FIG. 1, the factor of the stress level is specified on the basis of an action of the user in the period in which the stress level is increased or decreased. In addition, an event for control of the stress level of the user is executed corresponding to the factor of the stress level.

This makes it possible to control the stress of the user.

<Configuration Example of Stress Control System>

Figure 2:
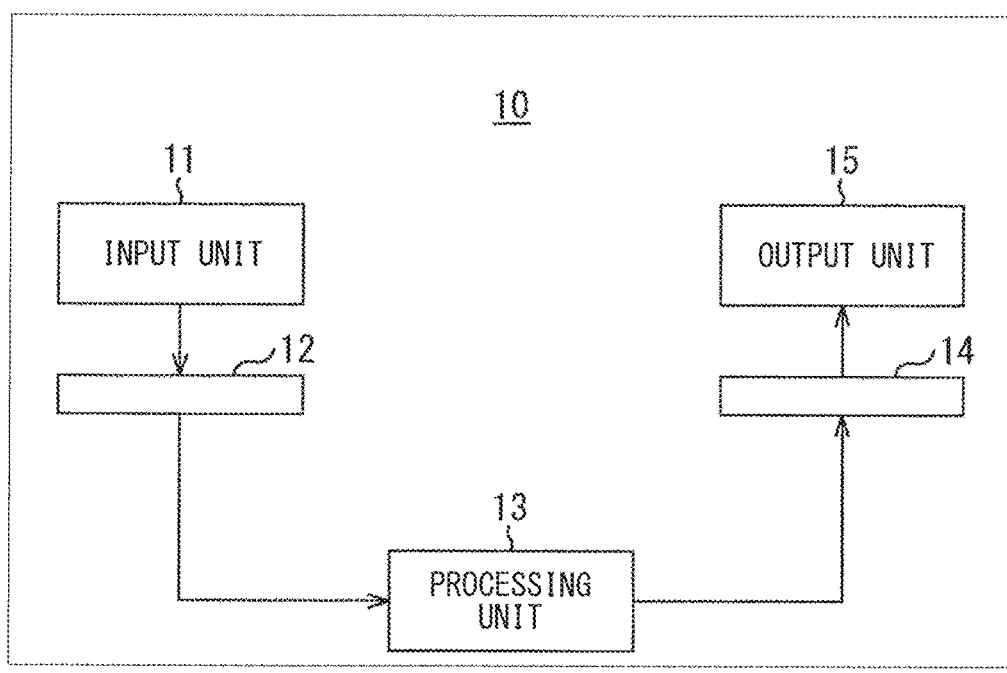
FIG. 2 is a block diagram illustrating an example of an entire configuration of the stress control system.

FIG. 2 is a block diagram illustrating an example of an entire configuration of the stress control system 10.

As illustrated in FIG. 2, a stress control system 10 includes an input unit 11, a processing unit 13, and an output unit 15. The input unit 11, the processing unit 13, and the output unit 15 are implemented in one or a plurality of information processing apparatuses.

In a case where each of the input unit 11, the processing unit 13, and the output unit 15 is implemented as a separate apparatus, for example, the input unit 11 corresponds to the portable terminal 1 in FIG. 1. In addition, the processing unit 13 corresponds to the server 2, and the output unit 15 corresponds to the output device 3.

Further, in a case where the input unit 11, the processing unit 13, and the output unit 15 are implemented in one apparatus, the input unit 11, the processing unit 13, and the output unit 15 are implemented as components in the portable terminal 1, for example.

As described above, an apparatus that implements each of functions of the input unit 11, the processing unit 13, and the output unit 15 is freely changeable. The input unit 11 and the output unit 15 may be implemented in the same apparatus, and the processing unit 13 may be implemented in another apparatus. Alternatively, the processing unit 13 and the output unit 15 may be implemented in the same apparatus, and the input unit 11 may be implemented in another apparatus.

An interface 12 is provided as an interface between the input unit 11 and the processing unit 13, and an interface 14 is provided as an interface between the processing unit 13 and the output unit 15.

In a case where the input unit 11 and the processing unit 13 are implemented in different apparatuses, the interface 12 includes a wired or wireless communication interface. As the communication interface, cellular communication such as 3G/LTE, Wi-Fi, Bluetooth (registered trademark), NFC (Near Field Communication), Ethernet (registered trademark), HDMI (registered trademark) (High-Definition Multimedia Interface), USB (Universal Serial Bus), and the like are used. The Internet may also be interposed between the input unit 11 and the processing unit 13.

In contrast, in a case where the input unit 11 and the processing unit 13 are implemented in the same apparatus, the interface 12 includes a bus or the like in the apparatus (hereinafter, also referred to as an "interface in the apparatus" as appropriate).

Similarly, the interface 14 includes a communication interface or an interface in the apparatus in accordance with component configurations of the processing unit 13 and the output unit 15.

(Input Unit)

The input unit 11 includes an operation input apparatus, a sensor, software for obtaining information from an external service, and the like. The input unit 11 accepts various information inputs from the user, a surrounding environment, and other services.

The operation input apparatus included in the input unit 11 includes, for example, a hardware button, a keyboard, a mouse, a touch panel, a touch sensor, a proximity sensor, an acceleration sensor, an angular velocity sensor, a temperature sensor, and the like, and accepts operation inputs by the user. The operation input apparatus may include a camera, a microphone (mike), and the like that accept inputs by a gesture or voice of the user.

It is to be noted that the input unit 11 may include a processor and a processing circuit that convert data obtained by the operation input apparatus into an operation command. The operation command obtained through conversion by the input unit 11 is outputted to the interface 12. The data obtained by the operation input apparatus may be directly outputted to the interface 12 without being converted into the operation command.

Sensors included in the input unit 11 include sensors such as an acceleration sensor, an angular velocity sensor, a geomagnetic sensor, an illumination sensor, a temperature sensor, and an atmospheric pressure sensor, and detect various types of sensor data.

A sensor that detects biological information of the user, such as a pulse, perspiration, brain waves, a tactile sense, an olfactory sense, and a gustatory sense, may be provided as a sensor included in the input unit 11.

A camera that shoots the user or a surrounding situation, and a microphone that detects voice of the user may be provided as sensors. In this case, the input unit 11 may include a processing circuit that analyzes emotion of the user by analyzing data detected by various sensors including the camera and the microphone.

In addition, a positioning sensor may also be provided. Specifically, a GNSS (Global Navigation Satellite System) receiver such as a GPS (Global Positioning System) receiver, a GLONASS (Global Navigation Satellite System) receiver, or a BDS (BeiDou Navigation Satellite System) receiver is provided as the positioning sensor.

A communication apparatus that detects a position with use of a technology such as Wi-Fi, MIMO (Multi-Input Multi-Output), cellular communication, or short-range wireless communication (for example, BLE (Bluetooth) (registered trademark) Low Energy), or Bluetooth (registered trademark)) may be used as a positioning sensor.

The apparatus including the sensors as described above is carried or worn by the user, and detection of a position of the user and detection of a situation of the user including biological information are repeated.

The apparatus including the sensors may be installed in a living environment of the user, and the position and the situation of the user may be repeatedly detected by such an apparatus. For example, an image including a face of the user obtained by a camera fixedly installed in a room or the like is analyzed, which makes it possible to detect a pulse of the user.

The software for obtaining information from an external service, which is included in the input unit 11, obtains various types of information provided by the external service with use of, for example, an API (Application Program Interface). The software may obtain information from a server of the external service, or may obtain information from an application executed by a client apparatus.

The software obtains information such as, for example, texts and images posted to external services such as social media by the user or other users. The obtained information may include a log of operations executed by the user or other users, and the like.

Information delivered to many and unspecified users, such as news, weather forecasts, traffic information, a POI (Point Of Interest), or advertisements, may also be obtained.

<Configuration Examples of Input Unit and Output Unit>

Figure 3:
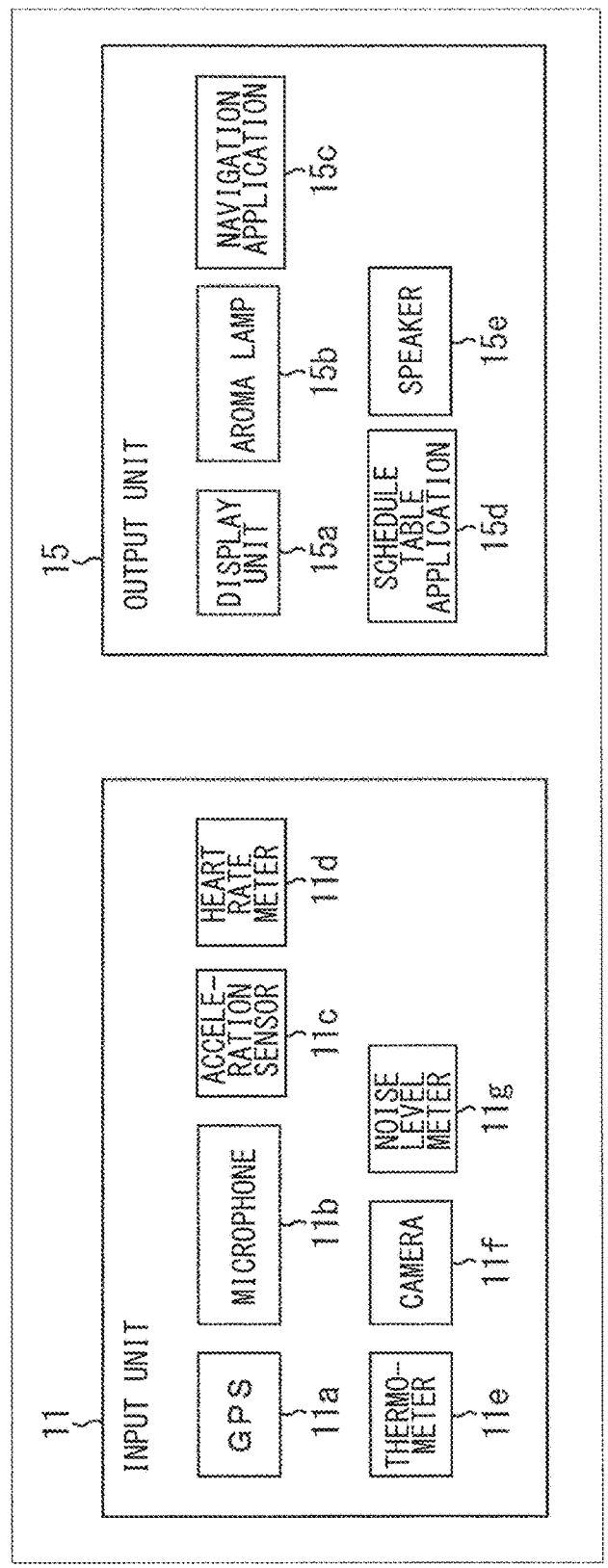
FIG. 3 is a diagram illustrating specific examples of an input unit and an output unit.

A specific example of the input unit 11 is illustrated in FIG. 3.

In the example in FIG. 3, the input unit 11 includes a GPS 11a, a microphone 11b, an acceleration sensor 11c, a heart rate meter 11d, a thermometer 11e, a camera 11f, and a noise level meter 11g. Various operation input apparatuses and various sensors described above are also included in the input unit 11. The operation input apparatuses and the sensors described above are not described.

The heart rate meter 11d measures a heart rate of the user, and the thermometer 11e measures a body temperature of the user. The noise level meter 11g detects ambient noise around the user. These components of the input unit 11 are provided in the portable terminal 1, for example.

(Processing Unit)

For example, the processing unit 13 corresponding to the server 2 executes various types of processing on the basis of information obtained by the input unit 11. For example, the processing unit 13 may include a processor or a processing circuit such as a CPU (Central Processing Unit), a GPU (Graphics processing unit), a DSP (Digital Signal Processing unit), an ASIC (Application Specific Integrated Circuit), or an FPGA (Field-Programmable Gate Array).

The processing unit 13 may include a memory or a storage apparatus that temporarily or permanently stores a program to be executed in the processor or the processing circuit and data to be read or written in processing.

It is to be noted that the processing unit 13 may be implemented by a single processor or a single processing circuit in a single apparatus, or may be implemented by being distributed over a plurality of processors or processing circuits in a plurality of apparatuses or the same apparatus.

In a case where the processing unit 13 is implemented by being distributed, a communication interface or an interface in an apparatus that is similar to the interface 12 is interposed between respective components that implement functions of the processing unit 13.

(Output Unit)

The output unit 15 outputs information supplied from the processing unit 13, and presents the information to the user. The user to which the information is presented may be the same as or different from the user of the input unit 11.

An output apparatus included in the output unit 15 outputs information supplied from the processing unit 13 in a form perceivable by the user by at least one of a visual sense, an auditory sense, a tactile sense, an olfactory sense, or a gustatory sense.

For example, it is possible to include a display in the output apparatus. As the display, a reflective or self-luminous type display such as an LCD (Liquid Crystal Display) display or an organic EL (Electro-Luminescence) display may be used, or a display module used in a wearable apparatus or the like may be used. The display module includes a combination of a light guiding member that guides image display light to eyes of the user and a light source.

The output unit 15 may include a speaker, or may include an external apparatus that presents information to the user, such as a projector or a vibrator.

The information supplied from the processing unit 13 may be outputted by an application presenting information to the user. In this case, the application presenting the information to the user is included in the output unit 15.

As illustrated in FIG. 3, the output unit 15 includes, for example, a display unit 15a, an aroma lamp 15b, a navigation application 15c (navigation app 15c), a schedule table application 15d (schedule table app 15d), and a speaker 15e.

The respective components of the output unit 15 illustrated in FIG. 3 may be provided in the portable terminal 1, or may be implemented as an apparatus different from the portable terminal 1.

The display unit 15a displays information provided by the processing unit 13. The aroma lamp 15b outputs information provided from the processing unit 13 in a form perceived by the olfactory sense.

The navigation app 15c is an application for routing assistance. The schedule table app 15d is an application for managing and outputting a schedule of the user.

The speaker 15e includes a stationary speaker or headphones. The speaker 15e outputs information supplied from the processing unit 13 as voice.

<Configuration Example of Processing Unit>

Figure 4:
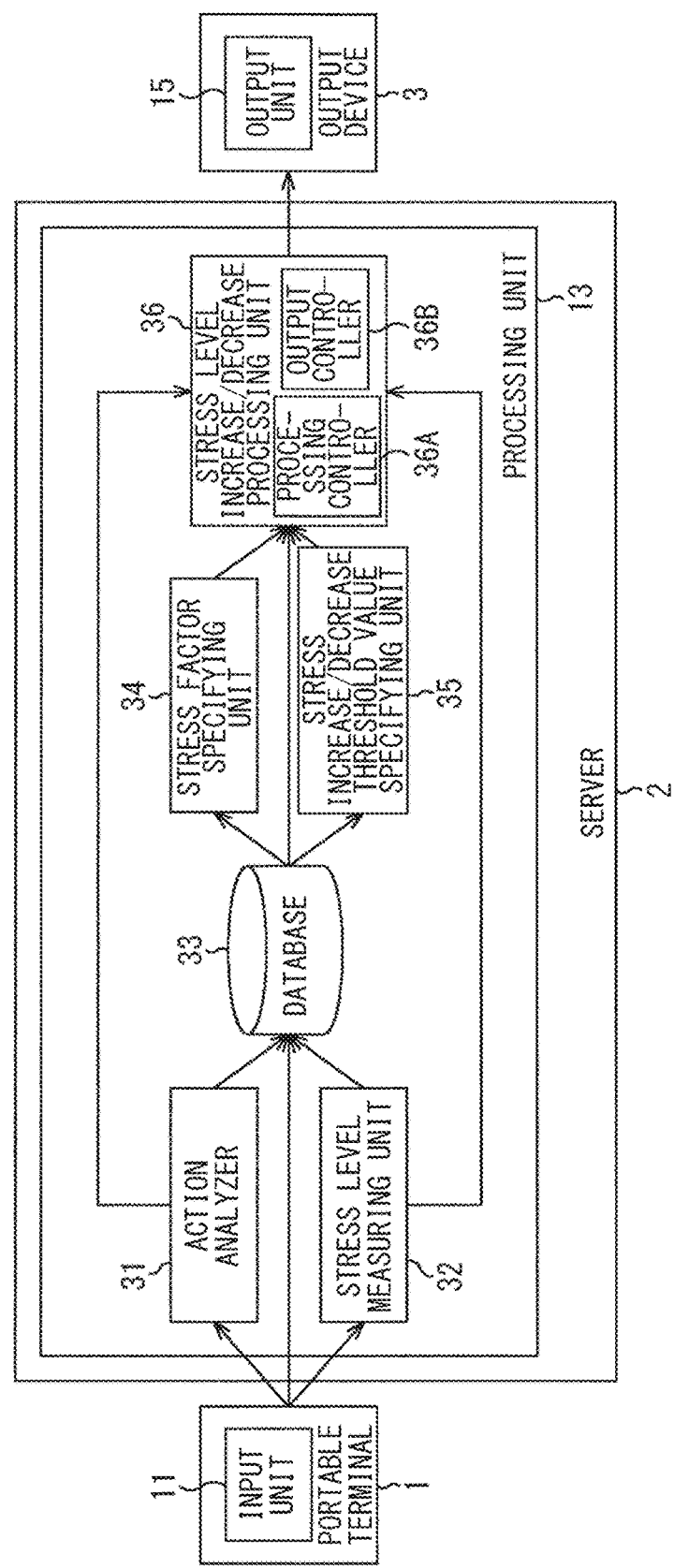
FIG. 4 is a block diagram illustrating a configuration example of a processing unit.

FIG. 4 is a block diagram illustrating a configuration example of the processing unit 13.

Herein, description is given of a case where the input unit 11, the processing unit 13, and the output unit 15 illustrated in FIG. 3 are implemented in different apparatuses. The input unit 11 is implemented in the portable terminal 1 in FIG. 1, and the processing unit 13 is implemented in the server 2. The output unit 15 is implemented in the output device 3.

The processing unit 13 includes an action analyzer 31, a stress level measuring unit 32, a database 33, a stress factor specifying unit 34, a stress increase/decrease threshold value specifying unit 35, and a stress level increase/decrease processing unit 36. Information obtained by the input unit 11 is supplied to the action analyzer 31, the stress level measuring unit 32, and the database 33.

The action analyzer 31 analyzes an action of the user on the basis of information obtained by the input unit 11. For example, the action analyzer 31 analyzes a motion state of the user such as walking, running, or riding on a train, a location of the user, an application used by the user, a song having been listened to by the user, information of a companion, and the like. Information representing the action of the user analyzed by the action analyzer 31 is supplied to the database 33 and the stress level increase/decrease processing unit 36.

The stress level measuring unit 32 measures an integrated stress level of the user on the basis of information obtained by the input unit 11. Information representing the stress level measured by the stress level measuring unit 32 is supplied to the database 33 and the stress level increase/decrease processing unit 36.

Information obtained by the input unit 11 includes measurement data such as a location, acceleration, brightness, vasoconstriction, a heart rate, respiration, perspiration, a skin temperature, a skin electrical resistance value, image data, and voice data.

Herein, a stress level Q is represented by the following expression (1), where various types of measurement data are $\{x\_i\}$ ($i=1, 2, \ldots, n$). An algorithm F that estimates Q from $\{x\_i\}$ is determined by machine learning or a statistical technique.

[Math. 1]

$$Q = F(\{x\_i\}) + \delta \qquad \text{[Math. 1]}$$

$\delta$ is an error associated with estimation. A large number of sets of measurement data $\{x\_i\}$ and the stress level Q are used to determine the algorithmic F that allows $\delta$ to be as small as possible.

In a case where the algorithm F is determined, it is possible to estimate the stress level Q with use of newly obtained (or assumed) measurement data $\{x\_i\}$.

It is to be noted that as a method of measuring the stress level, the following methods described in reference literatures may be used.

Japanese Unexamined Patent Application Publication No. 2003-153905 describes that it is possible to use a measurement value of a physiological change such as vasoconstriction, a heart rate, respiration, perspiration, and a skin temperature adjusted by an autonomic nervous system in order to objectively evaluate whether a body and a mind are in a stress state or a relaxed state.

In addition, Japanese Unexamined Patent Application Publication No. 2003-153905 or Japanese Unexamined Patent Application Publication (Published Japanese Translation of PCT Application) No. 2014-514080 describes a method of measuring stress by measuring a skin temperature, a skin electrical resistance value, and skin conductance.

Japanese Unexamined Patent Application Publication No. 2009-100088 describes a method of measuring stress by using a stress diagnosis based on an interview form together with a skin electrical resistance value.

There is also a technology for measuring stress from voice. Japanese Unexamined Patent Application Publication No. 2010-273700 describes a method of using voices of talkers having a dialogue as inputs and determining stress of the talkers with use of a length of overlap of voice signals of the talkers.

Japanese Unexamined Patent Application Publication (Published Japanese Translation of PCT Application) No. 2010-506206 describes a method of calculating spectral characteristics of a voice signal and measuring stress on the basis of the spectral characteristics.

As described above, in the stress level measuring unit 32, the stress level is measured integrally by using various methods in an appropriate combination.

In the database 33, an action history of the user analyzed by the action analyzer 31, the stress level measured by the stress level measuring unit 32, measurement data supplied from the input unit 11, and the like are registered in association with each other.

The stress factor specifying unit 34 specifies whether the stress level is increased or decreased by referring to information registered in the database 33 and comparing the stress levels at different times with each other.

It is assumed that stress levels at times t1 and t2 (t1<t2) are respectively Q_t1 and Q_t2. In this case, satisfying a condition represented by the following expression (2) indicates that the stress level is decreased. In addition, satisfying a condition represented by the following expression (3) indicates that stress level is increased.

[Math. 2]

$$Q\_t1 - Q\_t2 > 0 \qquad (2)$$

[Math. 3]

$$Q\_t1 - Q\_t2 < 0 \qquad (3)$$

In addition, the stress factor specifying unit 34 extracts, from the action history, an action of the user in a duration (between the time t1 and the time t2) in which the stress level is increased or decreased, and also extracts, from the measurement data, information that is an external factor causing stress such as noise.

The stress factor specifying unit 34 specifies a factor causing the stress level to be increased or a factor causing the stress level to be decreased, on the basis of the extracted action and the external factor. The factor may be specified on the basis of one of the action of the user and the external factor. The factor causing an increase or decrease in the stress level is also specified, for example, by machine learning or a statistical technique.

Information relating to the factor specified by the stress factor specifying unit 34 is supplied to the stress level increase/decrease processing unit 36.

The stress increase/decrease threshold value specifying unit 35 specifies a threshold value for generating an event.

Threshold Value Calculating Method 1

The stress increase/decrease threshold value specifying unit 35 determines an average stress level of an individual on the basis of stress levels measured in a long term and accumulated in the database 33.

In a case where the stress level is increased to a certain extent with reference to the average stress level, the stress increase/decrease threshold value specifying unit 35 asks the user a question such as "do you want to relax?" or "are you irritated?" and determines a threshold value from an answer to the question from the user.

For example, if the user answers "I want to relax" in the case where the stress level is increased to a certain extent as compared with an average, it is assumable that the stress level is increased for the user. In this case, the current stress level, which is increased to a certain extent as compared with the average, is specified as a threshold value. The threshold value thus determined is used as a criterion by which to judge whether or not to generate an event to decrease the stress level.

In addition, in a case where the stress level is decreased to a certain extent with reference to the average stress level, the stress increase/decrease threshold value specifying unit 35 asks the user a question such as "do you want a stimulus" or "are you too relaxed", and determines a threshold value from an answer to the question from the user.

For example, if the user answers "I want a stimulus" in the case where the stress level is decreased to a certain extent as compared with the average, it is assumable that the user feels the stress level being decreased. In this case, the current stress level, which is decreased to a certain extent as compared with the average, is specified as a threshold value. The threshold value thus determined is used as a criterion by which to judge whether or not to generate an event to increase the stress level.

Threshold Value Calculating Method 2

The stress increase/decrease threshold value specifying unit 35 determines an average stress level of an individual on the basis of stress levels measured in a long term and accumulated in the database 33.

In addition, the stress increase/decrease threshold value specifying unit 35 determines correlations with a disease (such as diarrhea and constipation) suffered by the user, a sleep duration, a dietary intake, a shopping volume, an opportunity to go out, and the like by machine learning and a statistical technique in a case where the stress level is increased to a certain extent with reference to the average stress level. The stress increase/decrease threshold value specifying unit 35 sets, as a threshold value, a stress level at which a change in the correlations occur.

The stress increase/decrease threshold value specifying unit 35 outputs the threshold value thus specified to the stress level increase/decrease processing unit 36 and sets the threshold value.

The stress level increase/decrease processing unit 36 includes a processing controller 36A and an output controller 36B.

The processing controller 36A compares the stress level of the user supplied from the stress level measuring unit 32 with the threshold value set by the stress increase/decrease threshold value specifying unit 35. For example, in a case where the stress level of the user is higher than the threshold value, the processing controller 36A detects a factor causing the stress level to be decreased on the basis of information supplied from the stress factor specifying unit 34, and performs event processing corresponding to the detected factor. For example, processing of suggesting taking an action that is the factor causing the stress level to be decreased is executed as event processing.

In addition, in a case where the stress level of the user is lower than the threshold value, the processing controller 36A detects a factor causing the stress level to be increased on the basis of information supplied from the stress factor specifying unit 34, and executes an event corresponding to the detected factor. For example, processing of suggesting taking an action that is the factor causing the stress level to be increased is executed as event processing. It is to be noted that a threshold value used in a case where stress is decreased and a threshold value in a case where stress is increased may be different from each other.

The output controller 36B causes the output unit 15 to output information representing an increase or decrease in the stress level together with information representing the factor. For example, the output unit 15 outputs a display screen for presenting a factor causing stress, a display screen for presenting a result of analysis of the factor causing stress, a voice for a suggestion, and the like. The factor causing stress is described later.

<Anther Configuration Example of Processing Unit>

Figure 5:
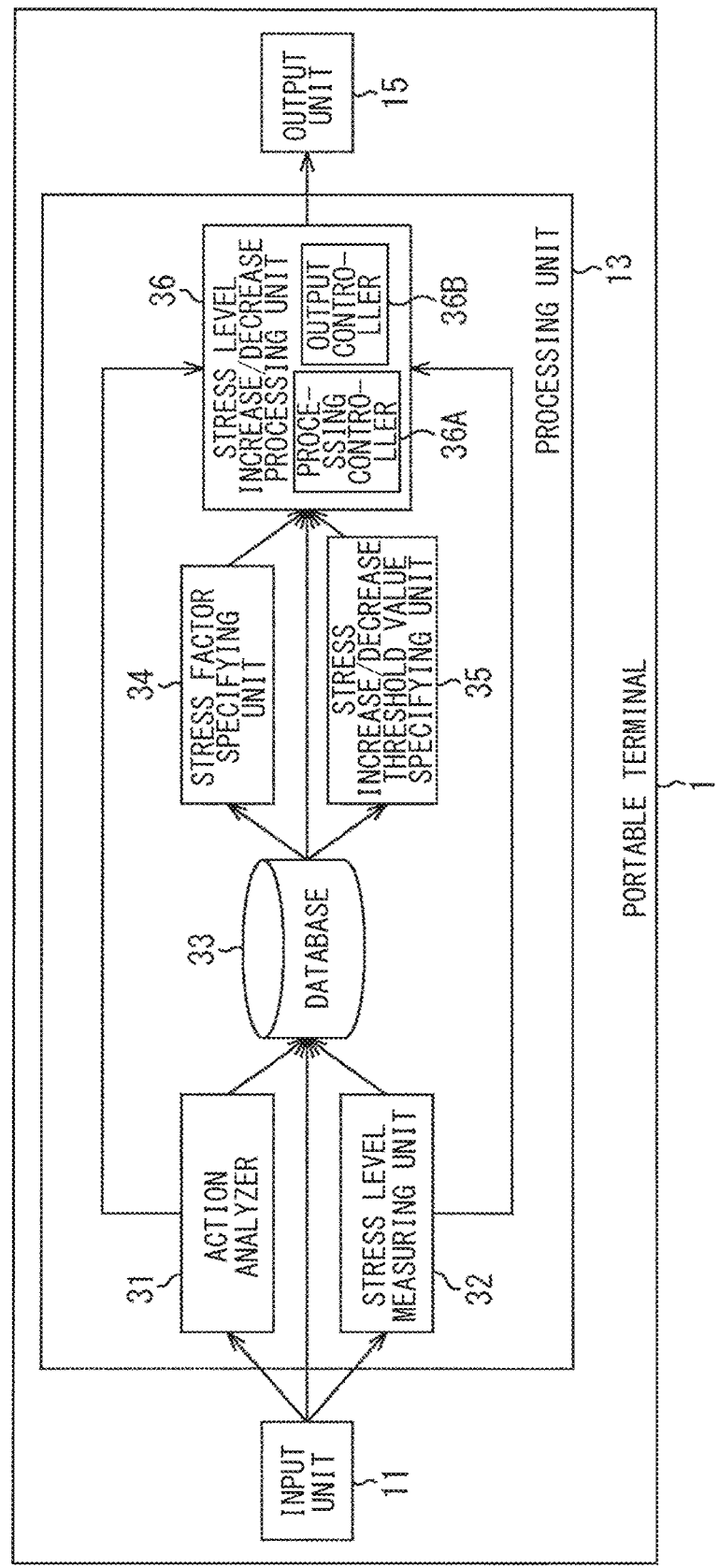
FIG. 5 is a block diagram illustrating another configuration example of the processing unit.

FIG. 5 is a block diagram illustrating another configuration example of the processing unit 13. Of the components illustrated in FIG. 5, the same components as those described with reference to FIG. 4 are denoted by the same reference numerals. Redundant descriptions thereof are omitted as appropriate In the example in FIG. 5, the input unit 11, the processing unit 13, and the output unit 15 are implemented by the portable terminal 1 as a single apparatus.

As described above, it is possible for the portable terminal 1 to have the functions of the input unit 11, the processing unit 13, and the output unit 15.

<Example of Data Used to Specify Factor Causing Stress>

FIG. 6 is a diagram illustrating an example of data used to specify the factor causing stress. Types of data, data to be used, and obtaining methods are illustrated in order from the left.

The types of data include one-dimensional discrete quantity, one-dimensional continuous quantity, and position information. The one-dimensional discrete quantity represents data that is detected not in a fixed cycle, but at a predetermined timing. The one-dimensional continuous quantity represents data that is detected in a fixed cycle.

Data belonging to types of the one-dimensional discrete quantity includes data relating to transportation means, data relating to an application in use, data relating to music being listened to, and data relating to a TV program being viewed. In addition, the data belonging to the type of the one-dimensional discrete quantity includes data relating to a companion, data relating to time zones, and data relating to seasons.

Data of transportation means represents transportation means by the user such as a standstill, walking, and a train. The data of transportation means is obtained by analyzing a vibrational pattern by the acceleration sensor.

Data of the application in use is obtained by specifying a foreground application such as the navigation app 15c or the schedule table app 15d.

Data of the music being listened to is obtained by obtaining a song being played or by estimating a song from sounds collected by the microphone 11b.

Data of the TV program being viewed is obtained by estimating a program from sounds collected by the microphone 11b.

Data of the companion represents another user who is with the user. The data of the companion is obtained by determining that the position information of the user and the other user by the GPS 11a is mutually close, that both the user and the other user are within a scanning range of the Bluetooth (registered trademark), or that both the user and the other user are within a Wi-Fi scanning range.

Data of the time zones represents time zones such as morning, afternoon, and night. The data of the time zones is obtained by a built-in clock in an apparatus such as the portable terminal 1 that includes the input unit 11.

Data of the seasons represents seasons such as spring, summer, autumn, and winter. The data of the seasons is also obtained by the built-in clock in the apparatus.

Data belonging to types of one-dimensional continuous quantity includes data relating to a noise level, data relating to brightness, and data relating to exercise intensity.

Data of the noise level is obtained by measuring a sound pressure by the microphone 11b. The data of the noise level may be obtained by the noise level meter 11g.

Data of the brightness is obtained by measuring brightness by an illumination sensor.

Data of the exercise intensity is obtained by analyzing a vibrational pattern by the acceleration sensor 11c.

Data belonging to types of position information includes data of a current location. Data of the current location is obtained by storing a positioning history by the GPS 11a or by storing an entry/exit history by a Map application (not illustrated).

It is to be noted that the method of obtaining each of the data illustrated in FIG. 6 is only an example, and each of the data may be obtained by any other method.

<Display Screen Examples for Presenting Factor Causing Stress>

Hereinafter, examples of a display screen displayed on the display unit 15a is described.

A display screen for a smartphone illustrated in the diagram is a screen of the display unit 15a provided in the smartphone as the portable terminal 1, and a display screen for a smart watch is a screen of the display unit 15a provided in the smart watch as the portable terminal 1. After the factor causing stress is specified by the stress factor specifying unit 34, various screens are displayed by the output controller 36B in response to an operation by the user.

Figure 7B:
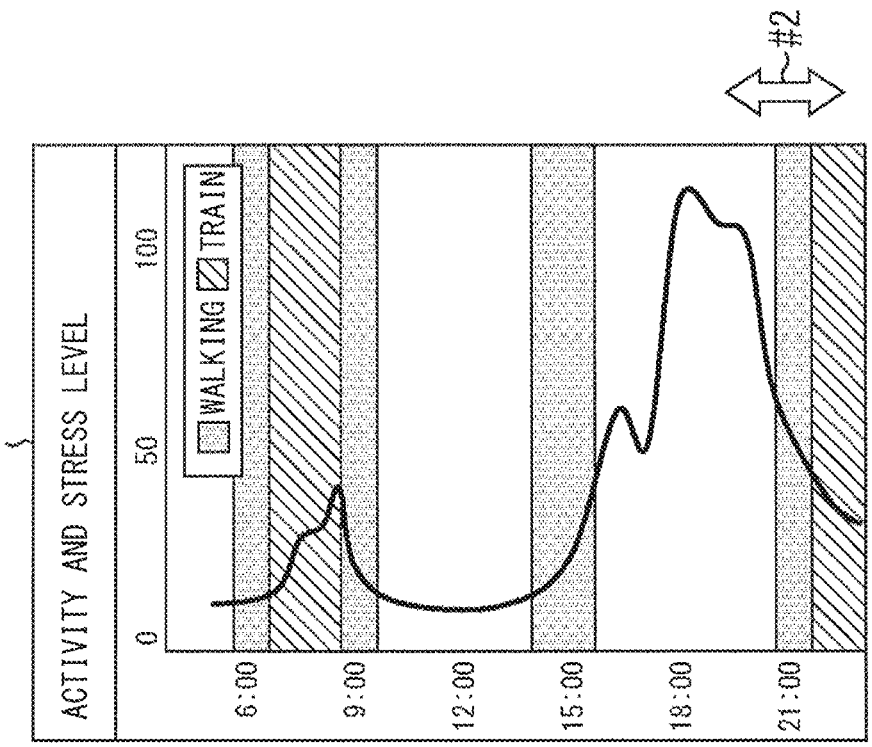
FIGS. 7A and 7B are diagrams illustrating a first display screen example for a smartphone for presenting a factor causing stress.
Figure 7A:
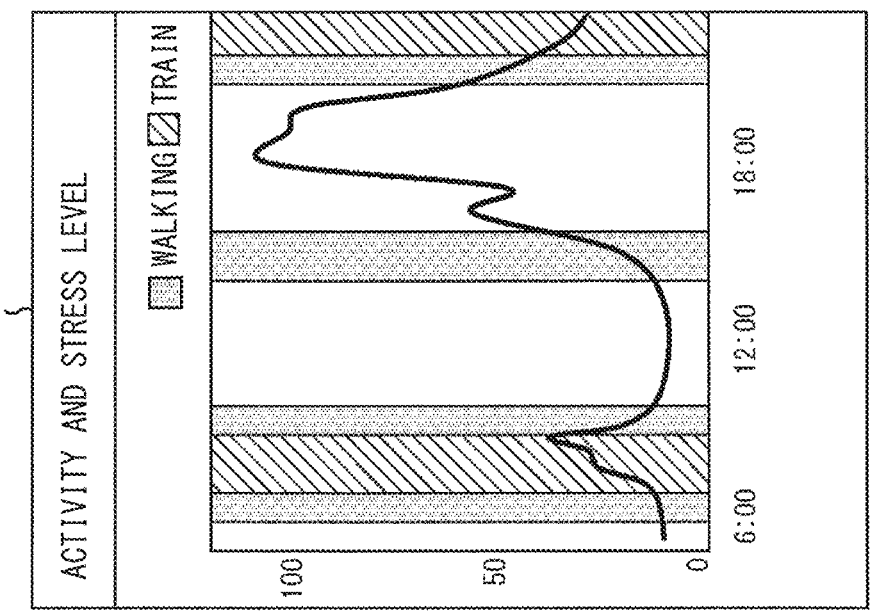

FIGS. 7A and 7B are diagrams illustrating a display screen example for the smartphone for presenting the factor causing stress.

A display screen 101 in FIG. 7A is a vertical screen presenting a relationship between activity and the stress level. A horizontal direction of a graph displayed on the display screen 101 represents time, and a vertical direction represents the stress level. A white arrow #1 in the horizontal direction represents that the time zone is switchable by horizontal scrolling.

In the display screen 101, a transportation means in each of time zone is displayed as an activity. A finely hatched time zone represents that a transportation means in the time zone is walking, and an obliquely hatched time zone represents that a transportation means in the time zone is a train. A non-hatched time zone represents a standstill, that is, not moving in the time zone. Although each transportation means is hatched in the diagram, actually, for example, a different color is displayed for each transportation means.

A time series of the stress level is represented by a solid line superimposed on display of activities in respective time zones.

Viewing the display screen 101 makes it possible for the user to confirm that the stress level is increased while traveling on a train from about 7:00 to about 9:00. In addition, it is possible for the user to confirm that there is almost no stress when the user is not moving at about 12:00, and stress is large when the user is not moving at about 18:00.

As a result, it is possible for the user to confirm a relationship between an increase or decrease in the stress level and transportation means as a factor causing the increase or decrease in the stress level, such as riding on a train in a duration for going to work being a factor causing an increase in the stress level.

In addition, in a case in FIGS. 7A and 7B, the stress factor specifying unit 34 assumes that a duration from about 7:00 to about 9:00 in the duration for going to work is a duration in which the stress level is increased, and riding on a train in the duration for going to work, which is an action of the user at this time, is the factor causing the increase in the stress level. Further, the stress factor specifying unit 34 assumes that a duration from about 9:00 to about 10:00 is a duration in which the stress level is decreased, and getting off the train, which is an action of the user at this time, is a factor causing the decrease in the stress level.

A display screen 102 in FIG. 7B is a screen in which the display screen 101 is oriented horizontally. A white arrow #2 in the vertical direction represents that the time zone is switchable by vertical scrolling.

Figure 8:
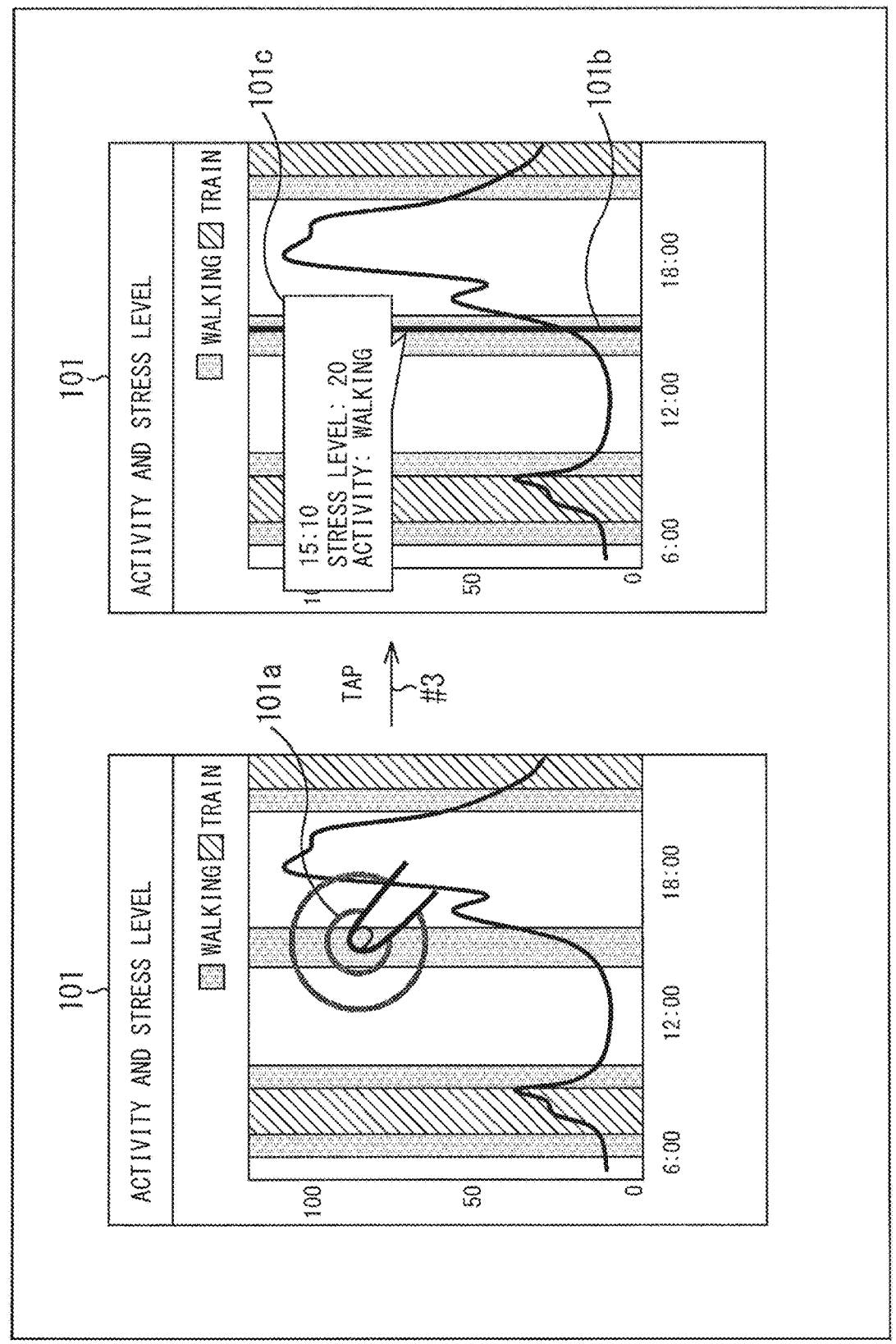
FIG. 8 is a diagram illustrating an example of an operation by a user on a display screen for the smartphone

FIG. 8 is a diagram illustrating an example of an operation by the user on the display screen 101.

In a case where the user taps a certain position on the display screen 101 with a finger, as illustrated on a left side of FIG. 8, a circular image 101a centered on the position tapped with the finger is displayed. In a case where long-pressing is performed for a predetermined time while this state is held, a state of the display screen 101 transits to a state in which detailed information is displayed, as indicated by an arrow #3.

A line 101b representing a time of the tapped position and a balloon 101c presenting detailed information at the time represented by the line 101b are displayed on the display screen 101 on a right side of FIG. 8. The balloon 101c represents, as the detailed information, that the time is "15:10" and the stress level at that time is "20". In addition, the balloon 101c represents that an activity at "15:10" is "walking".

As described above, tapping a predetermined time on the display screen 101 presenting the factor causing stress makes it possible for the user to know detailed information about the stress level and the activity at that time.

Figure 9:
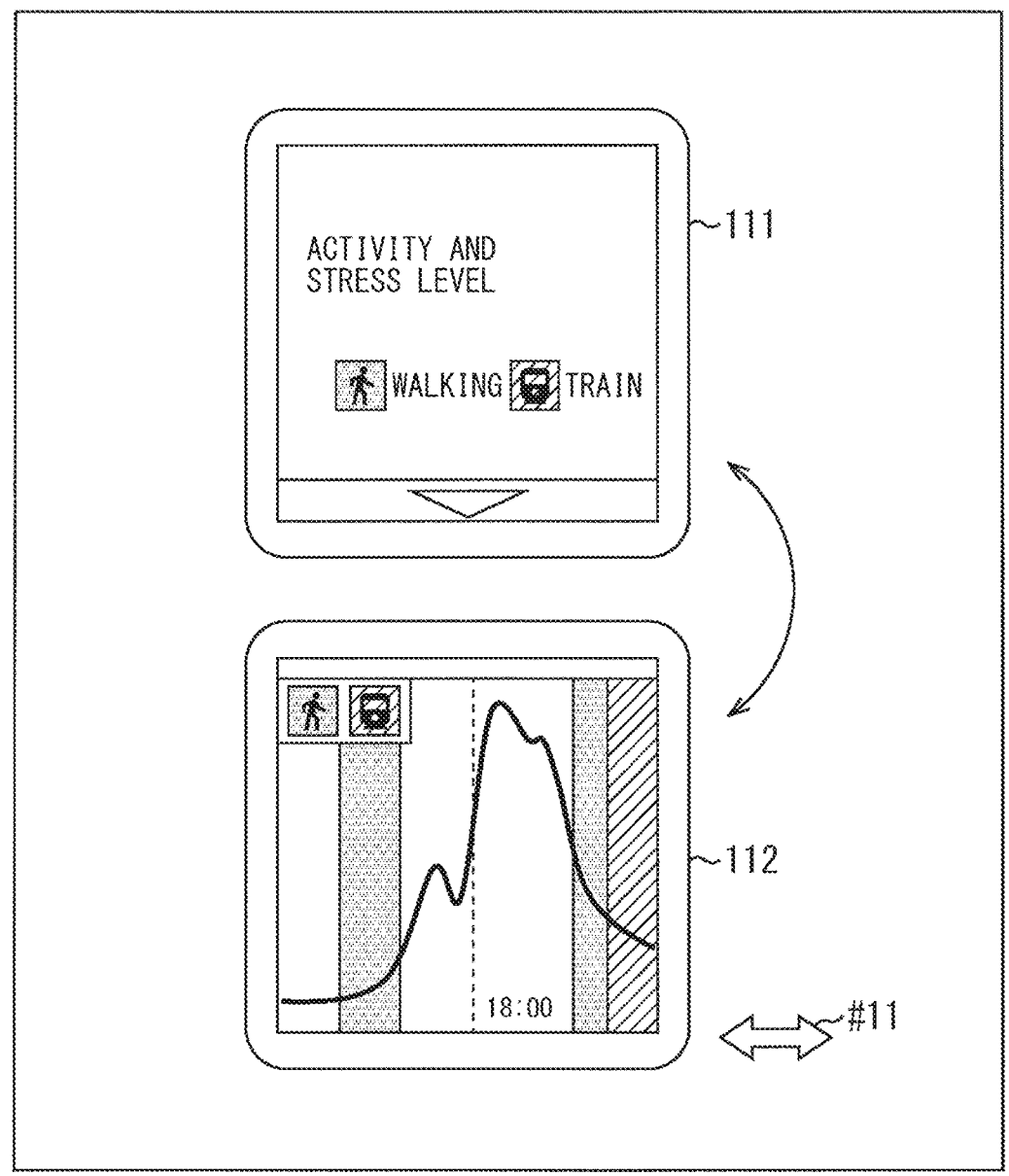
FIG. 9 is a diagram illustrating a first display screen example for a smart watch for presenting a factor causing stress.

FIG. 9 is a diagram illustrating a display screen example for a smart watch for presenting the factor causing stress.

A display screen for the smart watch has a smaller display range than the display screen for the smartphone. The display screen for the smart watch is divided into a display screen 111 for describing display contents and a display screen 112 representing a relationship between activity and the stress level.

The display screen 111 represents contents displayed on the display screen 112, which is "activity and the stress level", and descriptions of a "walking" icon and a "train" icon. A downward triangle displayed in a lower portion of the display screen 111 represents that transition to the display screen 112 is enabled by upward swiping.

The display screen 112 displays a time series of the stress level superimposed on transportation means in respective time zone, as with the display screen 101. A white arrow #11 in the horizontal direction represents that the time zone is switchable by horizontal scrolling.

It is also possible for the user to confirm a relationship between an increase or decrease in the stress level and transportation means as a factor causing the increase or decrease in the stress level even on such a display screen.

Figure 10:
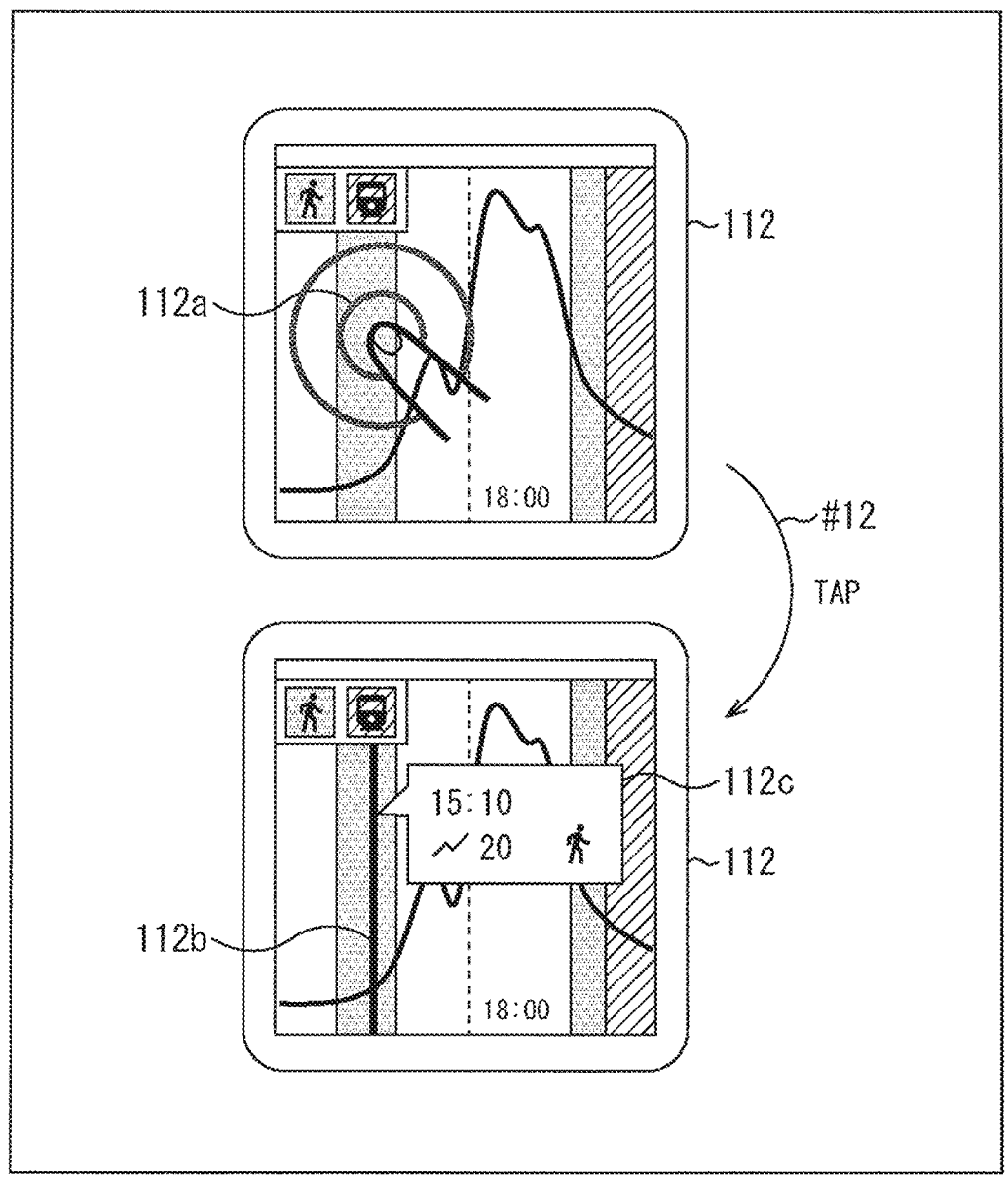
FIG. 10 is a diagram illustrating an example of an operation by the user on a display screen for the smart watch.

FIG. 10 is a diagram illustrating an example of an operation by the user on the display screen 112.

An operation of the display screen 112 is also basically similar to the operation of the display screen 101 described with reference to FIG. 8. That is, the user taps a position on the display screen 112 with a finger. In response to this, as illustrated in FIG. 10, a circular image 112a centered on the position tapped with the finger is displayed on the display screen 112. In a case where long-pressing is performed for a predetermined time while this state is held, a state of the display screen 112 transits to a state in which detailed information is displayed, as indicated by an arrow #12.

A line 112b representing a time of the tapped position and a balloon 112c presenting detailed information at the time represented by the line 112b are displayed on the display screen 112 in a lower stage of FIG. 10. The balloon 112c represents, as the detailed information, that the time is "15:10" and the stress level at that time is "20". In addition, an icon indicates that activity at "15:10" is "walking".

FIGS. 11A and 11B are diagrams illustrating another display screen example for the smartphone for presenting the factor causing stress.

A display screen 121 in FIG. 11A is a vertical display screen presenting a relationship between noise and the stress level. A horizontal direction of a graph displayed on the display screen 121 represents time, and a vertical direction represents the stress level. A white arrow #21 in the horizontal direction represents that the time zone is switchable by horizontal scrolling.

In the display screen 121, a solid line represents the stress level at each time, and a broken line represents a noise level at each time. Although line types are illustrated separately in the diagram, actually, for example, a different color may be displayed for each graph.

As described above, the display screen 121 displays a time series of the stress level together with a time series of the noise level in each time zone.

Viewing the display screen 121 makes it possible for the user to confirm that the stress level is increased in a duration from about 7:00 to about 9:00 in which the noise level is as high as about 70. In addition, it is possible for the user to confirm that there is almost no stress at about 12:00 at which the noise level is decreased, and the stress level is increased at about 18:00 at which the noise level is increased to about 50.

As a result, it is possible for the user to confirm a relationship between an increase or decrease in the stress level and noise as a factor causing the increase or decrease in the stress level, such as a high noise level being a factor causing an increase in the stress level.

A display screen 122 in FIG. 11B is a screen in which the display screen 121 is oriented horizontally. A white arrow #22 in the vertical direction represents that the time zone is switchable by vertical scrolling.

Figure 12A:
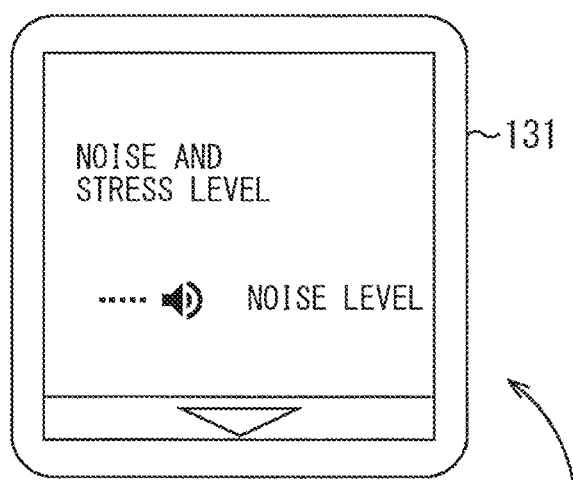
FIGS. 12A and 12B are diagrams illustrating a second display screen example for the smart watch for presenting the factor causing stress.
Figure 12B:
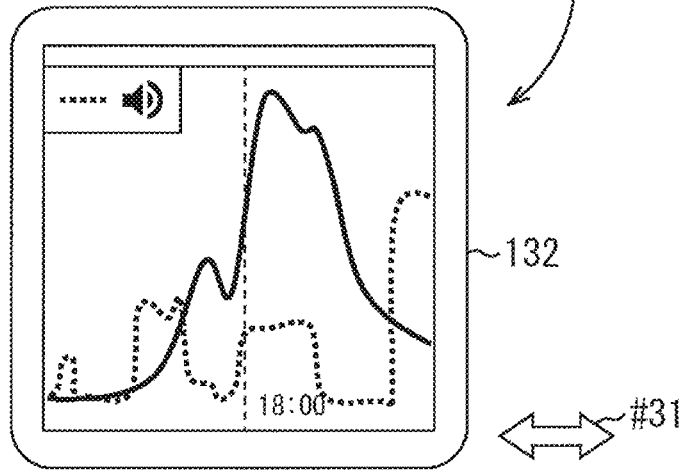

FIGS. 12A and 12B are diagrams illustrating another display screen example for the smart watch for presenting the factor causing stress.

A display screen for the smart watch is divided into a display screen 131 for describing display contents and a display screen 132 representing a relationship between noise and the stress level.

The display screen 131 represents contents displayed on the display screen 132, which is "noise and the stress level", and a description of a "noise level" icon. A downward triangle displayed in a lower portion of the display screen 131 represents that transition to the display screen 132 is enabled by upward swiping.

As with the display screen 131, the display screen 132 displays a time series of the stress level and a time series of the noise level in respective time zones. A white arrow #31 in the horizontal direction represents that the time zone is switchable by horizontal scrolling.

It is also possible for the user to confirm a relationship between an increase or decrease in the stress level and the noise level as a factor causing the increase or decrease in the stress level even on such a display screen.

Figure 13:
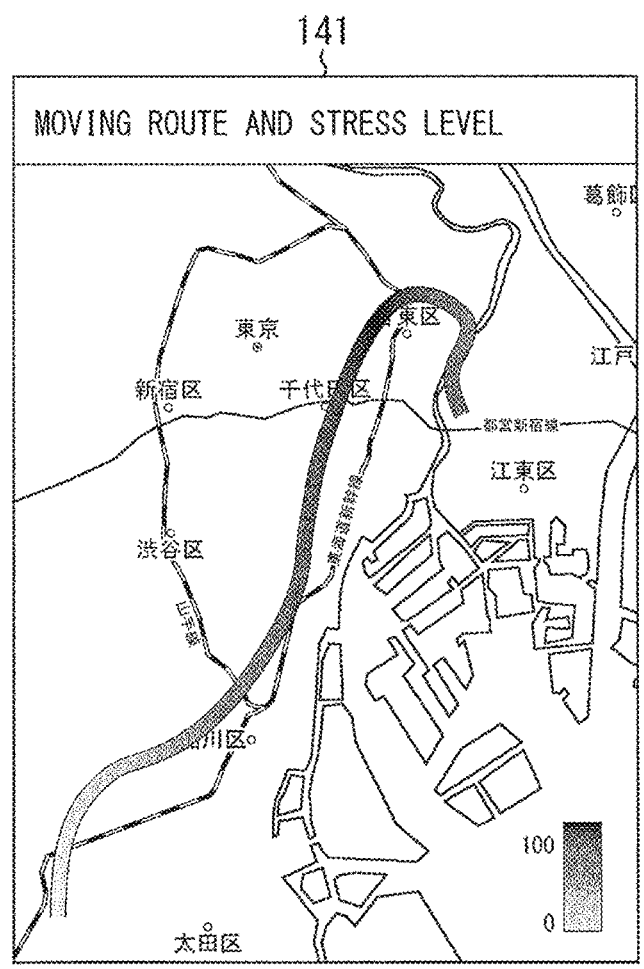
FIG. 13 is a diagram illustrating a third display screen example for the smartphone for presenting the factor causing stress.

FIG. 13 is a diagram illustrating still another display screen example for the smartphone for presenting the factor causing stress.

A display screen 141 in FIG. 13 is a screen presenting a relationship between a moving route and the stress level.

The display screen 141 displays a map of a range including a moving route of the user, and the moving route obtained from a history of position information (a current location) is displayed with colors (gradations of 0 to 100) representing the stress level. That is, with use of a location where the user is present as a factor, the display screen 141 is represented by a screen presenting a relationship between the location of the user as the factor and the stress level.

Viewing the display screen 141 makes it possible for the user to confirm that the stress level is increased as the user moves from the bottom left to the top right of the map.

Figure 14:
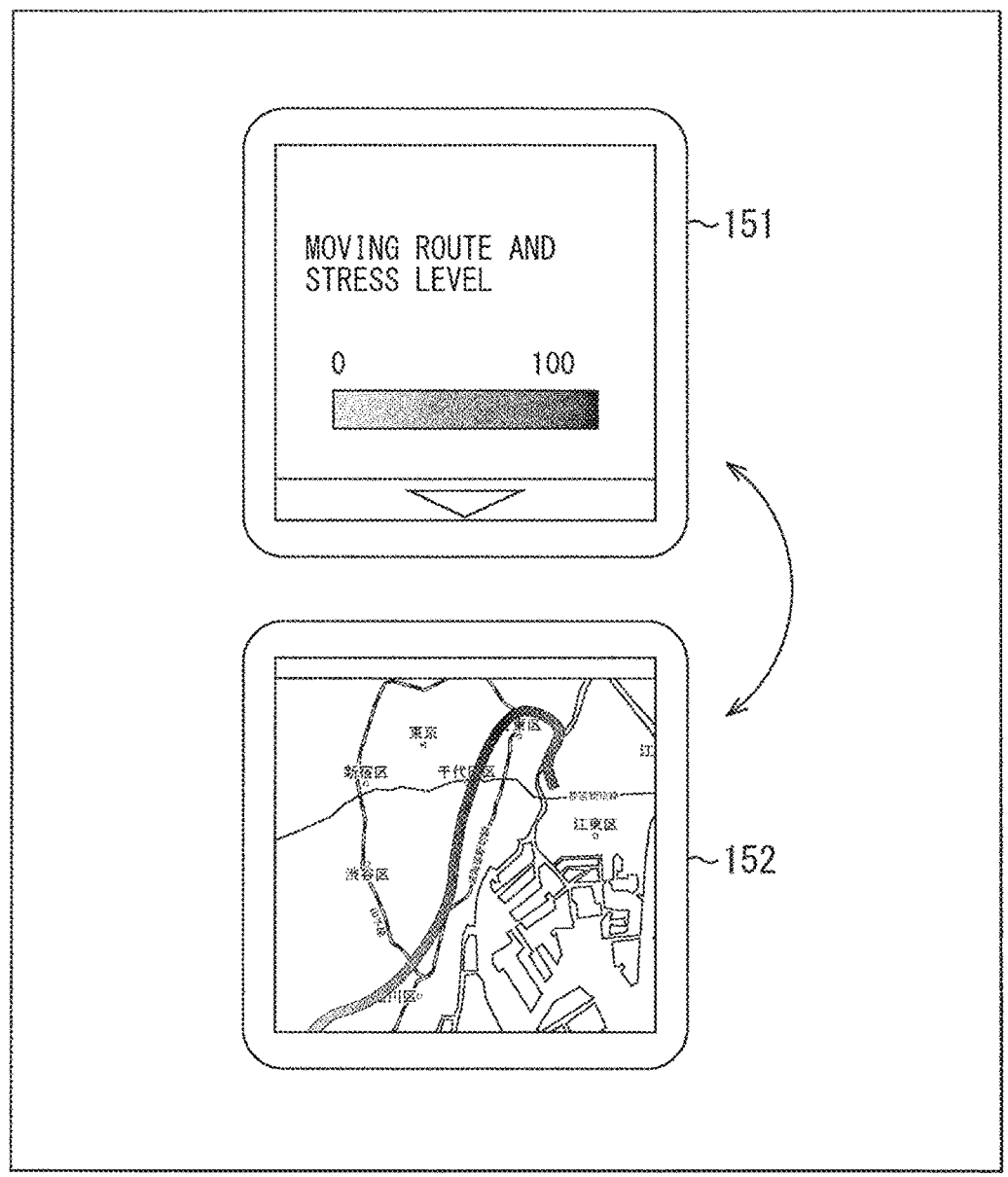
FIG. 14 is a diagram illustrating a third display screen example for the smart watch for presenting the factor causing stress.

FIG. 14 is a diagram illustrating still another display screen example for the smart watch for presenting the factor causing stress.

A display screen for smart watch is divided into a display screen 151 for describing display contents and a display screen 152 representing a relationship between a moving route and the stress level.

The display screen 151 represents contents displayed on the display screen 152, which is "the moving route and the stress level", and gradations representing the stress level. A downward triangle displayed in a lower portion of the display screen 151 represents that transition to the display screen 152 is enabled by upward swiping.

As with the display screen 151, the display screen 152 displays the moving route of the user on the map with colors representing the stress level.

It is also possible for the user to confirm a relationship between the increase or decrease in the stress level and a location as a factor causing the increase or decrease in the stress level even on such a display screen.

<Display Screen Examples for Presenting Result of Analysis of Factor Causing Stress>

For example, in the stress factor specifying unit 34, the factor causing stress is also analyzed. Various screens for presenting a result of analysis of the factor causing stress are displayed by the output controller 36B in response to an operation by the user.

Figure 15B:
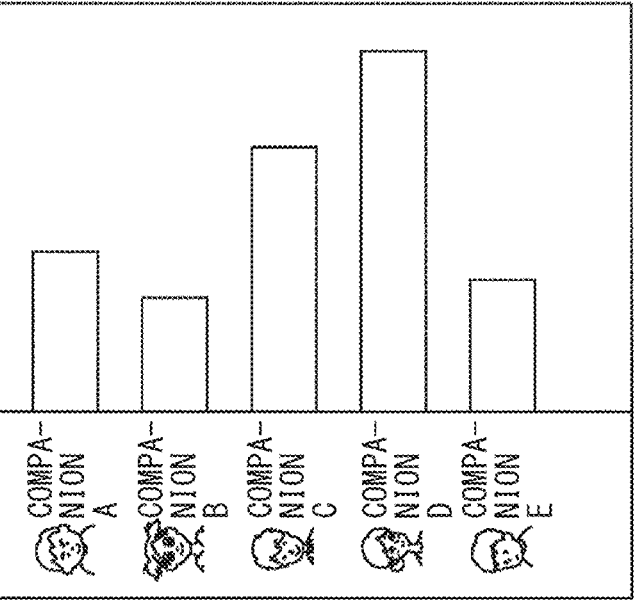
FIGS. 15A and 15B are diagrams illustrating a first display screen example for the smartphone for presenting a result of analysis of the factor causing stress.
Figure 15A:
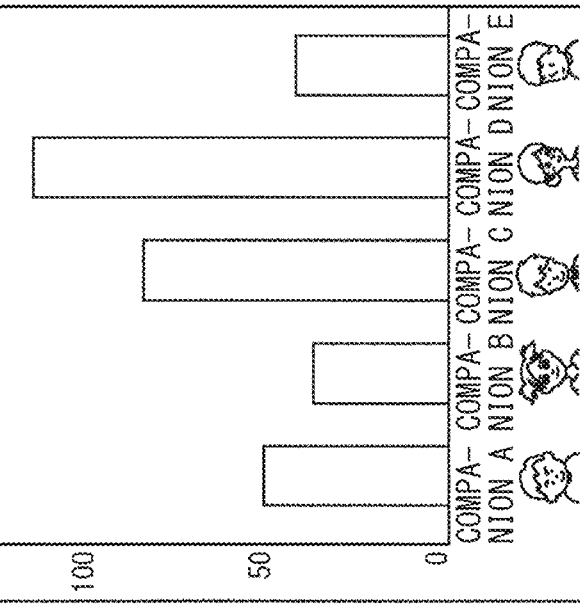

FIGS. 15A and 15B are diagrams illustrating a display screen example for the smartphone for presenting a result of analysis of the factor causing stress.

A display screen 181 in FIG. 15A is a vertical screen presenting a result of analysis of a relationship between companions and the stress level. A bar graph in the vertical direction displayed on the display screen 181 represents a stress level when being with each of companions A to E. That is, the companion who is with the user are considered as a factor, and the display screen 181 is a display screen presenting a relationship between the companion as the factor and the stress level. A white arrow #81 in the horizontal direction represents that displayable items (companions) are switchable by horizontal scrolling.

The stress level when the user (a user of a smartphone) is with the companion A is 50, and the stress level when the user is with the companion B is 40. The stress levels when the user is with other users are also displayed by the bar graph in a similar manner.

Viewing the display screen 181 makes it possible for the user to confirm a relationship between an increase or decrease in the stress level and the companions as the factor causing the increase or decrease in the stress level, such as the stress level of the user being high when the user is with the companion D and being low when the user is with the companion B or E.

A display screen 182 in FIG. 15B is a screen in which the display screen 181 is oriented horizontally. A white arrow #82 in the vertical direction represents that displayable items (companions) are switchable by vertical scrolling.

Figure 16:
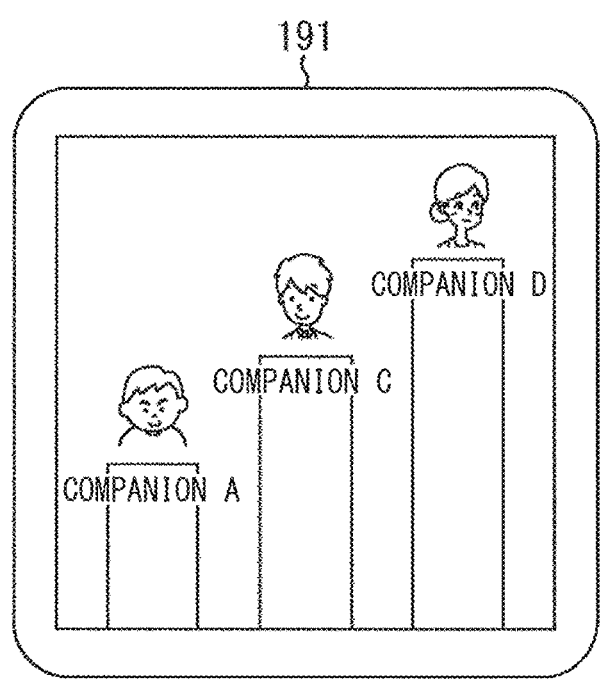
FIG. 16 is a diagram illustrating a first display screen example for the smart watch for presenting a result of analysis of the factor causing stress.

FIG. 16 is a diagram illustrating another display screen example for the smart watch for presenting a result of analysis of the factor causing stress.

A display screen 191 in FIG. 16 is a screen presenting a result of analysis of a relationship between companions and the stress level, as with the display screen 181 in FIGS. 15A and 15B. In an example in FIG. 16, only top three companions who cause a high stress level are displayed.

It is also possible for the user to confirm a result of analysis of a relationship between the increase or decrease in the stress level and the companions as the factor causing the increase or decrease in the stress level even on such a display screen.

Figure 17A:
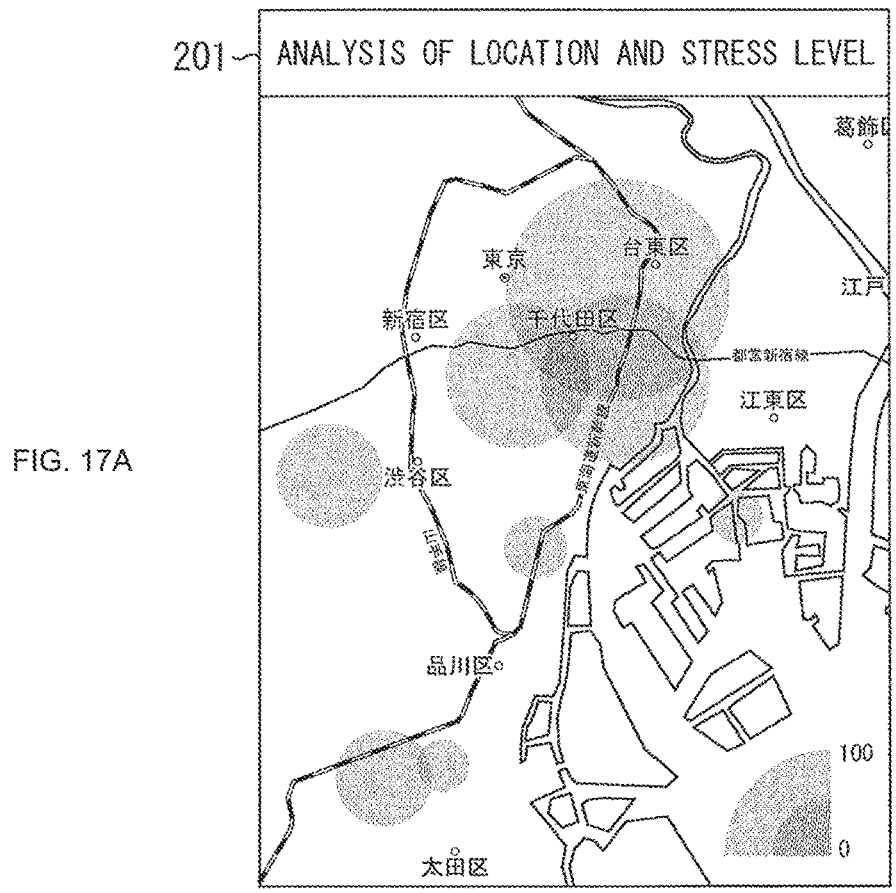
FIGS. 17A and 17B are diagrams illustrating a second display screen example for the smartphone for presenting a result of analysis of the factor causing stress.
Figure 17B:
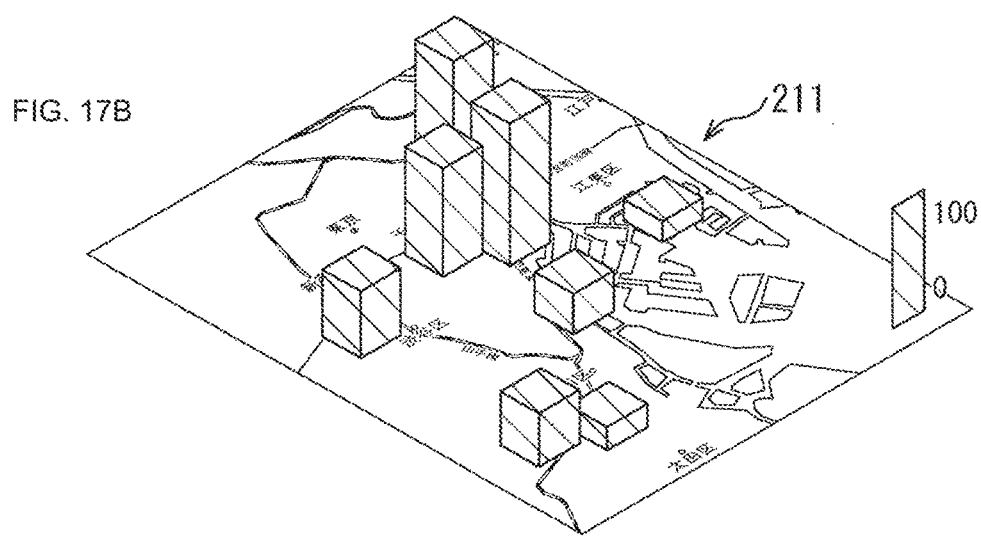

FIGS. 17A and 17B are diagrams illustrating a display screen example for the smartphone for presenting a result of analysis of the factor causing stress.

A display screen 201 in FIG. 17A is a screen presenting a result of analysis of a relationship between a location and the stress level. A map of a predetermined range is displayed on the display screen 201, and an image of a circle centered on each of a plurality of positions is displayed on the map. A size of the circle represents magnitude of the stress level. A degree of the stress level represented by the size of the circle is illustrated at the bottom right of the display screen 201.

The display screen 201 is a screen presenting a relationship between a location (position) as the factor and the stress level. Viewing the display screen 201 makes it possible for the user to confirm the stress level when the user is in each region.

The relationship between each location and the stress level may be represented by a stereoscopic image 211 as illustrated ink FIG. 17B. In the stereoscopic image 211, the stress level at each position on the map is represented by a height of a bar graph in a square prism. As described above, presentation of the stress level is freely changeable.

Figure 18:
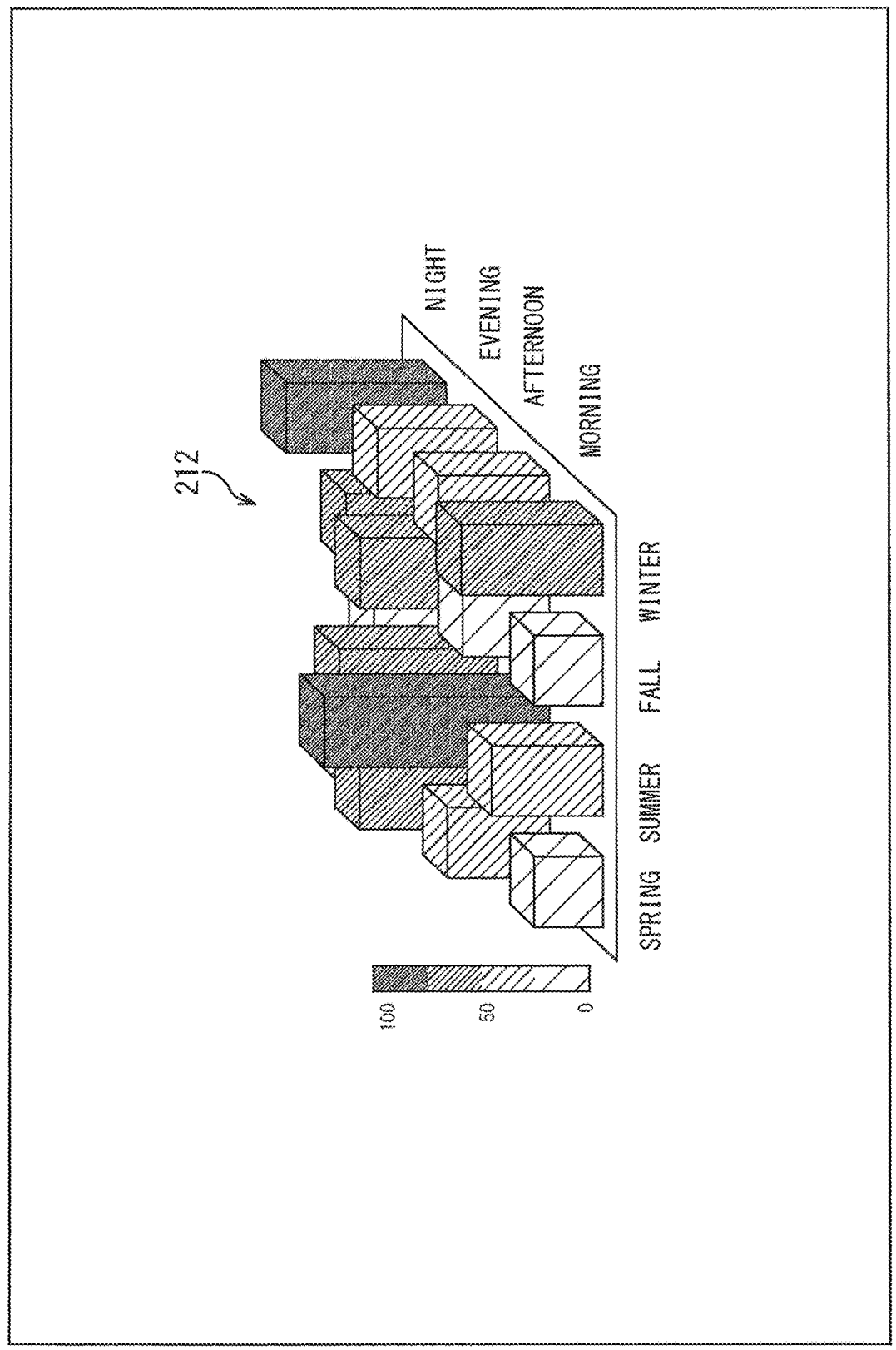
FIG. 18 is a diagram illustrating a third display screen example for the smartphone for presenting a result of analysis of the factor causing stress.

FIG. 18 is a diagram illustrating another display screen example for the smartphone for presenting a result of analysis of the factor causing stress.

A stereoscopic image 212 in FIG. 18 is an image presenting the stress level in each period by a bar graph in a square prism form on a plane. In the bar graph, a horizontal axis represents respective time zones including morning, afternoon, evening, and night, and a vertical axis represents respective seasons including spring, summer, fall, and winter. That is, with use of a predetermined period as a factor, and the stereoscopic image 212 is an image presenting a relationship between the period as the factor and the stress level.

Viewing the stereoscopic image 212 makes it possible for the user to confirm, for example, that heat in afternoon in summer causes the stress level to be increased and cold in morning and night in winter causes the stress level to be increased.

<Other Presentation Examples>

The factor causing stress or a result of analysis of the factor may be presented not only with use of the display unit 15a but also with use of the speaker 15e as a voice. In addition, the factor causing stress or a result of analysis of the factor may be displayed with use of AR. Further, not only presentation of the factor causing stress or the result of analysis of the factor, but also presentation from the factor causing stress is performed with use of the display unit 15a, the speaker 15e, and AR.

Figure 19:
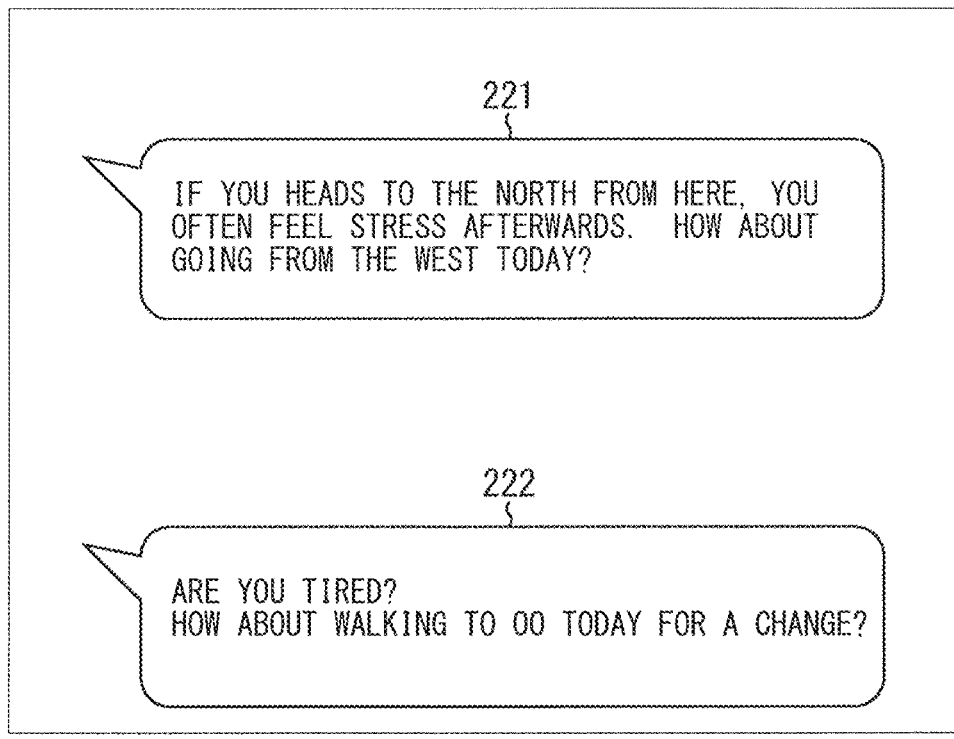
FIG. 19 is a diagram illustrating an examples of a voice output for a suggestion from the factor causing stress.

FIG. 19 is a diagram illustrating an examples of a voice output for a suggestion from the factor causing stress.

An example of a balloon 221 illustrated in an upper stage represents a voice output "If you heads to the north from here, you often feel stress afterwards. How about going from the west today?" The voice output in the balloon 221 suggests a subsequent route on the basis of a relationship between position information and the stress level. Such a suggestion is made in a case where there are a route from the north and a route from the west as a route from a current location to a destination, and there is a region in which the stress level is increased.

For example, when the user starts the navigation app 15c, such a suggestion by voice is outputted by the output controller 36B on the basis of the relationship between the position information and the stress level as described above.

An example in a balloon 222 illustrated in a lower stage represents a voice output "Are you tired? How about walking to 00 today for a change?" The voice output in the balloon 222 suggests a transportation means on the basis of a relationship between activity and the stress level. Such a suggestion is made in a case where there are several transportation means, including walking, from a current location to a destination, and it is specified that the stress level is decreased by taking light exercise.

For example, when the user starts the navigation app 15c, such a suggestion by voice is also outputted by the output controller 36B on the basis of the relationship between activity and the stress level as described above.

Listening to a voice output represented by the balloon 221 or 222 makes it possible for the user to know the stress level of the user and a relieving method.

Figure 20:
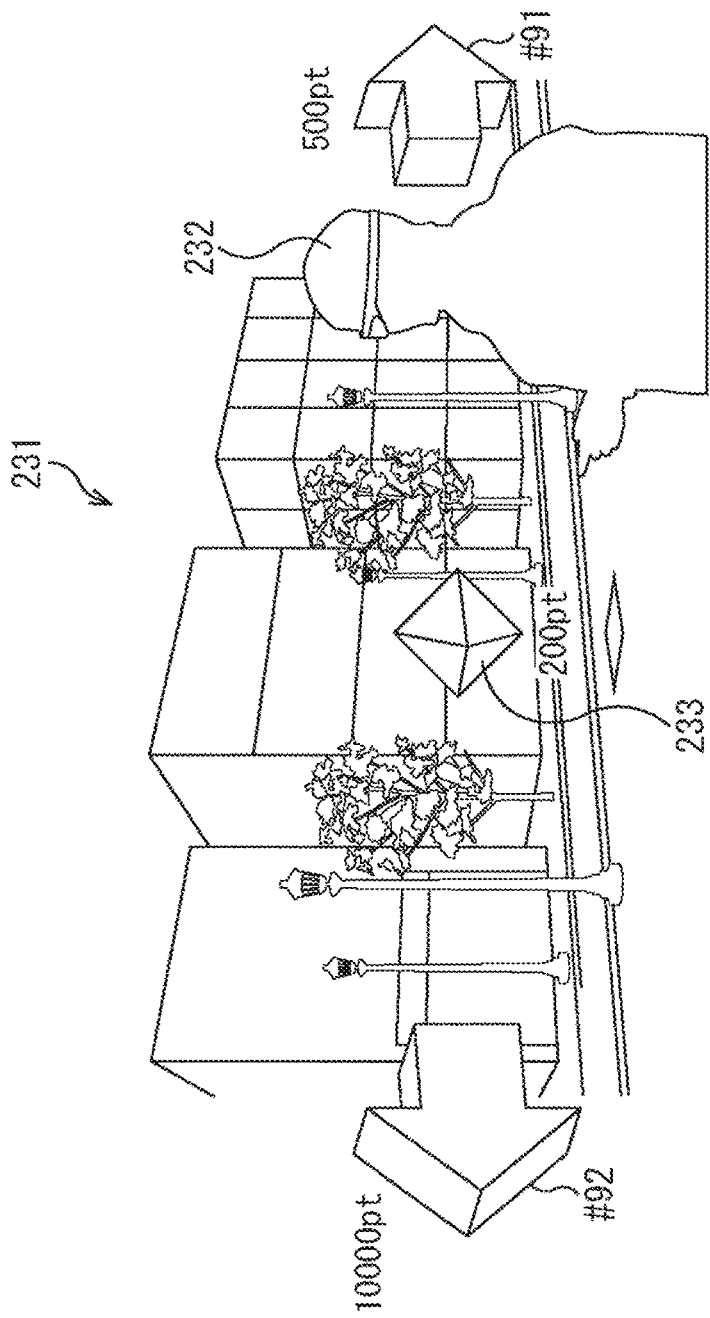
FIG. 20 is a diagram illustrating an example of AR display of a suggestion from the factor causing stress.

FIG. 20 is a diagram illustrating an example of AR display of a suggestion from the factor causing stress.

An AR display screen 231 in FIG. 20 is a screen displayed in a form confirmable by a user 232 when the user 232 wears an eyeglass-type wearable device including the display unit 15a. In a case where the display unit 15a is a transmissive display device, various types of information superimposed on a scene actually viewed by the user 232 are displayed.

In an example in FIG. 20, an object 233 representing that a predicted stress level at that location is 200 pt is displayed in front of the user 232.

An arrow #91 with a value of 500 pt is displayed on the right with reference to the front of the user 232, and an arrow #92 with a value of 10000 pt that is larger than the arrow #91 is displayed on the left. Each of the values attached to respective arrow-shaped objects represents a stress level predicted in a case where the user 232 moves in a direction indicated by the arrow.

The object 233, the arrow #91, and the arrow #92 are displayed with a size corresponding to magnitude of the stress level. For example, when the user starts the navigation app 15c, such a suggestion about the stress level in a case where the user moves in each of such directions is displayed by the output controller 36B on the basis of the relationship between the position information and the stress level as described above.

Viewing such display makes it possible for the user 232 to know the predicted stress level in a case where the user 232 moves in each of the directions.

Figure 21:
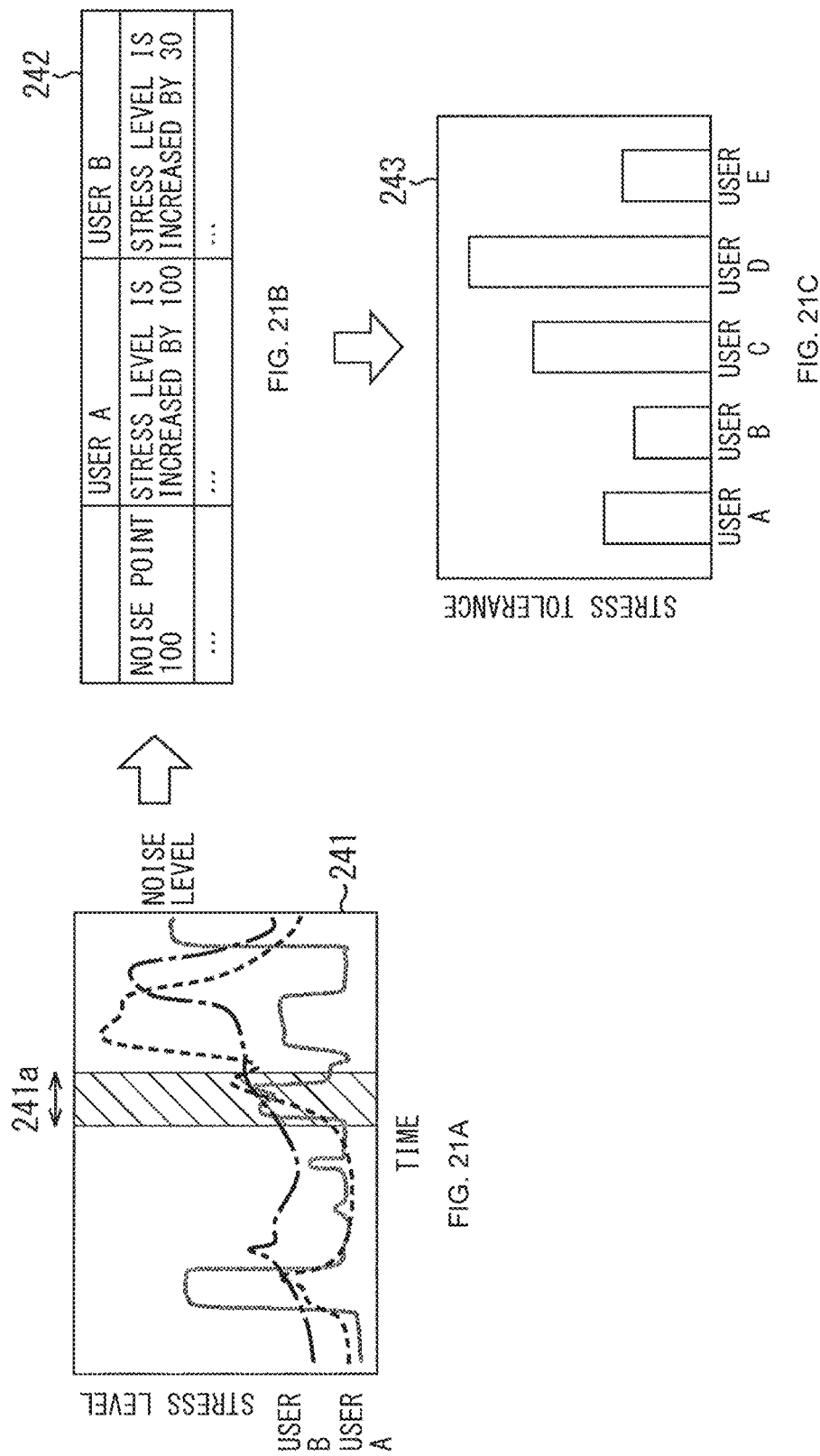
FIGS. 21A, 21B, and 21C are diagrams illustrating a display example of stress tolerance in a group.

FIGS. 21A, 21B, and 21C are diagrams illustrating a display example of stress tolerance in a group.

A display screen 241 in FIG. 21A is a screen representing a stress level of a user A and a stress level of a user B together with a noise level, as with the display screen 121 in FIGS. 11A and 11B. A solid line represents the stress level of the user A, and a dash-dot line represents the stress level of the user B. From the display screen 241, it is possible to confirm that although the stress level of the user A is increased rapidly with an increase in the noise level in a time zone indicated by an arrow 241a, the stress level of the user B is increased only moderately.

A comparison table 242 in FIG. 21B illustrates an increase or decrease in the stress level of each of the users in the time zone indicated by the arrow 241a.

As illustrated in the comparison table 242, the stress level of the user A is increased by 100, while the stress level of the user B is increased by 30.

A comparison graph 243 of relative stress tolerance of each user is generated as illustrated in FIG. 21C by calculating a stress increase degree for each user as illustrated in the comparison table 242. This makes it possible to visualize the relative stress tolerance.

Visualizing the stress tolerance of each user makes it possible for the user to know a user who has high tolerance to noise and a user who has low tolerance to noise.

<Processing Example of Stress Control System>

Hereinafter, an operation of the stress control system 10 having a configuration as described above is described.

First, stress level control processing of the stress control system 10 is described with reference to a flowchart in FIG. 22. Information obtained by the input unit 11 is supplied to the action analyzer 31, the stress level measuring unit 32, and the database 33.

In step S11, the action analyzer 31 analyzes and specifies an action of the user on the basis of the information obtained by the input unit 11.

In step S12, the stress level measuring unit 32 measures an integrated stress level of the user on the basis of the information obtained by the input unit 11.

Information representing the action of the user specified by the action analyzer 31 and information representing the stress level measured by the stress level measuring unit 32 are supplied to the database 33 and the stress level increase/decrease processing unit 36. An action history of the user, the stress level, and measurement data obtained by the input unit 11 are registered in the database 33.

In step S13, the stress factor specifying unit 34 specifies a factor causing an increase or decrease in the stress level on the basis of the information registered in the database 33, as described above.

The stress factor specifying unit 34 takes note of a time when the stress level is decreased, and analyzes an act done by the user and a surrounding situation at that time, which makes it possible to specify an act and a situation that cause the stress level to be decreased. In addition, the stress factor specifying unit 34 takes note of a time when the stress level is increased, and analyzes an act done by the user and a surrounding situation at that time, which makes it possible to specify an act and a situation that cause the stress level to be increased.

In step S14, the stress increase/decrease threshold value specifying unit 35 sets a threshold value for the stress level increase/decrease processing unit 36 for generating an event.

In step S15, the stress level increase/decrease processing unit 36 performs stress level increase/decrease processing, which is processing for increasing or decreasing stress. The stress level increase/decrease processing is described in detail later with reference to a flowchart in FIG. 23.

In step S16, the stress level increase/decrease processing unit 36 determines whether or not to end the stress level control processing. In a case where it is determined not to end the stress level control processing in the step S16, the processing returns to the step S11, and the processing described above is repeated.

In a case where it is determined to end the stress level control processing in the step S16, the stress level control processing is ended.

Figure 22:
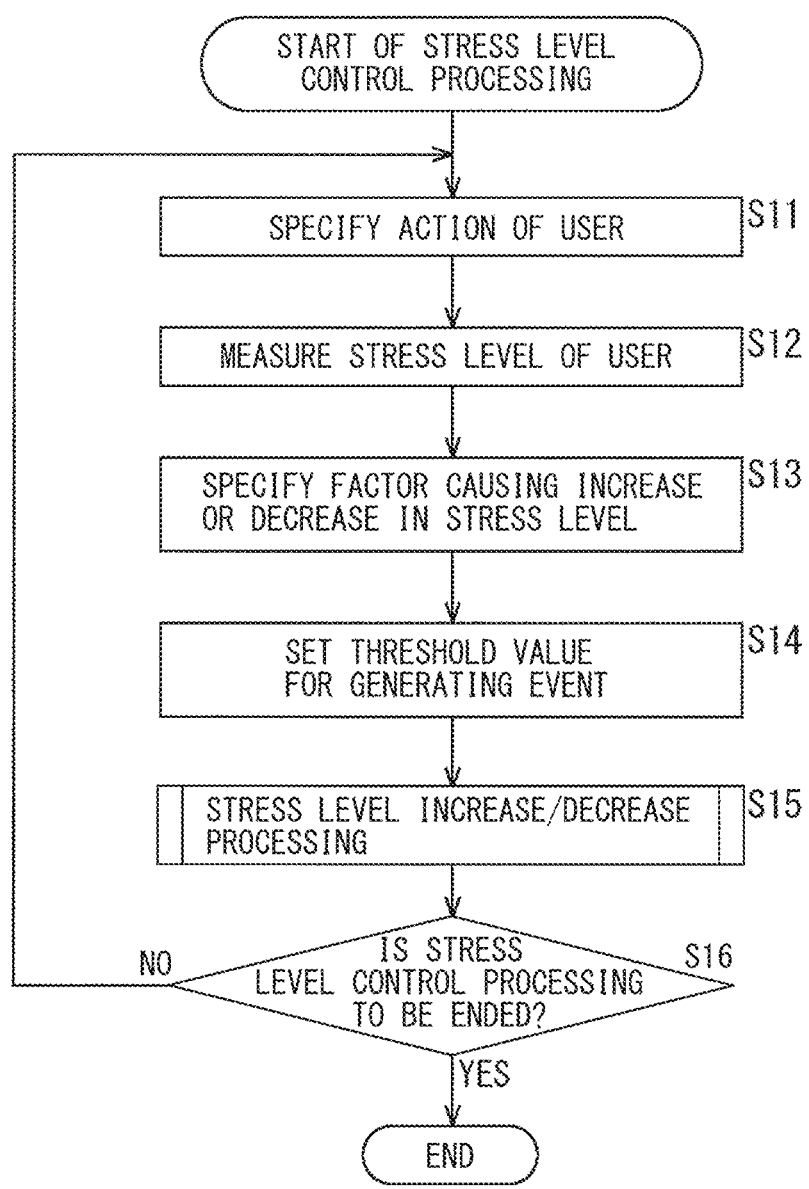
FIG. 22 is a flowchart for describing stress level control processing in the stress control system.
Figure 23:
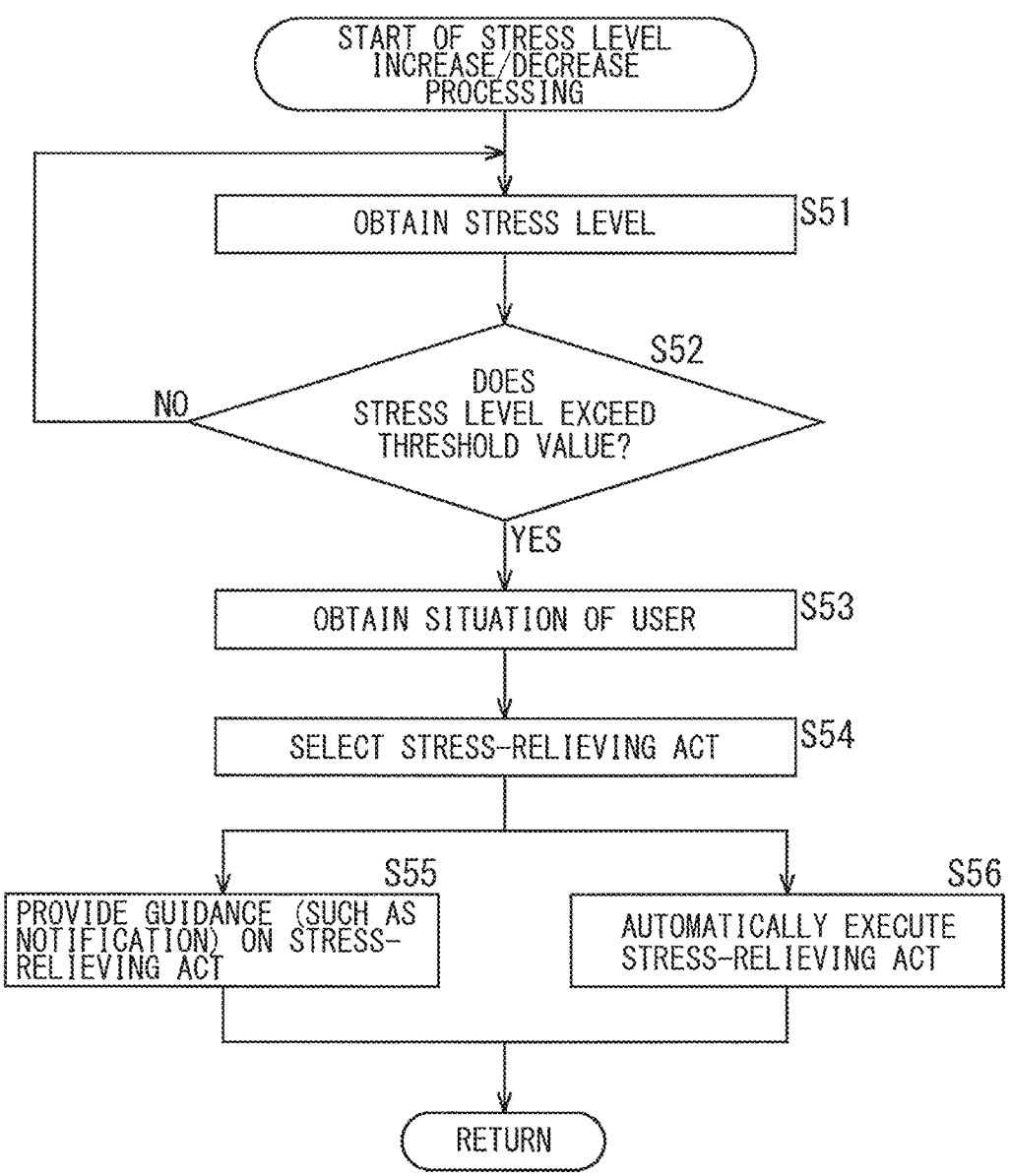
FIG. 23 is a flowchart for describing stress level increase/decrease processing in step S15 of FIG. 22.

Next, the stress level increase/decrease processing performed in the step S15 of FIG. 22 is described with reference to the flowchart in FIG. 23. The processing in FIG. 23 is performed in a case where the stress level that has been increased due to a factor such as many meeting in a company is to be decreased, or the like.

In step S51, the processing controller 36A of the stress level increase/decrease processing unit 36 obtains the stress level of the user measured by the stress level measuring unit 32.

In step S52, the processing controller 36A determines whether or not the stress level of the user exceeds the threshold value, with use of the threshold value set by the stress increase/decrease threshold value specifying unit 35 in the step S14 of FIG. 22.

In a case where it is determined in the step S52 that the stress level of the user does not exceed the threshold value, the processing returns to the step S51, and the processing described above is repeated. In contrast, in a case where it is determined in the step S52 that the stress level of the user exceeds the threshold value, the processing proceeds to step S53.

In the step S53, the processing controller 36A obtains a current situation of the user specified by the action analyzer 31. For example, information such as an action of the user, a location, an application being used by the user, a song being listened to by the user, and a companion is obtained as a current situation.

In step S54, the processing controller 36A selects a stress-relieving act, which is an act of relieving stress. The stress-relieving action is selected on the basis of the factor causing a decrease in the stress level and the current situation of the user.

For example, in a case where listening to a certain music has been specified, in the past, as the factor causing the degrease in the stress level, and it is specified that the user is currently operating the portable terminal 1 capable of playing the music, listening to the same song with use of the portable terminal 1 is selected as a stress-relieving act.

In addition, in a case where smelling an aroma from the aroma lamp 15b has been specified, in the past, as the factor causing the degrease in the stress level, and it is specified that the user is currently in a living room at home, smelling the same aroma with use of the aroma lamp 15b in the living room is selected as a stress-relieving act.

In a case where taking light exercise has been specified, in the past, as the factor causing the degrease in the stress level, and it is specified that the user is currently traveling on foot, traveling along a circuitous route that results in light exercise is selected as the stress-relieving act.

As described above, an action corresponding to the current situation of the user is selected as the stress-relieving act from among the actions of the user specified as the factor causing the degrease in the stress level. For example, an act such as eating something delicious and reading a favorite book is also appropriately selected as a stress-relieving act.

After selecting the stress-relieving act, the processing controller 36A provides guidance on the stress-relieving act in step S55, or automatically executes the stress-relieving act in step S56.

The guidance on the stress-relieving act provided in the step S55 means that the user is suggested to perform the selected stress-relieving act by giving a notification or the like. The notification to the user is performed, for example, by screen display or voice using the output unit 15, as described with reference to FIGS. 19 and 20.

Further, automatic execution of the stress-relieving act performed in the step S56 means that the processing controller 36A automatically executes processing for causing the stress-relieving act to be taken with no operation by the user.

For example, in a case where an act of listening to a certain song with use of the portable terminal 1 is selected as the stress-relieving act, the processing controller 36A displays a screen suggesting listening to the same song upon providing guidance on the stress-relieving act. In addition, in a case where the processing controller 36A automatically executes the stress-relieving act, the processing controller 36A controls the portable terminal 1 to start playing the song.

In addition, in a case where an act of smelling an aroma with use of the aroma lamp 15b is selected as the stress-relieving act, the processing controller 36A displays a screen suggesting smelling the same aroma upon providing guidance on the stress-relieving act. In addition, in a case where the processing controller 36A automatically executes the stress-relieving act, the processing controller controls the aroma lamp 15b included in the output unit 15 to diffuse the aroma.

In a case where an act of traveling along a circuitous route is selected as the stress-relieving act, the processing controller 36A displays a screen suggesting traveling along the circuitous route upon providing guidance on the stress-relieving act. In addition, in a case where the processing controller 36A automatically executes the stress-relieving act, the processing controller 36A controls the navigation app 15*c* included in the output unit 15 to present the circuitous route.

Taking the same act in response to such guidance on the stress-relieving act makes it possible for the user to relieve stress. Even automatically executing the stress-relieving act makes it possible for the user to relieve stress.

Figure 24:
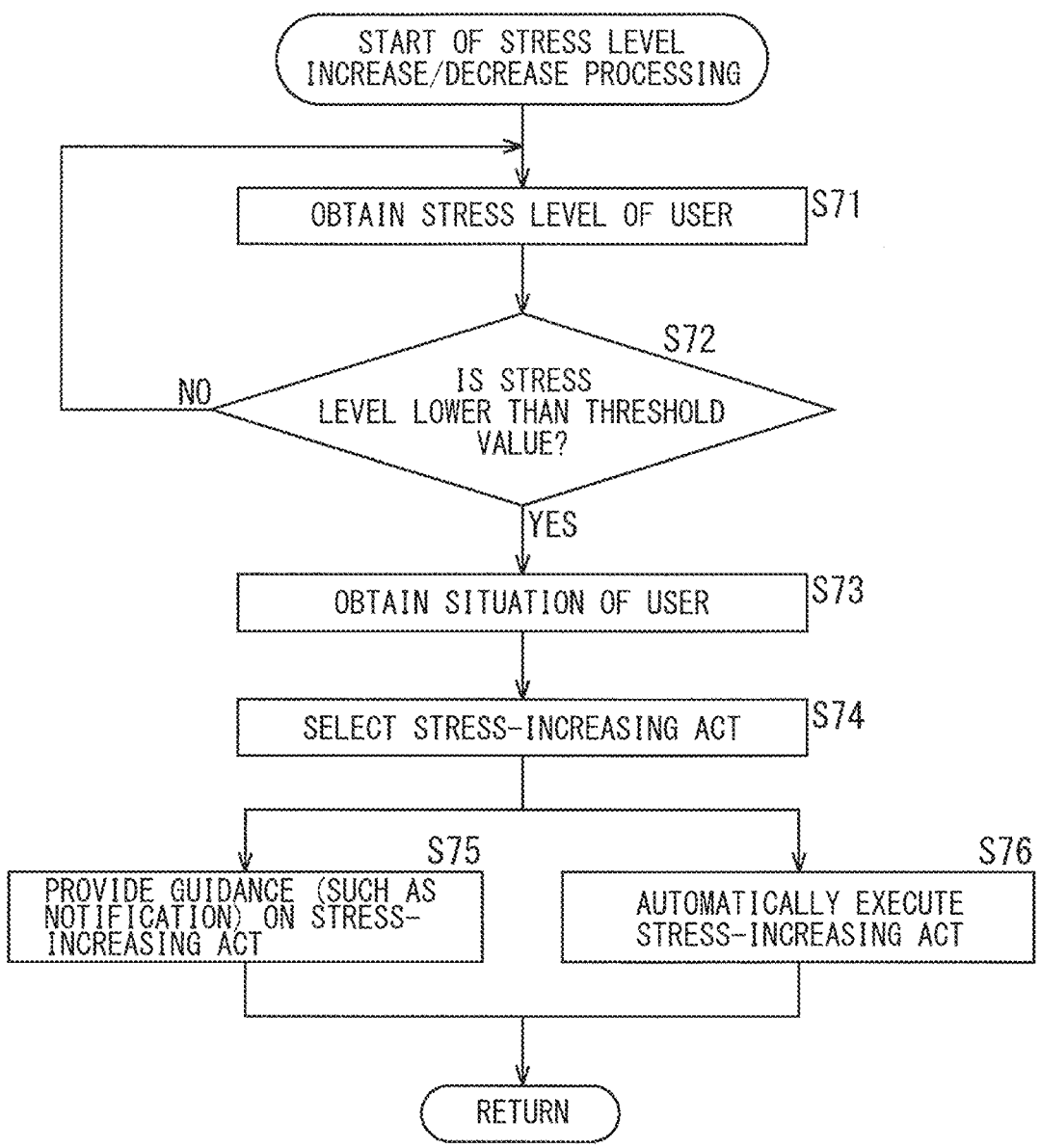
FIG. 24 is a flowchart for describing another example of the stress level increase/decrease processing in the step S15 of FIG. 22.

Next, another stress level increase/decrease processing performed in the step S15 of FIG. 22 is described with reference to a flowchart in FIG. 24. The processing in FIG. 24 is performed at timings before an important meeting, during sports practice, before a sports competition, and the like. At such timings, in some cases, it is preferable to increase the stress level.

In step S71, the processing controller 36A of the stress level increase/decrease processing unit 36 obtains the stress level of the user measured by the stress level measuring unit 32.

In step S72, the processing controller 36A determines whether or not the stress level of the user is lower than the threshold value, with use of the threshold value set in the step S14 of FIG. 22.

In a case where it is determined in the step S72 that the stress level of the user is not lower than the threshold value, the processing returns to the step S71, and the processing described above is repeated. In contrast, in a case where it is determined in the step S72 that the stress level of the user is lower than the threshold value, the processing proceeds to step S73.

In the step S73, the processing controller 36A obtains a current situation of the user specified by the action analyzer 31. For example, information such as an action of the user, a location, an application being used by the user, a song being listened to by the user, and a companion is obtained as the current situation.

In step S74, the processing controller 36A selects a stress-increasing act, which is an act of raising stress. The stress-increasing act is selected on the basis of the factor causing an increase in the stress level and the current situation of the user.

For example, in a case where listening to music that increases a sense of tension or music that maintains the sense of tension has been specified, in the past, as the factor causing the increase in stress level, and it is specified that the user is currently in a living room, listening to the same music in the living room is selected as a stress-increasing act.

In addition, in a case where, in order to increase the stress level of each of students during a lesson in a class room, changing lesson contents and a teaching method has been specified, in the past, as the factor causing the increase in the stress level, and it is specified that the students are currently in class, changing lesson contents and the teaching method in a similar manner is selected as a stress-increasing act.

In a case where, upon traveling on foot to a destination, traveling along a circuitous route or a route including stairs has been specified, in the past, as the factor causing the increase in the stress level, and it is specified that the user is currently traveling on foot, taking a circuitous route or a route including stairs for training is selected as a stress-increasing act.

As described above, an action corresponding to the current situation of the user is selected as the stress-increasing act from among the actions of the user specified as the factor causing the increase in the stress level. For example, an act such as meditation is also appropriately selected as a stress-increasing act.

After selecting the stress-increasing act, the processing controller 36A provides guidance on the stress-increasing act in step S75, or automatically executes the stress-increasing act in step S76.

For example, in a case where an act of listening to a certain song with use of the portable terminal 1 is selected the stress-increasing act, the processing controller 36A displays a screen suggesting listening to the same song upon providing guidance on the stress-increasing act. In addition, in a case where the processing controller 36A automatically executes the stress-increasing act, the processing controller 36A controls the portable terminal 1 to start playing the song.

In addition, in a case where an act of changing lesson contents or a teaching method in a similar manner is selected as the stress-increasing act, the processing controller 36A displays a screen suggesting a teacher changing the lesson contents or the teaching method upon providing guidance on the stress-increasing act. In addition, in a case where the processing controller 36A automatically executes the stress-increasing act, the processing controller 36A controls the display unit 15*a* included in the output unit 15 to present a lesson suitable to a student.

In a case where taking a circuitous route or a route including stairs is selected as the stress-increasing act, the processing controller 36A displays a screen suggesting traveling along the circuitous route or the route including the stairs. In addition, in a case where the processing controller 36A automatically executes the stress-relieving act, the processing controller 36A controls the navigation app 15*c* included in the output unit 15 to present the circuitous route.

Taking the same act in response to such guidance on the stress-increasing act makes it possible for the user to increase and maintain stress. Even automatically executing the stress-increasing act makes it possible for the user to increase and maintain stress.

As described above, in a case where the stress level is high, the user is caused to perform a stress-relieving act, and in a case where the stress level is low, the user is caused to perform a stress-increasing act, which makes it possible to keep the stress level of the user to a predetermined level.

<Specific Presentation Examples>

Specific examples of the stress-relieving act are described. Here, specific examples of the stress-relieving act are described, but the stress-increasing act is also defined in a similar manner.

FIG. 25 is a diagram illustrating a specific example of the stress-relieving act on a holiday. In a rightmost column, examples of the stress-relieving act itself, or examples of presentation of the stress-relieving act are illustrated.

Three examples of the stress-relieving act in a case where the stress level is high because "the user wanted to sleep a little longer, but was woken up by a family" at 8:00 a.m. on awakening are as follows.

"Diffuse a favorite aroma"

"Play favorite music or a favorite television program"

"Refresh by taking a dog walk"

Two examples as the stress-relieving acts or presentation examples of the stress-relieving act in a case where the stress level is high because "the user wants to go shopping but has to clean up" in a morning action are as follows.

"Get involved in cleaning by playing music suitable for a simple task"

"Suggest drinking coffee after cleaning"

Four examples as the stress-relieving acts or presentation example of the stress-relieving act in a case where the stress level is high because "the user is going to lunch with relatives who do not get along with the user for a social reason" in lunch are as follows.

"Present a dish that is favorite and allows stress to be relieved"

"If a friend who gets along with the user is in a neighborhood, present drinking coffee with the friend after lunch"

"Present walking home and making a stop at a relaxing place"

"Suggest napping"

Three examples as the stress-relieving act or presentation examples of the stress-relieving act in a case where the stress level is high because "the user wants to have a nap, but is asked to go shopping" in an afternoon action are as follows.

"Play favorite music during traveling for shopping"

"Suggest going to a shop that is even a little enjoyable for the user"

"Suggest buying sweets and coffee for a break after shopping."

Two examples as presentation examples of the stress-relieving act in a case where the stress level is high because "the user wants to watch a favorite television program, but a child takes over a television" in a nighttime action.

"Display contents that are enjoyable for children and adults to family"

"Suggest a game or the like that is enjoyable for family"

FIGS. 26 to 29 are diagrams illustrating specific examples of the stress-relieving act on a weekday.

FIG. 26 illustrates the stress-relieving act at 6:00 a.m. on awakening and the stress-relieving act during commute.

Three examples as the stress-relieving acts in a case where the stress level is high because of "a sleep duration was short because of work" at 6:00 a.m. on awakening are as follows.

"Diffuse a favorite aroma"

"Play favorite music"

"Show a favorite television program"

In a case of "diffuse a favorite aroma", it is determined that the stress level exceeds the threshold value in a case where a pulse meter of a smart watch detects that stress is higher than usual. A situation of the user is obtained by recognizing where the user is by a camera or the like at home. In a case where it is recognized that the user is in a bedroom, a process of "diffusing a favorite aroma" is automatically executed in the bedroom on the basis of past data.

In a case of "play favorite music", it is determined that the stress level exceeds the threshold value in a case where a pulse meter of a smart watch detects that stress is higher than usual. A situation of the user is obtained by recognizing where the user is by a camera or the like at home. In a case where it is recognized that the user is in a living room, a process of "playing favorite music" is automatically executed in the living room on the basis of past data.

In a case of "show a favorite television program", it is determined that the stress level exceeds the threshold value in a case where a pulse meter of a smart watch detects that stress is higher than usual. A situation of the user is obtained by recognizing where the user is by a camera or the like at home. In a case where it is recognized that the user is in a living room, a process of "showing a favorite television program" is automatically executed in the living room on the basis of past data.

Two examples as presentation examples of the stress-relieving act in a case where the stress level is high because "a train is more crowded than usual due to a train delay" during commute are as follows.

"Present a favorite television program on a smartphone"

"Present walking to an office while relieving stress by light exercise, because it is found that it does not take long even if the user walks to the office"

In a case of "present a favorite television program on a smartphone", it is determined that the stress level exceeds the threshold value in a case where a pulse meter of a smart watch detects that stress is higher than usual. A situation of the user is obtained by recognizing that the user is riding on a train by a GPS or an accelerometer of the smartphone, recognizing that the train is crowded from information of a train company, and recognizing that the user is allowed to operate the smartphone by an opened screen of the smartphone. At this time, stress-relieving acts that are executable with use of the smartphone are listed from past data, and, for example, the user is notified of watching a favorite television program, which is considered to have the greatest effect, on the smartphone.

In a case of "present walking to an office while relieving stress by light exercise, because it is found that it does not takes long even if the user walks to the office", it is determined that the stress level exceeds the threshold value in a case where a pulse meter of a smart watch detects that stress is higher than usual. A situation of the user is obtained by recognizing that the user is riding on a train by a GPS or an accelerometer of the smartphone, recognizing that the train is crowded from information of a train company, and recognizing that it is possible to walk to the office from position information and a schedule table. At this time, it is known from past data that walking decreases stress; therefore, the user is notified by the smartphone to walk to the office.

FIG. 27 illustrates the stress-relieving act during work in the morning.

Three examples as the stress-relieving acts or presentation examples of the stress-relieving act in a case where the stress level is high because "works close to deadlines are piled up" during work in the morning are as follows.

"Get involved in work while playing favorite music"

"Present asking a question about work to someone who gets along with the user"

"Present delivering a submission using stairs"

In a case of "get involved in work while playing favorite music", it is determined that the stress level exceeds the threshold value in a case where a pulse meter of a smart watch detects that stress is higher than usual. A situation of the user is obtained by recognizing that no one is around by a microphone of the smartphone, and recognizing that works are piled up from a schedule table. At this time, it is known from past data that it is possible to concentrate when the favorite music is played, therefore, a process of playing the favorite music is automatically executed.

In a case of "present asking a question about work to someone who gets along with the user", it is determined that the stress level exceeds the threshold value in a case where a pulse meter of a smart watch detects that stress is higher than usual. A situation of the user is obtained by recognizing that a PC is open, but writing is not performed frequently, or browser research is conducted. At this time, a screen suggesting asking a question to a friend who gets along with the user is displayed on the PC.

In a case of "present delivering submissions using stairs", it is determined that the stress level exceeds the threshold value in a case where a pulse meter of a smart watch detects that stress is higher than usual. A situation of the user is obtained by recognizing that there is a submission from the schedule table. At this time, it is known from past data that taking exercise decreases stress; therefore, a screen suggesting delivering the submission on foot is displayed on the smart watch at a timing of getting up from a seat.

FIG. 28 illustrates the stress-relieving act at lunch.

Four examples as presentation examples for decreasing the stress level in a case where the stress level is high because of "lunch with a troublesome client" at lunch are as follows.

"Present a dish that is favorite and allows stress to be relieved"

"If a friend who gets along with the user is in a neighborhood, present drinking coffee with the friend after lunch"

"Present walking to home and making a stop at a relaxing place"

"Suggest napping"

In a case of "present a dish that is favorite and allows stress to be relieved", it is determined that the stress level exceeds the threshold value in a case where an increase in stress is predicted from the schedule table. A situation of the user is obtained by recognizing a meeting with a troublesome client from the schedule table. It is predicted from past data that the client is troublesome. At this time, it is known that eating a favorite dish decreases stress; therefore, a restaurant is contacted regarding a favorite menu, and the user is notified that the favorite menu is present.

In a case of "if a friend who gets along with the user is in a neighborhood, present drinking coffee with the friend after lunch", it is determined that the stress level exceeds the threshold value in a case where a pulse meter of a smart watch detects that stress is higher than usual. A situation of the user is obtained by recognizing that the friend is in a neighborhood from position information of the user and the friend measured by the GPS of the smartphone. At this time, it is known from past data that speaking with the friend decreases stress; therefore, upon leaving the restaurant, if the user has spare time in the schedule table, the user is notified by the smartphone to meet the friend.

In a case of "present walking to home and making a stop at a relaxing place", it is determined that the stress level exceeds the threshold value in a case where a pulse meter of a smart watch detects that stress is higher than usual. A situation of the user is obtained by recognizing the position information by the GPS of the smartphone. At this time, if the user has spare time in the schedule table, the smartphone displays a screen suggesting going to a relaxing place.

In a case of "suggest napping", it is determined that the stress level exceeds the threshold value in a case where a pulse meter of a smart watch detects that stress is higher than usual. A situation of the user is obtained by recognizing position information by the GPS of the smartphone. At this time, if the user has spare time in the schedule table, it is recommended to have a nap.

FIG. 29 illustrates the stress-relieving act at work in the afternoon.

Three examples as stress-relieving acts in a case where the stress level is high because of "a meeting with a troublesome superior" at work in the afternoon.

"Diffuse a favorite aroma before the meeting"

"Have a meeting with a colleague who gets along with the user before the meeting"

"If the user is ready for the meeting, let the user do another task to forget the meeting"

In a case of "diffuse a favorite aroma before the meeting", it is determined that the stress level exceeds the threshold value in a case where an increase in stress is predicted from the schedule table. A situation of the user is obtained by recognizing from the schedule table that there is a meeting with a troublesome superior, and recognizing position information by the GPS of the smartphone. It is predicted from past data that the superior is troublesome. At this time, it is known from past data that diffusing a favorite aroma decreases stress; therefore, in a case where it is recognized that no other person is around on the basis of a result of detection by the microphone or the like, a process of diffusing a favorite aroma is automatically executed.

In a case of "have a meeting with a colleague who gets along with the user before the meeting", it is determined that the stress level exceeds the threshold value in a case where an increase in stress is predicted from the schedule table. A situation of the user is obtained by recognizing from the schedule table that the user has spare time before the meeting with the troublesome superior. At this time, it is known that talking with a colleague who gets along with the user decreases stress; therefore, the user is notified to have a meeting with the colleague who gets along with the user before the meeting with the troublesome superior.

In a case of "if the user is ready for the meeting, let the user do another task to forget the meeting", a situation of the user is obtained by recognizing from the schedule table that the user has spare time before the meeting with the troublesome superior. Further, the situation of the user is obtained by recognizing that the user is ready for the meeting from the progress of creation of materials and a self-talk such as "finally finished". At this time, it is known from past data that concentration decreases stress; therefore, in a case where it is recognized from the schedule table that the user has spare time before the meeting with the troublesome superior, a process for letting the user do a task, such as highlighting a task registered in a To Do List, is automatically executed.

As described above, in the present technology, the factor causing stress is specified, which makes it possible to effectively control the stress level on the basis of the specified factor.

It is possible to perform control of the stress level depending on circumstances, such as a case where it is desired to relieve stress or a case where stress is increased to a certain level and kept at the certain level.

It is possible not only to use the control for control of a stress level of the individual, but also to use the control for control of stress of a group.

<Specific Configuration Examples of Stress Level Increase/Decrease Processing Unit>

Here, a high stress level is prone to sleep deprivation. Conversely, in a sleep deprivation state, even the same factor may further increase stress. In addition, sleep deprivation itself may be a factor causing stress. In contrast, sufficient sleep decreases the stress level. Accordingly, stress and sleep are related to each other.

Next, description is given of a method of controlling a stress level by optimizing sleep.

Figure 30:
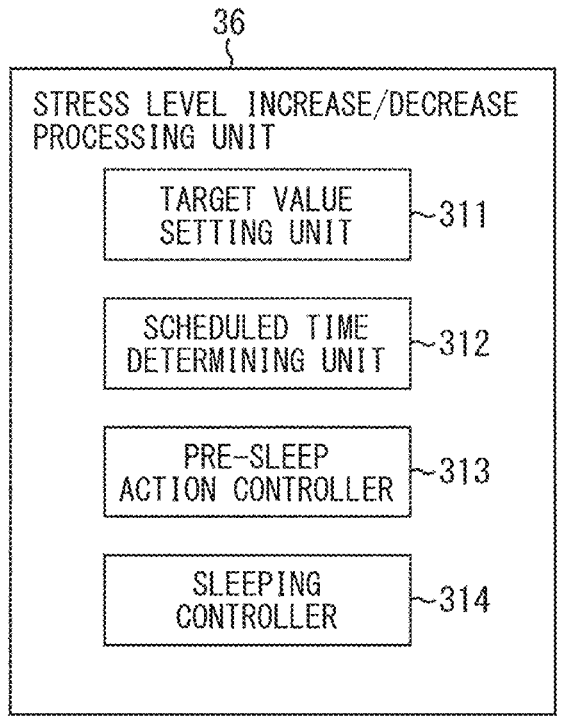
FIG. 30 is a block diagram illustrating a specific configuration example of a stress level increase/decrease processing unit in a case where sleep is optimized.

FIG. 30 is a block diagram illustrating a detailed configuration example of the stress level increase/decrease processing unit 36 in a case where sleep is optimized.

The stress level increase/decrease processing unit 36 includes a target value setting unit 311, a scheduled time determining unit 312, a pre-sleep action controller 313, and a sleeping controller 314.

The target value setting unit 311 sets a sleep quality target value. A sleep quality target value $Q\_s0$ is represented by the following expression (4) with use of the stress level.

[Expression 4]

$$Q\_s0 = S\_1 - S\_2 \qquad (4)$$

$S\_1$ is a stress level at bedtime. As $S\_1$, a stress level one hour before bedtime may be used.

$S\_2$ is a stress level at a wake-up time. Actually, $S\_2$ is a target value of the stress level at a wake-up time. As $S\_2$, a stress level one hour after awakening may be used.

The expression (4) defines sleep quality to become positive in a case where sleep decreases the stress level ($S\_2 < S\_1$).

It is possible to measure the stress level by the methods described above. It is also possible to measure an improvement (or a decline) in the stress level by sleep by performing comparison between the stress levels at daily bedtime and at a daily wake-up time of an individual.

Thus, the target value setting unit 311 sets the sleep quality target value $Q\_s0$ with use of the stress level at bedtime and the stress level at the wake-up time.

The scheduled time determining unit 312 obtains information of a schedule and a lifestyle pattern after wake-up, and determines a scheduled wake-up time according to the schedule after wake-up. For example, in a case where there are plans to go to a company at 7 o'clock as a schedule after wake-up, and the lifestyle pattern is a pattern in which it takes one hour to get ready in the morning, 6 o'clock, which is one hour before 7 o'clock, is determined as a scheduled wake-up time.

The scheduled time determining unit 312 calculates an optimal sleep duration with use of measurement data from the input unit 11. The optimal sleep duration is set, by estimating sleep quality, for example, as a duration that allows quality as a reference to be secured.

It is possible to quantify the sleep quality from various measurement data during sleep by accumulating and analyzing daily data including a combination of the various measurement data during sleep and a change in the stress level by sleep.

The measurement data includes bedtime, sleep-onset time, a wake-up time, a sleep duration, and a duration from going to bed to sleep onset. In addition, the measurement data includes biological information during sleep, such as body motion, pulse, respiration, a body temperature, and eye movement. The measurement data also includes environmental information such as a temperature and humidity in the bedclothes, and a temperature, humidity, noise, brightness, and a smell in a bedroom.

These measurement data are obtained from various sensors of the input unit 11. The input unit 11 may include a wearable device having a variety of sensors, and may obtain measurement data from a life log and the like obtained from the wearable device.

Assuming that various types of measurement data are $\{x\_i\}$ ($i=1, n$), the sleep quality $Q\_s$ is represented by the following expression (5). An algorithm F for estimating the sleep quality $Q\_s$ from $\{x\_i\}$ is determined by machine learning or a statistical technique.

[Expression 5]

$$Q\_s = F(\{x\_i\}) + \delta \qquad (5)$$

$\delta$ is an error associated with estimation. A large number of sets of measurement data $\{x\_i\}$ and the sleep quality $Q\_s$ are used to determine the algorithm F that allows $\delta$ to be as small as possible. In a case where the algorithm F is determined, it is possible to estimate the sleep quality $Q\_s$ with use of newly obtained (or assumed) measurement data $\{x\_i\}$.

A method of analyzing the sleep quality may be machine learning, or may be a statistical technique such as factor analysis or principal component analysis, or covariance structure analysis.

In the sleep quality, it is possible to define sleep that decreases the stress level as higher-quality sleep. For example, falling asleep quickly, sleeping sufficiently deeply, and waking up at a timing during a light sleep in a morning result in higher sleep quality and a low stress level after wake-up as compared with a stress level in a previous night.

The scheduled time determining unit 312 estimates such high-quality sleep and calculate an optimal sleep duration.

In addition, the scheduled time determining unit 312 determines a scheduled bedtime on the basis of the determined scheduled wake-up time and the calculated optimal sleep duration.

The pre-sleep action controller 313 makes presentation for advising an action of the user before sleep. In a case where the stress level is high before bedtime, in order to decrease the stress level on the following day, the pre-sleep action controller 313 may prompt an early sleep to obtain a sufficient sleep duration by presentation or the like.

In order to quickly fall asleep, the pre-sleep action controller 313 recommends not to use a television, a smartphone, a personal computer, and a gaming machine from one hour before the scheduled bedtime, or turns off these devices from one hour before the scheduled bedtime. The pre-sleep action controller 313 adjusts an environment before bedtime such as reducing brightness of a room light, playing music, or preparing a calm environment with an aroma scent, or the like.

The sleeping controller 314 observes a temperature and humidity in a room, a temperature and humidity in bedclothes, and the like during sleep, and adjusts an environment during sleep to achieve high-quality sleep.

The sleeping controller 314 performs a process for waking the user up at an optimal timing closest to the scheduled wake-up time of that day on the basis of body motion and a sleeping pattern. Upon wake-up, a method that is least likely to increase the stress level is used according to preferences of the user. For example, at least one of methods such as gradually increasing brightness of a room light, playing favorite music of the user, gradually increasing the volume of music, diffusing an aroma or incense, and shaking is used as an optimal wake-up method.

<Example of Stress Level Increase/decrease Processing>

Next, the stress level increase/decrease processing by optimization of sleep is described with reference to a flowchart in FIG. 31.

In step S311, the target value setting unit 311 performs target value setting processing, which is processing for setting the target value $Q\_s0$. The target value setting processing is described later with reference to a flowchart in FIG. 33.

In step S312, the scheduled time determining unit 312 performs scheduled time determination processing, which is processing for determining a scheduled bedtime and a scheduled wake-up time. The scheduled time determination processing is described later with reference to a flowchart in FIG. 34.

In step S313, the pre-sleep action controller 313 provides advice on an action before sleep and performs the above-described processing for adjusting an environment before sleep.

Figure 32:
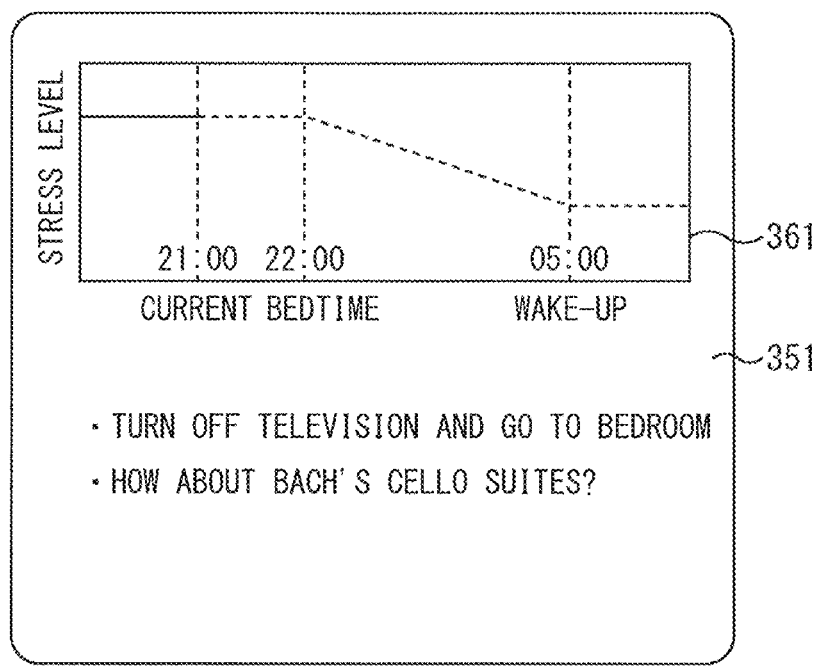
FIG. 32 is a display screen example presented to a user before sleep.

FIG. 32 is a diagram illustrating an example of a display screen presented to the user before sleep.

A stress level transition table 361 displayed in an upper portion of a display screen 351 is an image visualizing transition of the stress level at a current time, a scheduled bedtime, and a scheduled wake-up time as a graph. Viewing the stress level transition table 361 makes it possible for the user to know transitions of the stress level in a case of having a sleep as suggested.

A depth of sleep may also be graphically visualized. In addition, comfort at sleep onset, during sleep, at wake-up may be graphically visualized.

Below the stress level transition table 361, messages are displayed to advise an action before bedtime, such as "Turn off a television and go to a bedroom" and "How about Bach's cello suites?". Such advice may be provided by a voice output.

In step S314, the sleeping controller 314 performs sleeping environment adjustment processing. The sleeping environment adjustment processing includes measurement of a sleep state, adjustment of a sleep environment, and processing for waking the user up at an optimal timing. The sleeping environment adjustment processing is described later with reference to a flowchart in FIG. 36.

After the sleeping environment adjustment processing, the stress level increase/decrease processing by optimization of sleep is ended.

Figure 31:
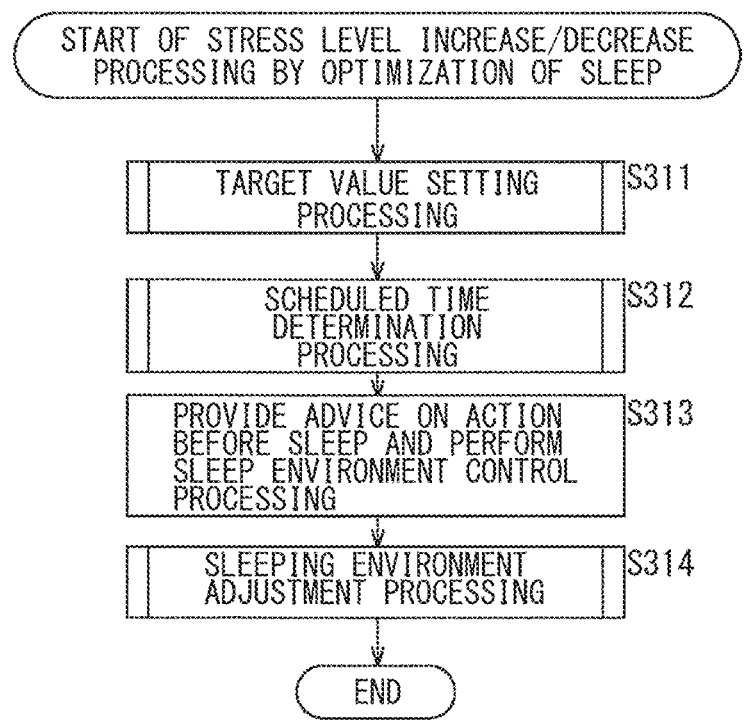
FIG. 31 is a flowchart for describing stress level increase/decrease processing by optimization of sleep.
Figure 33:
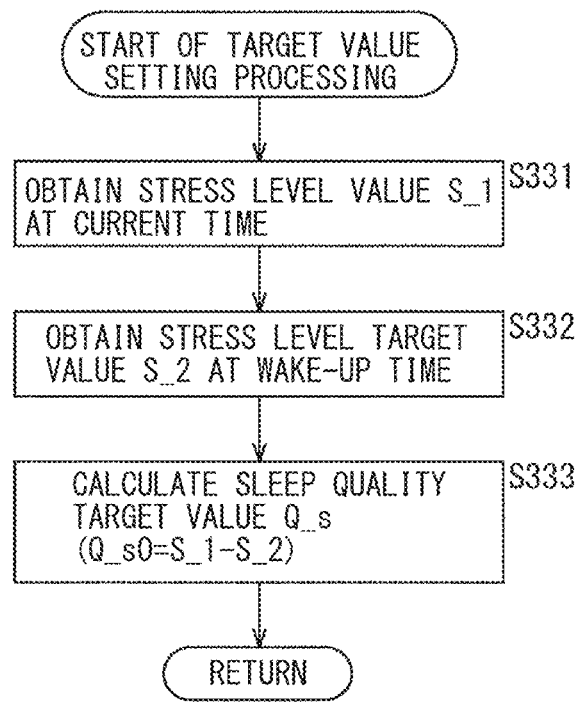
FIG. 33 is a flowchart for describing target value setting processing performed in step S311 of FIG. 31.

Next, the target value setting processing performed in the step S311 of FIG. 31 is described with reference to the flowchart in FIG. 33.

In step S331, the target value setting unit 311 obtains a stress level $S\_1$ at a current time.

In step S332, the target value setting unit 311 obtains a stress level target value $S\_2$ at a wake-up time.

In step S333, the target value setting unit 311 calculates the sleep quality target value $Q\_s0$ from a difference between the stress level $S\_1$ and the stress level target value $S\_2$, as described with reference to the above expression (4).

After the processing in the step S333, the processing returns to the step S311 of FIG. 31, and processing after the step S311 is performed.

Next, the scheduled time determination processing performed in the step S312 of FIG. 31 is described with reference to the flowchart in FIG. 34.

In step S351, the scheduled time determining unit 312 obtains, from the database 33, information of a schedule and a lifestyle pattern after the user wakes up. In the database 33, these information are stored as user information. The user information may be obtained from utterances of the user detected with use of the microphone 11b.

In step S352, the scheduled time determining unit 312 sets a scheduled wake-up time according to the schedule after wake-up and the like.

In step S353, the scheduled time determining unit 312 performs sleep duration calculation processing. The sleep duration calculation processing is described in detail later with reference to the flowchart in FIG. 35.

In step S354, the scheduled time determining unit 312 determines a scheduled bedtime from the scheduled wake-up time set in the step S352 and the optimal sleep duration calculated in the step S353.

After processing in the step S354, the processing returns to the step S312 of FIG. 31, and processing after the step S312 is performed.

Figure 34:
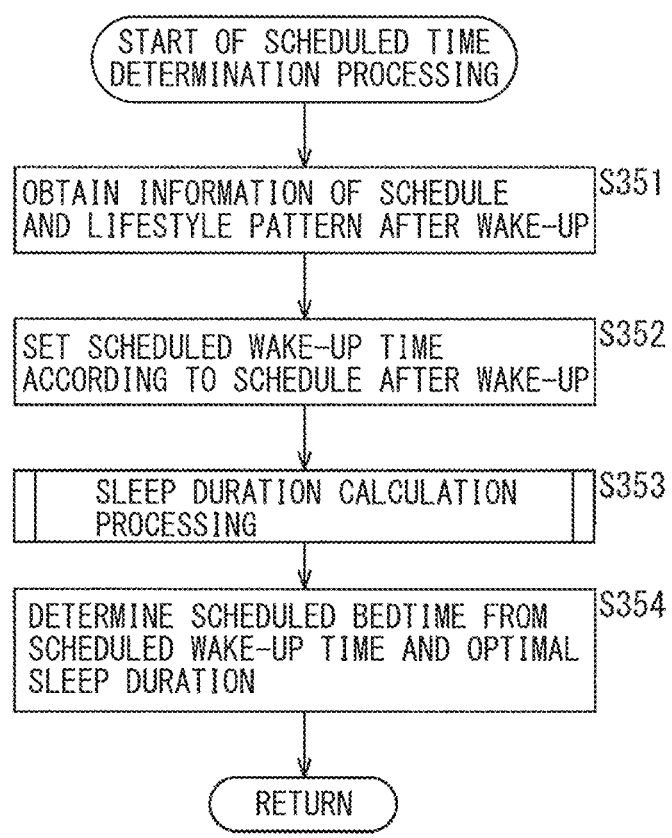
FIG. 34 is a flowchart for describing scheduled time determination processing performed in step S312 of FIG. 31.
Figure 35:
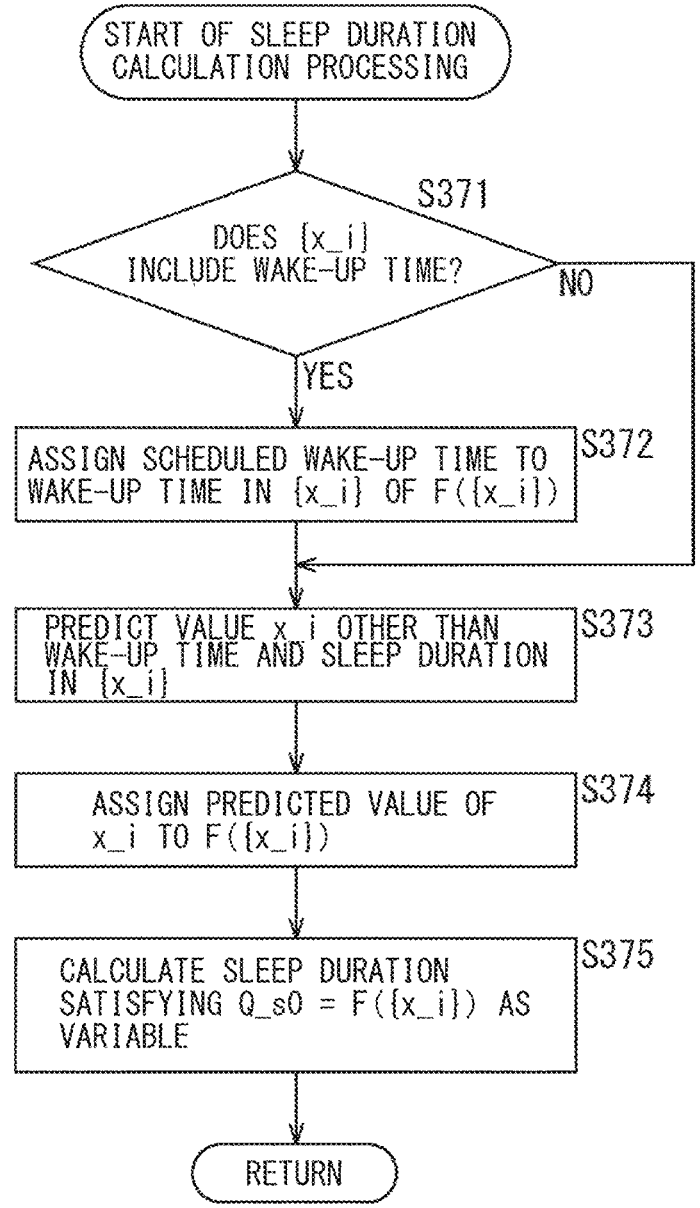
FIG. 35 is a flowchart for describing sleep duration calculation processing performed in step S353 of FIG. 34.

Next, the sleep duration calculation processing performed in the step S353 of FIG. 34 is described with reference to the flowchart in FIG. 35. For calculation of the sleep duration, the algorithm F for estimating the sleep quality $Q\_s$ from the measurement data $\{x\_i\}$ described above is used. It is to be noted that the measurement data $\{x\_i\}$ in this case includes bedtime, a wake-up time, and a duration from going to bed to sleep onset.

In step S371, the scheduled time determining unit 312 determines whether or not the measurement data $\{x\_i\}$ includes the wake-up time. If it is determined in the step S371 that the wake-up time is included in the measurement data $\{x\_i\}$, the processing proceeds to step S372.

In the step S372, the scheduled time determining unit 312 assigns the scheduled wake-up time set in the step S352 of FIG. 34 to the wake-up time in $\{x\_i\}$ of $F(\{x\_i\})$ of the expression (5).

In a case where it is determined in the step S371 that the measurement data $\{x\_i\}$ does not include the wake-up time, the step S372 is skipped.

Here, the sleep duration is a duration obtained by subtracting a duration necessary to fall asleep from a duration from the bedtime to the scheduled wake-up time (the sleep duration=the scheduled wake-up time—the bedtime—the duration necessary to fall asleep). In step S373, the scheduled time determining unit 312 predicts a value $x\_i$ other than the wake-up time and the sleep duration in $\{x\_i\}$.

In step S374, the scheduled time determining unit 312 assigns the predicted value of $x\_i$ to $F(\{x\_i\})$.

In step S375, the scheduled time determining unit 312 calculates, as an optimal sleep duration, a sleep duration satisfying (as much as possible) the target value $Q\_s0=F(\{x\_i\})$ with use of the sleep duration as a variable $x\_i$. In a case where a solution is not obtained, for example, a sleep duration closest to the target value $Q\_s0$ is regarded as the optimal sleep duration within an allowable range from the current time and the lifestyle pattern.

After processing in the step S375, the processing returns to the step S353 of FIG. 34, and processing after the step S353 is performed.

Next, the sleeping environment adjustment processing performed in the step S314 of FIG. 31 is described with reference to the flowchart in FIG. 36.

In step S391, the sleeping controller 314 obtains the measurement data $\{x\_i\}$ representing the sleep state and the sleep environment.

In step S392, the sleeping controller 314 estimates current sleep quality $Q\_s1$. The sleep quality $Q\_s1$ is estimated on the basis of the above expression (5) with use of the measurement data $\{x\_i\}$ obtained in the step S391, for example.

In step S393, the sleeping controller 314 determines whether or not the sleep quality $Q\_s1$ estimated in the step S392 is the same as the target value $Q\_s0$.

In a case where it is determined in the step S393 that the sleep quality $Q\_s1$ is not less than or equal to the sleep quality target value $Q\_s0$, the processing proceeds to step S394.

In the step S394, the sleeping controller 314 adjusts the sleep environment. For example, processing for adjusting a temperature and humidity in a room or a temperature and humidity in bedclothes is performed as adjustment of the sleep environment.

In a case where it is determined in the step S393 that the sleep quality Q_s1 is less than or equal to the sleep quality target value Q_s0, processing in the step S394 is skipped.

In step S395, the sleeping controller 314 determines whether or not the current time is close to the scheduled wake-up time determined by the scheduled time determining unit 312. In a case where it is determined in the step S395 that the current time is not close to the scheduled wake-up time, the processing returns to the step S391, and processing from the step S391 is repeated.

In contrast, in a case where, in the step S395, the current time is only a predetermined time such as 30 minutes before the scheduled wake-up time, and it is therefore determined that the current time is close to the scheduled wake-up time, the processing proceeds to step S396.

In the step S396, the sleeping controller 314 performs wake-up processing at an optimal timing. The wake-up processing at the optimal timing is described in detail later with reference to the flowchart in FIG. 37.

After the processing in step S396, the sleeping environment adjustment processing is ended, and the processing after the step S314 of FIG. 31 is performed.

Figure 36:
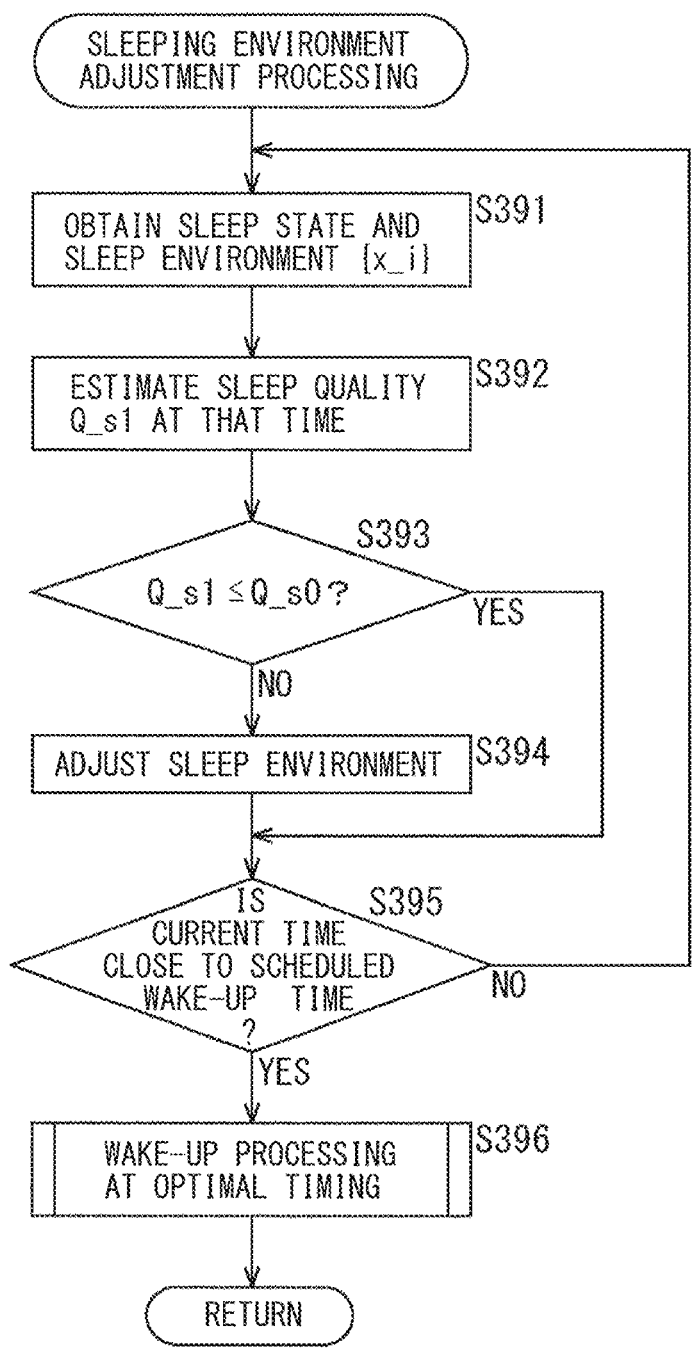
FIG. 36 is a flowchart for describing sleeping environment adjustment processing performed in step S314 of FIG. 31.
Figure 37:
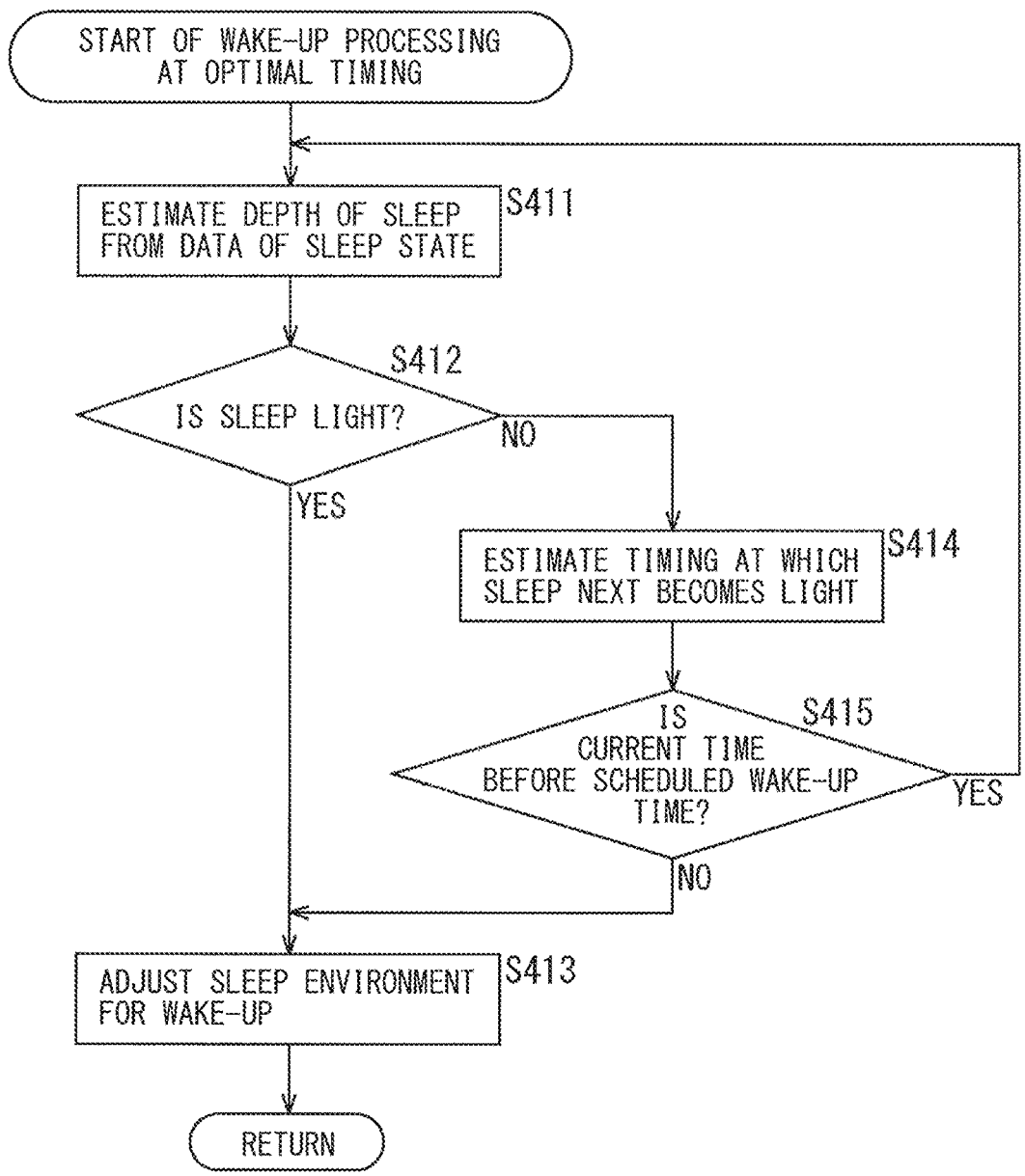
FIG. 37 is a flowchart for describing wake-up processing performed in step S396 of FIG. 36.

Next, the wake-up processing at the optimal timing performed in the step S396 of FIG. 36 is described with reference to the flowchart of FIG. 37.

In step S411, the sleeping controller 314 estimates a depth of sleep of the user from the measurement data of the sleep state. For example, the depth of sleep may be estimated with use of measurement data such as body motion, pulse, respiration, and a body temperature during sleep. The depth of sleep is represented as a numerical value.

In step S412, the sleeping controller 314 determines whether or not sleep is light. Here, for example, in a case where the estimated depth of sleep is lower than a threshold value, it is determined that sleep is light. In a case where it is determined in the step S412 that sleep is deep, the processing proceeds to step S413.

In the step S413, the sleeping controller 314 adjusts the sleep environment for wake-up. As described above, adjustment for waking the user up is performed with use of any method such as gradually increasing brightness of a room light, playing favorite music of the user, gradually increasing the volume of music, diffusing an aroma or incense, and shaking.

In contrast, in a case where, in the step S412, the estimated depth of sleep is higher than the threshold value and it is therefore determined that sleep is deep, the processing proceeds to step S414.

In the step S414, the sleeping controller 314 estimates a timing at which sleep next becomes light. Normally, the timing at which sleep is light is periodic.

In step S415, the sleeping controller 314 determines whether or not the current time is before the scheduled wake-up time. In a case where the scheduled wake-up time has not yet come, and it is therefore determined in the step S415 that the current time is before the scheduled wake-up time, the processing returns to the step S411 and processing from the step S411 is repeated.

In contrast, in a case where it is determined in the step S414 that the current time is not before the scheduled wake-up time, that is, the scheduled wake-up time has come, the processing proceeds to step S413, and the sleep environment for waking the user up is adjusted. Even in a case where sleep is deep, when the current time has passed the scheduled wake-up time, processing for waking the user up is performed.

After the sleep environment for wake-up is adjusted in the step S413, and the user wakes up, the processing returns to the step S396 of FIG. 36, and processing after the step S396 is performed.

Through a series of processing described above, it is possible to optimize sleep of the user, and allowing the user to take a sufficient rest makes it possible to decrease stress.

The case where the stress level is higher than usual, and the stress level is decreased on the following day has been described above as an example; however, it is possible to perform control not to decrease the stress level.

For example, in a case where the stress level during the daytime is low, tomorrow is a holiday, and it does not matter even if the stress level is rather high, the above-described control to improve sleep quality is not necessary. Accordingly, the user may be informed that the user is allowed to stay up late to watch the television or is allowed to play a game.

Even in this case, it is preferable to avoid increasing the stress level to a level that is not able to be restored by a rest on the following day. In addition, too much disruption of a living rhythm also makes it difficult to restore the stress level. It is possible to make a suggestion for informing a time until which the user is allowed to stay up late and preparing for sleep after a time limit.

[System Configuration]

One embodiment of the present technology has been described above. As described above, the stress control system 10 according to the present embodiment includes the input unit 11, the processing unit 13, and the output unit 15, and these components are implemented by one or a plurality of information processing apparatuses. Examples of a combination of information processing apparatuses for implementing the stress control system 10 are described below together with more specific examples.

First Example

Figure 38:
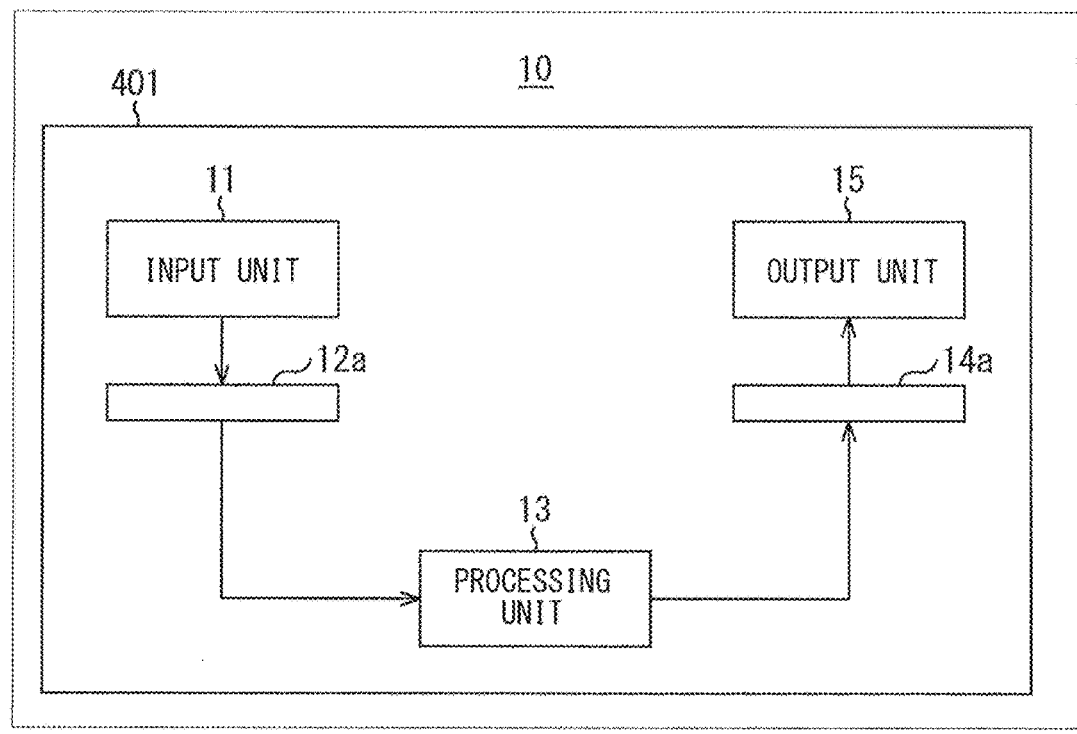
FIG. 38 is a block diagram illustrating a first example of a system configuration according to an embodiment of the present technology.

FIG. 38 is a block diagram illustrating a first example of a system configuration according to the embodiment of the present technology.

The stress control system 10 in FIG. 38 includes an information processing apparatus 401. The input unit 11, the processing unit 13, and the output unit 15 are all implemented in the information processing apparatus 401. The information processing apparatus 401 serves as a terminal apparatus or a server as described below.

In this first example, the information processing apparatus 401 may be a stand-alone apparatus that does not communicate with an external apparatus via a network. It is to be noted that the information processing apparatus 401 may communicate with an external apparatus for other functions, and may not be a stand-alone apparatus. Each of an interface 12a between the input unit 11 and the processing unit 13, and an interface 14a between the processing unit 13 and the output unit 15 is an interface in the apparatus.

In the first example, the information processing apparatus 401 serves as a terminal apparatus, for example. In this example, the input unit 11 includes an input apparatus, a sensor, software for obtaining information from an external service, and the like. The software for obtaining information from the external service obtains data from, for example, application software of a service executed on the terminal apparatus.

The processing unit 13 is implemented by a processor or a processing unit, which is included in the terminal apparatus, operating in accordance with a program stored in a memory or a storage apparatus. The output unit 15 includes an output apparatus, a control apparatus, software for providing information to an external service, and the like. The software for providing information to the external service provides the information to, for example, application software of a service executed in the terminal apparatus.

It is to be noted that, in the first example, the information processing apparatus 401 may serve as a server. In this example, the input unit 11 includes software for obtaining information from an external service. The software for obtaining information from the external service obtains data from a server of the external service (which may be the information processing apparatus 401 itself), for example.

The processing unit 13 is implemented by a processor, which is included in the terminal apparatus, operating in accordance with a program stored in a memory or a storage apparatus. The output unit 15 may include software for providing information to an external service. The software for providing information to the external service provides information to a server of the external service (which may be the information processing apparatus 401 itself), for example.

Second Example

Figure 39:
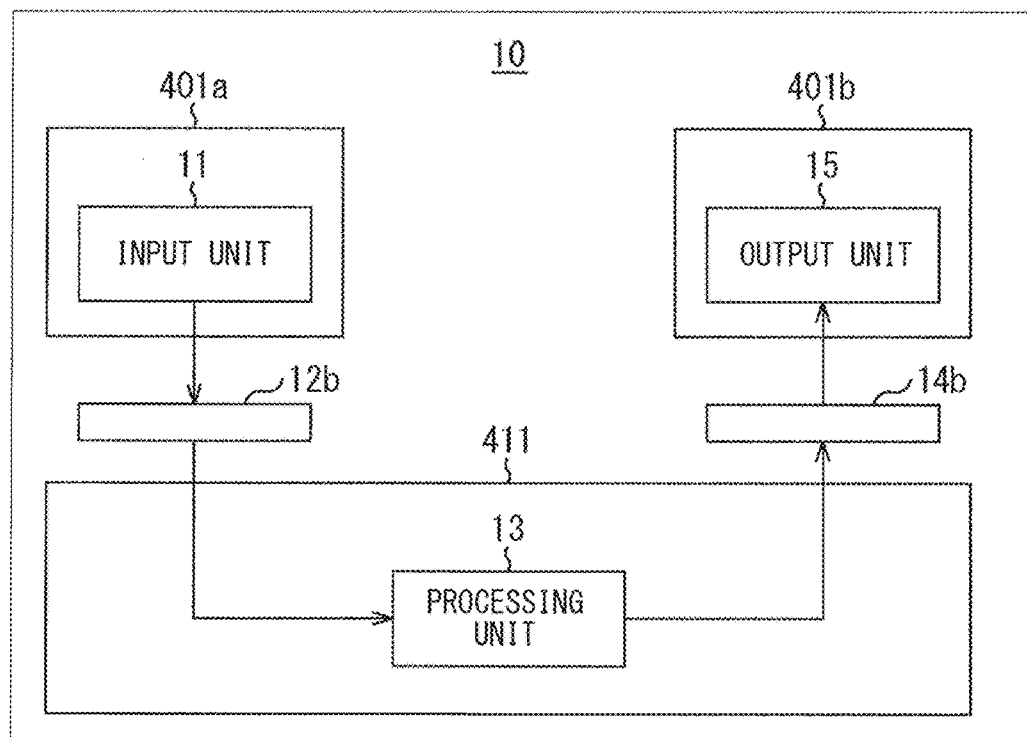
FIG. 39 is a block diagram illustrating a second example of the system configuration according to the embodiment of the present technology.

FIG. 39 is a block diagram illustrating a second example of the system configuration according to the embodiment of the present technology.

The stress control system 10 in FIG. 39 includes information processing apparatuses 401a, 401b, and 411. The input unit 11 is implemented in the information processing apparatus 401a. The output unit 15 is implemented in the information processing apparatus 401b. In addition, the processing unit 13 is implemented in the information processing apparatus 411. The information processing apparatuses 401a and 401b and the information processing apparatus 411 communicate with each other via a network in order to implement functions according to the embodiment of the present technology.

Each of an interface 12b between the input unit 11 and the processing unit 13 and an interface 14b between the processing unit 13 and the output unit 15 is a communication interface between apparatuses. However, in the second example, the information processing apparatus 401a and the information processing apparatus 401b are separate apparatuses; therefore, the interfaces 12b and 14b include different types of interfaces.

The information processing apparatus 401a and the information processing apparatus 401b may be configured by a single apparatus. In such a case, the interface 12b and 14b are interfaces of the same type.

In the second example, the information processing apparatus 401a and 401b serve as terminal apparatuses, for example. In this case, the input unit 11 includes an input apparatus, a sensor, software for obtaining information from an external service, and the like, similarly to the first example described above. The output unit 15 includes an output apparatus, a control apparatus, software for providing information to an external service, and the like, similarly to the first example described above.

Alternatively, one or both of the information processing apparatuses 401a and 401b may serve as a server for obtaining information from an external service and providing information to an external service. In this case, the input unit 11 includes software for obtaining information from the external service. In addition, the output unit 15 includes software for providing information to the external service.

In addition, in the second example, the information processing apparatus 411 serves as a server or a terminal apparatus. The processing unit 13 is implemented by a processor or a processing unit, which is included in the information processing apparatus 411, operating in accordance with a program stored in a memory or a storage apparatus.

In the second example described above, the information processing apparatus 401a that implements the input unit 11 and the information processing apparatus 401b that implements the output unit 15 are separate apparatuses. Accordingly, for example, it is possible to implement a function of outputting a result of processing on the basis of an input obtained by the information processing apparatus 401a, which is a terminal apparatus owned or used by a first user, from the information processing apparatus 401b, which is a terminal apparatus owned or used by a second user. The second user is different from the first user.

In addition, it is also possible to implement a function of outputting a result of processing on the basis of an input obtained by the information processing apparatus 401a, which is a terminal apparatus owned or used by the first user, from the information processing apparatus 401b, which is a terminal apparatus that is not in a hand of the first user at that time (for example, the terminal apparatus is installed at home where the first user is absent).

Alternatively, the information processing apparatus 401a and the information processing apparatus 401b may both serve as terminal apparatuses that are owned or used by the same user. For example, in a case where the information processing apparatuses 401a and 401b are wearable devices attached to different parts of the user, or in a case where the information processing apparatuses 401a and 401b configure a combination of a wearable device and a mobile device, it is possible to provide the user with a function linking these devices.

It is to be noted that, in the example illustrated in FIG. 39, the processing unit 13 is configured only by the information processing apparatus 411; however, processing units 13a and 13b that perform a portion of processing of the processing unit 13 may be configured by the information processing apparatuses 401a and 401b.

Even in a case where the information processing apparatuses 401a and 401b are configured by a single apparatus, the processing unit 13 that performs a portion of processing of the processing unit 13 may be configured by the information processing apparatus 401 that is a single apparatus.

(Example of Client Server System)

Figure 40:
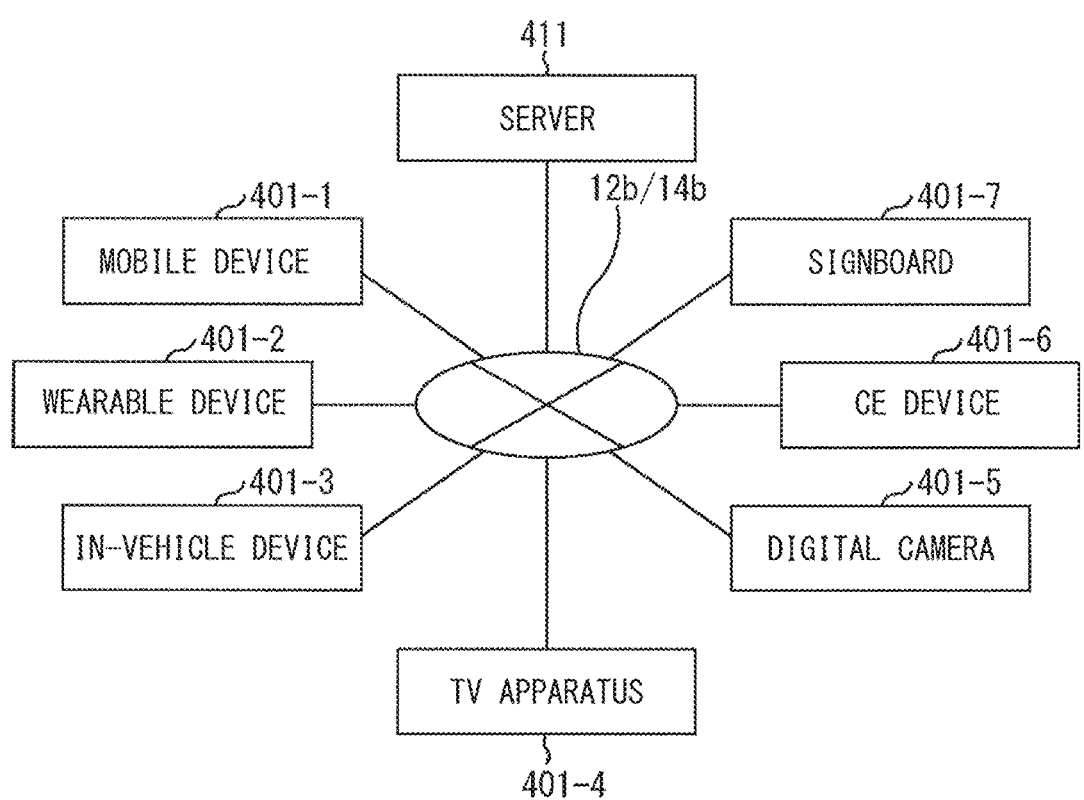
FIG. 40 is a diagram illustrating a client server system according to the embodiment of the present technology.

FIG. 40 is a diagram illustrating a client server system as one of more specific examples of the system configuration according to the embodiment of the present technology.

In FIG. 40, the information processing apparatus 401 (or the information processing apparatuses 401a and 401b) serves as a terminal apparatus, and the information processing apparatus 411 serves as a server.

The terminal apparatus in FIG. 40 includes a mobile device 401-1, a wearable device 401-2, an in-vehicle device 401-3, a TV apparatus 401-4, a digital camera 401-5, a CE (Consumer Electronics) device 401-6, a signboard 401-7, and the like.

The mobile device 401-1 includes a smartphone, a tablet terminal, a notebook PC (Personal Computer), or the like. The wearable device 401-2 includes an eyewear or contact lens type terminal, a watch type terminal, a bracelet type terminal, a ring type terminal, a headset, a clothing attachment type or clothing integration type terminal, a shoe attachment type or shoe integration type terminal, a necklace type terminal, or the like.

The in-vehicle device 401-3 includes a car navigation system, a rear seat entertainment system, and the like. The CE device 401-6 includes a recorder, a gaming machine, an air conditioner, a refrigerator, a washing machine, a desktop PC, or the like. The signboard 401-7 includes a digital signboard, and is installed on a street.

The information processing apparatus 401 (terminal apparatus) communicates with the information processing apparatus 411 (server) via a network. The network between the terminal apparatus and the server corresponds to the interface 12b or the interface 14b in the examples described above. Further, these apparatuses may operate individually in cooperation with each other, or a system in which all apparatuses are able to operate in cooperation may be constructed.

It is to be noted that the example illustrated in FIG. 40 is provided to make it easy to understand an example in which the stress control system 10 is implemented in the client server system. Accordingly, the stress control system 10 is not limited to such a client server system, as described in each of the examples described above.

That is, for example, the information processing apparatuses 401 and 411 may both serve as terminal apparatuses, or the information processing apparatuses 401 and 411 may both serve as servers. In a case where the information processing apparatus 401 includes the information processing apparatuses 401a and 401b, one of the information processing apparatuses 401a and 401b may serve as a terminal apparatus and the other may serve as a server.

In addition, even in a case where the information processing apparatus 401 serves as a terminal apparatus, examples of the terminal apparatus are not limited to the mobile device 401-1, the wearable device 401-2, the in-vehicle device 401-3, the TV apparatus 401-4, the digital camera 401-5, the CE device 401-6, and the signboard 401-7 described above, and may include other types of terminal apparatuses.

Third Example

Figure 41:
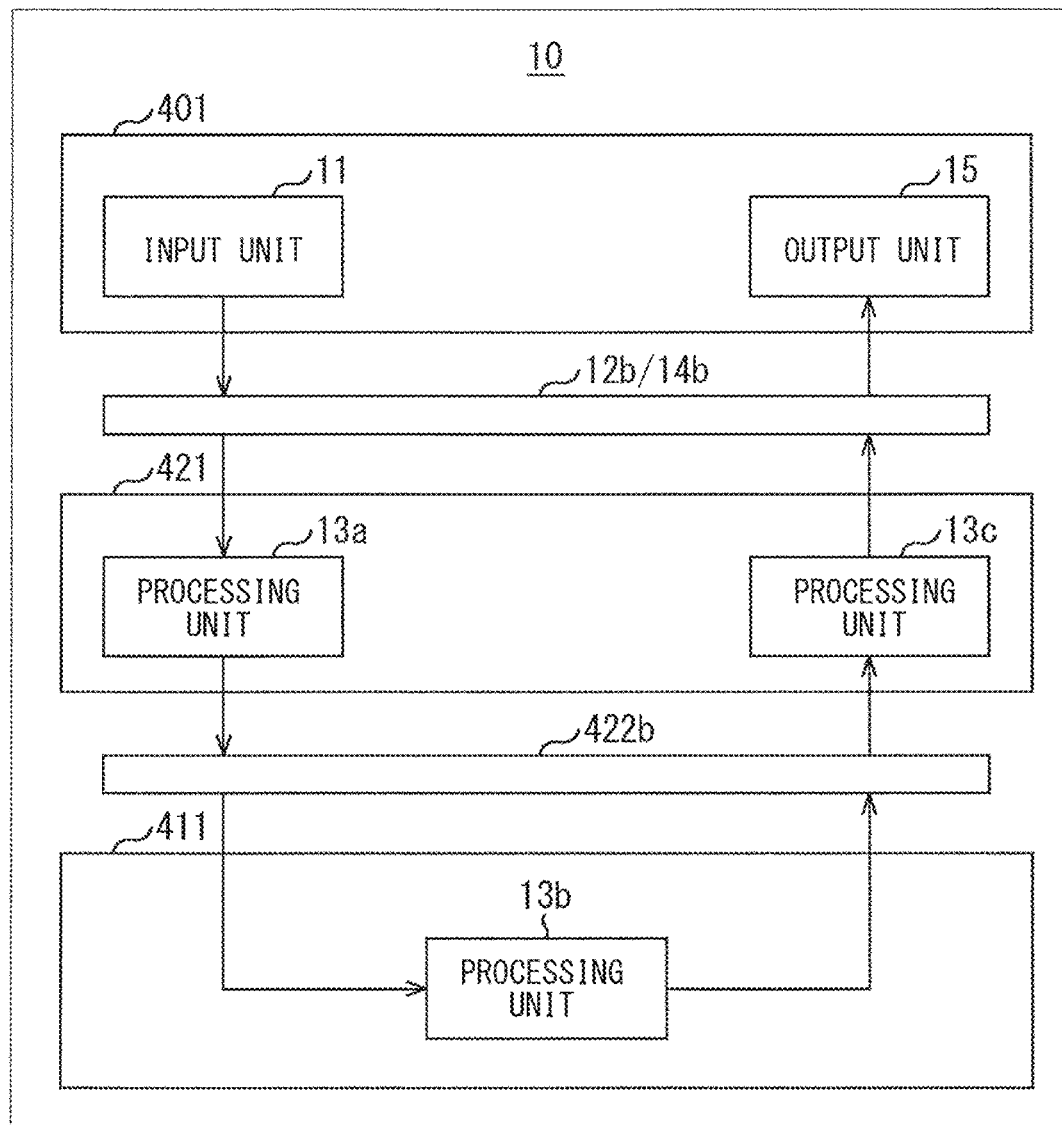
FIG. 41 is a block diagram illustrating a third example of the system configuration according to the embodiment of the present technology.

FIG. 41 is a block diagram illustrating a third example of the system configuration according to the embodiment of the present technology.

The stress control system 10 in FIG. 41 includes information processing apparatuses 401, 411, and 421. The input unit 11 and the output unit 15 are implemented in the information processing apparatus 401. In contrast, the processing unit 13 is implemented by being distributed to the information processing apparatus 411 and the information processing apparatus 421. In order to implement the functions according to the embodiment of the present technology, the information processing apparatus 401 and the information processing apparatus 411 communicate with each other via a network, and the information processing apparatus 411 and the information processing apparatus 421 communicate with each other via the network.

As described above, in this third example, the processing unit 13 is implemented by being distributed between the information processing apparatus 421 and the information processing apparatus 411. More specifically, the processing unit includes processing units 13a and 13c implemented in the information processing apparatus 421, and a processing unit 13b implemented in the information processing apparatus 411. The processing unit 13a executes processing on the basis of information provided from the input unit 11 via the interface 12b, and provides a result of the processing to the processing unit 13b via an interface 422b.

In contrast, the processing unit 13c executes processing on the basis of information provided from the processing unit 13b via the interface 422b, and provides a result of the processing to the output unit 15 via the interface 14b. It is to be noted that, in the illustrated example, the processing unit 13a that executes pre-processing and the processing unit 13c that executes post-processing are both illustrated; however, in reality, only one of them may exist.

In the third example, the information processing apparatus 421 is interposed between the information processing apparatus 401 and the information processing apparatus 411. More specifically, for example, the information processing apparatus 421 serves as a terminal apparatus or a server interposed between the information processing apparatus 401 serving as a terminal apparatus and the information processing apparatus 411 serving as a server.

Examples in which the information processing apparatus 421 serves as a terminal apparatus include a case where the information processing apparatus 401 is a wearable device, the information processing apparatus 421 is a mobile device coupled to the wearable device by Bluetooth (registered trademark), and the information processing apparatus 411 is a server coupled to the mobile device via the Internet. In addition, examples in which the information processing apparatus 421 serves as a server include a case where the information processing apparatus 401 is various types of terminal apparatuses, the information processing apparatus 421 is an intermediate server coupled to the terminal apparatuses via a network, and the information processing apparatus 411 is a serer coupled to the intermediate server via the network.

Fourth Example

Figure 42:
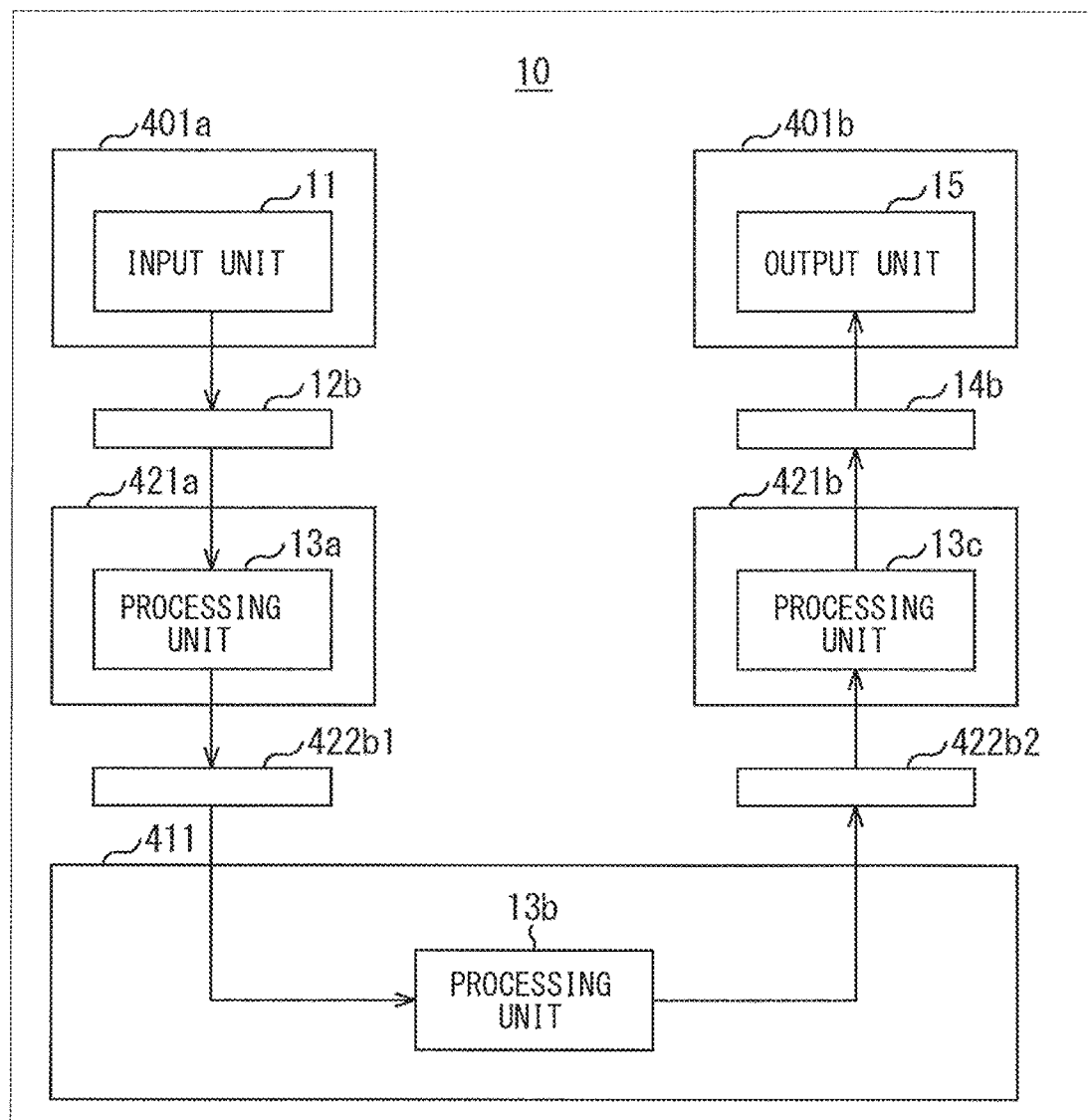
FIG. 42 is a block diagram illustrating a fourth example of the system configuration according to the embodiment of the present technology.

FIG. 42 is a block diagram illustrating a fourth example of the system configuration according to the embodiment of the present technology.

The stress control system 10 in FIG. 42 includes information processing apparatuses 401a, 401b, 421a, 421b, and 411.

In this fourth example, the input unit 11 is implemented in the information processing apparatus 401a. The output unit 15 is implemented in the information processing apparatus 401b. In contrast, the processing unit 13 is implemented by being distributed to the information processing apparatuses 421a and 421b and the information processing apparatus 411. In order to implement the functions according to embodiment of the present technology, the information processing apparatus 401a and the information processing apparatus 421a communicate with each other via a network, the information processing apparatus 401b and the information processing apparatus 421b communicate with each other via the network, and the information processing apparatuses 421a and 421b, and the information processing apparatus 411 communicate with each other via the network.

In the fourth example, the information processing apparatus 401a that implements the input unit 11 and the information processing apparatus 401b that implements the output unit 15 are separate apparatuses. Each of the information processing apparatuses 401a and 401b communicates with a corresponding one of separate intermediate nodes (the information processing apparatuses 421a and 421b). Accordingly, in this fourth example, in addition to implementing the processing unit 13 by distributing the processing unit 13 to three servers (the information processing apparatuses 421*a*, 421*b*, and 411), it is possible to implement the functions according to the embodiment of the present technology with use of the information processing apparatuses 401*a* and 401*b* that may be terminal apparatuses owned or used by the same user, or owned or used by different users.

In the fourth example, although not illustrated, the information processing apparatus 401*a* and the information processing apparatus 401*b* may be configured as a single apparatus. In addition, in the fourth example, the information processing apparatuses 421*a* and 421*b* may be configured as a single apparatus.

(Example of System Including Intermediate Server)

Figure 43:
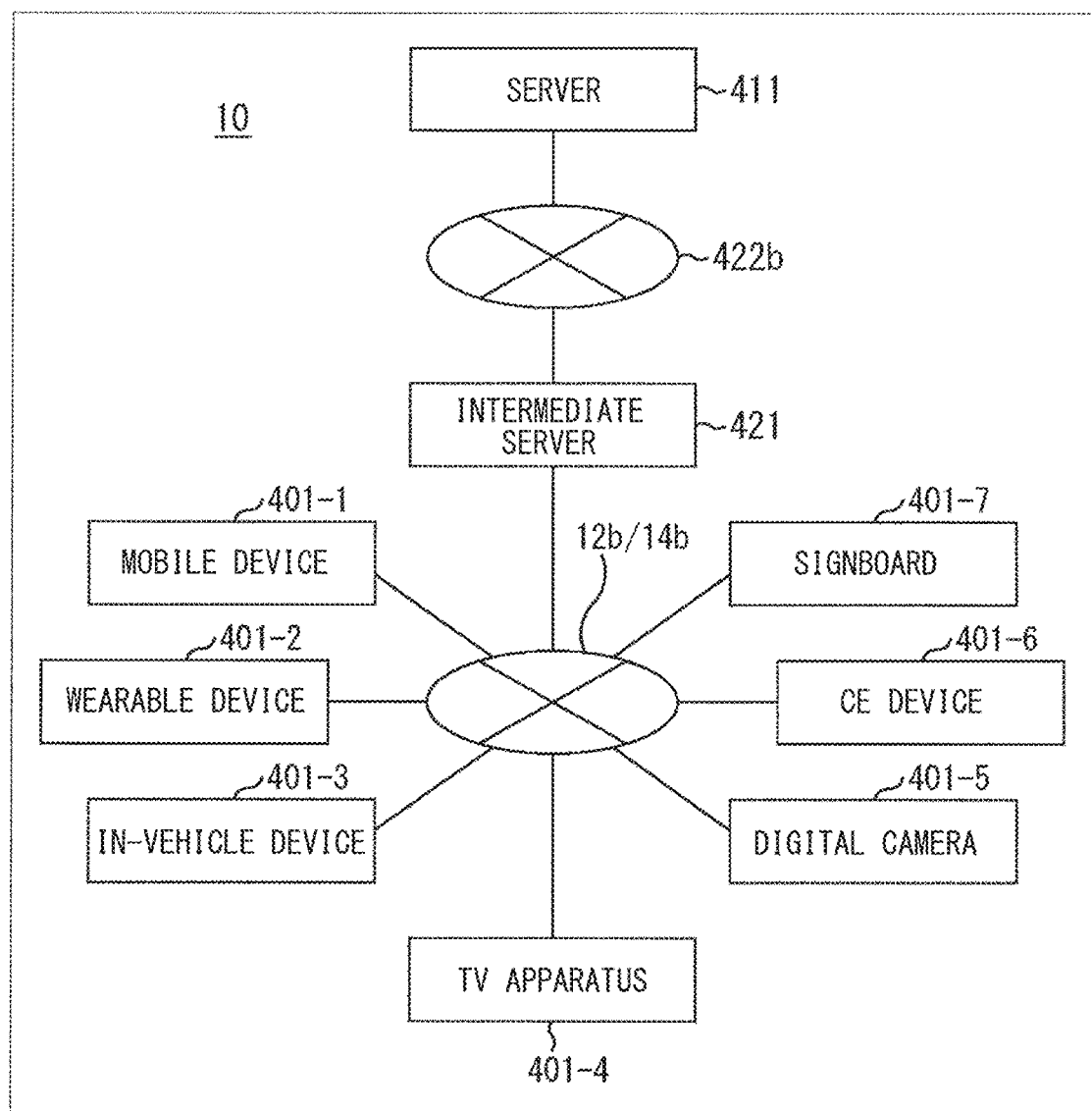
FIG. 43 is a diagram illustrating an example of a system including an intermediate server according to the embodiment of the present technology.

FIG. 43 is a diagram illustrating an example of a system including an intermediate server as one of the more specific examples of the system configuration according to the embodiment of the present technology.

In the system in FIG. 43, the information processing apparatus 401 (or the information processing apparatuses 401*a* and 401*b*) serves as a terminal apparatus, the information processing apparatus 421 serves as an intermediate server, and the information processing apparatus 411 serves as a server.

The terminal apparatus in FIG. 43 includes the mobile device 401-1, the wearable device 401-2, the in-vehicle device 401-3, the TV apparatus 401-4, the digital camera 401-5, the CE device 401-6, a robot device, the signboard 401-7, or the like, similarly to the example described with reference to FIG. 40.

The information processing apparatus 401 (terminal apparatus) communicates with the information processing apparatus 421 (intermediate server) via a network. The network between the terminal apparatus and the intermediate server corresponds to the interfaces 12*b* and 14*b* in the examples described above. In addition, the information processing apparatus 421 (intermediate server) communicates with the information processing apparatus 411 (server) via a network. The network between the intermediate server and the server corresponds to the interface 422*b* in the example described above.

It is to be noted that the example illustrated in FIG. 43 is provided to make it easy to understand an example in which the stress control system 10 is implemented in the system including the intermediate server. The stress control system 10 is not limited to such a system, as described in each of the examples described above.

(Example of System Including Terminal Apparatus Serving as Host)

Figure 44:
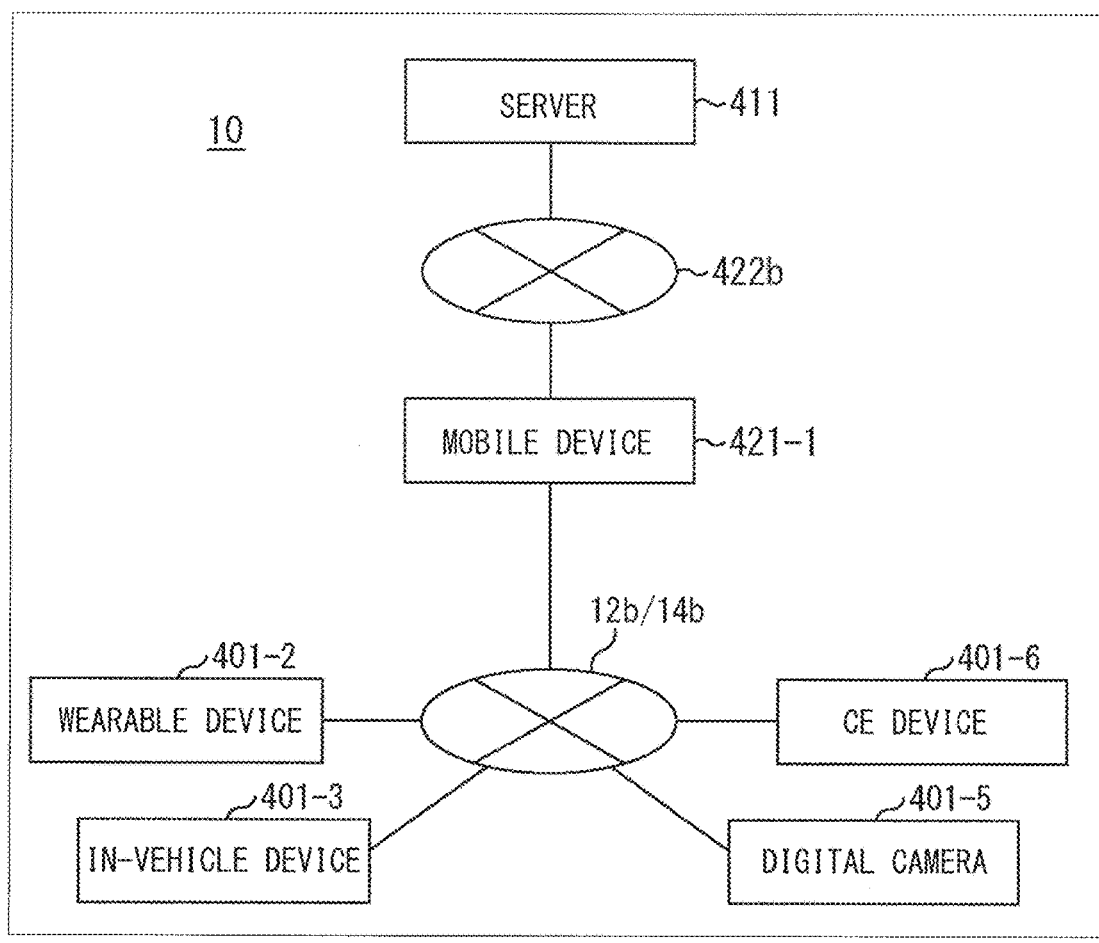
FIG. 44 is a diagram illustrating an example of a system including a terminal apparatus serving as a host according to the embodiment of the present technology.

FIG. 44 is a diagram illustrating an example of a system including a terminal apparatus serving as a host as one of the more specific examples of the system configuration according to the embodiment of the present technology.

In the system in FIG. 44, the information processing apparatus 401 (or the information processing apparatuses 401*a* and 401*b*) serves as a terminal apparatus, the information processing apparatus 421 serves as a terminal apparatus serving as a host, and the information processing apparatus 411 serves as a server.

The terminal apparatus illustrated in FIG. 44 includes, for example, the wearable device 401-2, the in-vehicle device 401-3, the digital camera 401-5, a robot device, a device including a sensor or the like attached to a facility, and the CE device 401-6. The information processing apparatus 401 (terminal apparatus) communicates with the information processing apparatus 421 via a network such as Bluetooth (registered trademark) or Wi-Fi, for example.

In FIG. 44, a mobile device 421-1 is exemplified as a terminal apparatus serving as a host. A network between the terminal apparatus and the mobile device corresponds to the interfaces 12*b* and 14*b* in the examples described above. The information processing apparatus 421 (mobile device) communicates with the information processing apparatus 411 (server) via a network such as the Internet, for example. The network between the mobile device and the server corresponds to the interface 422*b* in the example described above.

It is to be noted that the example illustrated in FIG. 44 is provided to make it easy to understand an example in which the stress control system 10 is implemented in the system including the terminal apparatus serving as a host. The stress control system 10 is not limited to such a system, as described in each of the examples described above. In addition, the terminal apparatus serving as a host is not limited to the mobile device 421-1 in the illustrated example, and various types of terminal apparatuses having an appropriate communication function and an appropriate processing function serve as a host.

In addition, the wearable device 401-2, the in-vehicle device 401-3, the digital camera 401-5, and the CE device 401-6 illustrated as examples of the terminal apparatus do not exclude terminal apparatuses other than these apparatuses from this example. These apparatuses indicate examples of a typical terminal apparatus that may be the information processing apparatus 401 in a case where the information processing apparatus 421 is the mobile device 421-1.

[Hardware Configuration]

Next, a hardware configuration of the information processing apparatus according to the embodiment of the present technology is described with reference to FIG. 45.

Figure 45:
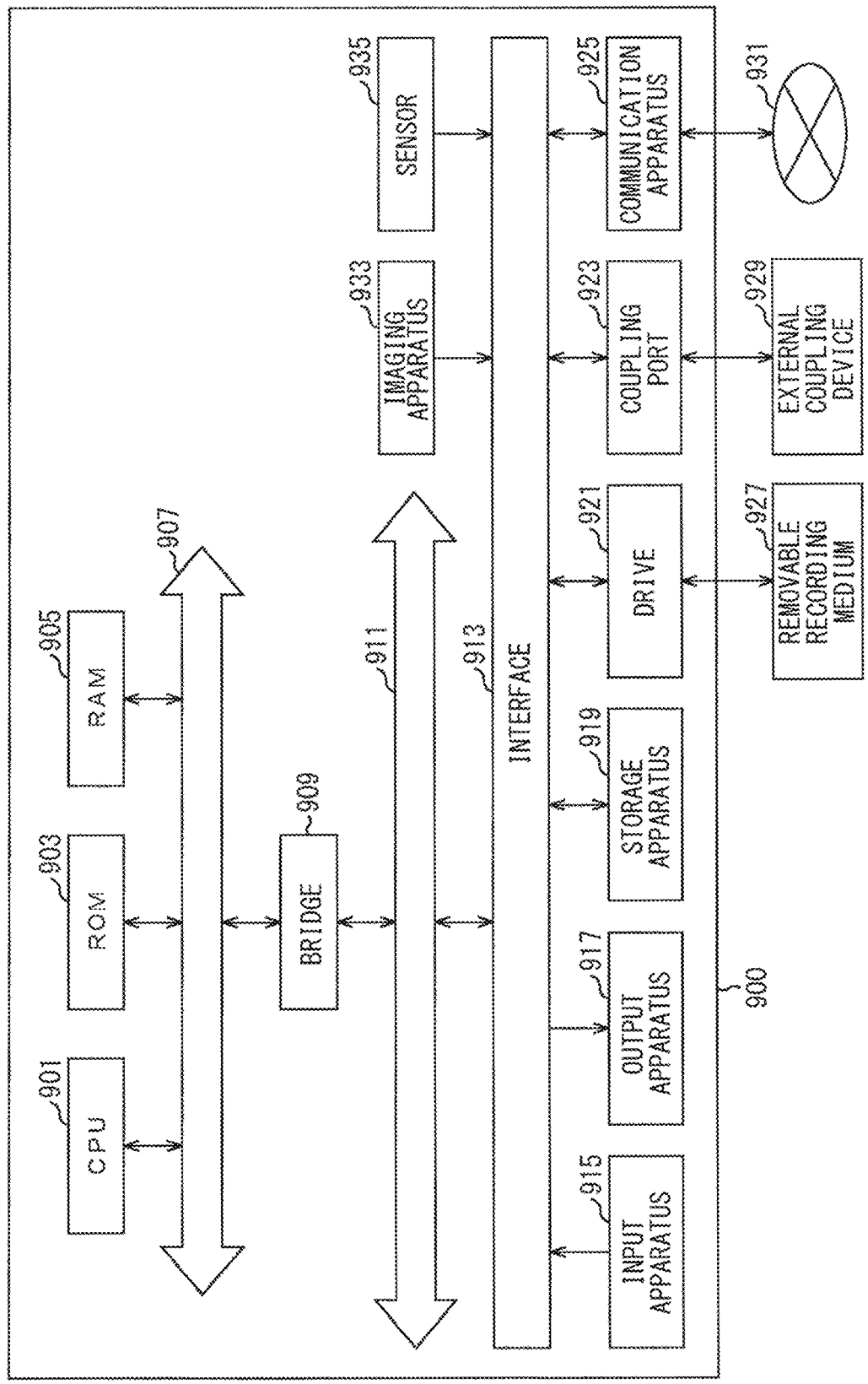
FIG. 45 is a block diagram illustrating a hardware configuration example of an information processing apparatus according to the embodiment of the present technology.

FIG. 45 is a block diagram illustrating a hardware configuration example of the information processing apparatus according to the embodiment of the present technology.

A information processing apparatus 900 includes a CPU (Central Processing unit) 901, a ROM (Read Only Memory) 903, and a RAM (Random Access Memory) 905. In addition, the information processing apparatus 900 may include a host bus 907, a bridge 909, an external bus 911, an interface 913, an input apparatus 915, an output apparatus 917, a storage apparatus 919, a drive 921, a coupling port 923, and a communication apparatus 925. The information processing apparatus 900 may further include an imaging apparatus 933 and a sensor 935 as necessary. The information processing apparatus 900 may have a processing circuit such as a DSP (Digital Signal Processor), an ASIC (Application Specific Integrated Circuit), or an FPGA (Field-Programmable Gate Array) instead of or together with the CPU 901.

The CPU 901 serves as an arithmetic processing apparatus and a control apparatus, and controls the entirety or a portion of an operation in the information processing apparatus 900 in accordance with various programs recorded on the ROM 903, the RAM 905, the storage apparatus 919, or a removable recording medium 927. The ROM 903 stores a program, an operation parameter, and the like used by the CPU 901. The RAM 905 primarily stores a program used in execution of the CPU 901, a parameter that changes as appropriate in the execution, and the like. The CPU 901, the ROM 903 and the RAM 905 are coupled to each other by the host bus 907 including an internal bus such as a CPU bus. Further, the host bus 907 is coupled to the external bus 911 such as a PCI (Peripheral Component Interconnect/Interface) bus via the bridge 909.

The input apparatus 915 is, for example, an apparatus operated by a user, such as s mouse, a keyboard, a touch panel, a button, a switch, and a lever. The input apparatus 915 may be, for example, a remote control apparatus using infrared rays or other electric waves, or may be an external coupling device 929, such as a mobile phone, corresponding to the operation of the information processing apparatus 900. The input apparatus 915 includes an input control circuit that generates an input signal on the basis of information inputted by a user and outputs the input signal to the CPU 901. The user operates this input apparatus 915, thereby inputting various types of data to the information processing apparatus 900 or instructing the information processing apparatus 900 to perform a processing operation.

The output apparatus 917 includes an apparatus that is allowed to notify the user of obtained information using a sense such as a visual sense, an auditory sense, and a tactile sense. The output apparatus 917 is, for example, a display apparatus such as an LCD (Liquid Crystal Display) or organic EL (Electro-Luminescence) display, an audio output apparatus such as a speaker or a headphone, or a vibrator. The output apparatus 917 outputs a result obtained by the processing of the information processing apparatus 900 as vision such as text or an image, audio such as a voice or a sound, vibration, or the like.

The storage apparatus 919 is an apparatus for data storage configured as an example of a storage unit of the information processing apparatus 900. The storage apparatus 919 includes, for example, a magnetic storage unit device such as an HDD (Hard Disk Drive), a semiconductor storage device, an optical storage device, a magneto-optical storage device, or the like. The storage apparatus 919 stores, for example, a program and various types of data to be executed by the CPU 901, various types of data obtained from outside, and the like.

The drive 921 is a reader/writer for the removable recording medium 927 such as a magnetic disk, an optical disk, a magneto-optical disk, or a semiconductor memory, and is built in or externally mounted on the information processing apparatus 900. The drive 921 reads information recorded on the mounted removable recording medium 927 and outputs the information to the RAM 905. The drive 921 writes a record to the mounted removable recording medium 927.

The coupling port 923 is a port for coupling a device to the information processing apparatus 900. Examples of the coupling port 923 include a USB (Universal Serial Bus) port, an IEEE1394 port, an SCSI (Small Computer System Interface) port, and the like. In addition, the coupling port 923 may be an RS-232C port, an optical audio terminal, an HDMI (registered trademark) (High-Definition Multimedia Interface) port, or the like. Coupling the external coupling device 929 to the coupling port 923 causes various types of data to be exchanged between the information processing apparatus 900 and the external coupling device 929.

The communication apparatus 925 is, for example, a communication interface including a communication device for coupling to the communication network 931. The communication apparatus 925 may be, for example, a communication card or the like for LAN (Local Area Network), Bluetooth (registered trademark), Wi-Fi, or WUSB (Wireless USB). In addition, the communication apparatus 925 may be a router for optical communication, a router for ADSL (Asymmetric Digital Subscriber Line), a modem for various types of communication, or the like. The communication apparatus 925 transmits and receives a signal and the like to and from the Internet or other communication devices with use of a predetermined protocol such as TCP/IP, for example. The communication network 931 coupled to the communication apparatus 925 is a network coupled by wire or without wires, and includes, for example, the Internet, a domestic LAN, infrared communication, radio wave communication, satellite communication, and the like.

The imaging apparatus 933 is an apparatus for capturing an image of a real space with use of various members including an imaging element such as a CMOS (Complementary Metal Oxide Semiconductor) or a CCD (Charge Coupled Device), a lens for controlling image formation of a subject image on the imaging element, and the like to generate a captured image. The imaging apparatus 933 may capture a still image or may capture a moving image.

Examples of the sensor 935 include various types of sensors such as an acceleration sensor, an angular velocity sensor, a geomagnetic sensor, an illumination sensor, a temperature sensor, a barometric pressure sensor, or a sound sensor (a microphone). The sensor 935 obtains, for example, information about a state of the information processing apparatus 900 itself, such as a posture of a housing of the information processing apparatus 900, and information about a surrounding environment of the information processing apparatus 900, such as brightness and noise around the information processing apparatus 900. In addition, the sensor 935 may include a GPS receiver that receives a GPS (Global Positioning System) signal and measures a latitude, a longitude, and an altitude of an apparatus.

An example of the hardware configuration has been described above. The respective components described above may be achieved by using general-purpose members, or may be achieved by hardware specific to functions of the respective components. Such a configuration is changeable as appropriate in accordance with a technical level at the time of implementation.

An embodiment of the present technology may include, for example, the information processing apparatus and the system described above, an information processing method to be executed by the information processing apparatus or the system, a program for causing the information processing apparatus to function, and a non-transitory tangible medium on which the program is recorded.

In addition, an embodiment of the present technology is not limited to the embodiment described above, and may be modified in variety of ways in a scope without departing from the gist of the present technology.

For example, a "system" in this specification means a group of a plurality of components (such as apparatuses and modules (parts)) regardless of whether or not all of the components are in the same housing. Accordingly, a plurality of apparatuses that are accommodated in separate housings and coupled to each other via a network, and a single apparatus including a plurality of modules accommodated in one housing are both regarded as the system.

In addition, for example, a configuration described as a single apparatus (or a processing unit) may be divided and configured as a plurality of apparatuses (or processing units). On the contrary, configurations described above as a plurality of apparatuses (or processing units) may be integrated and configured as a single apparatus (or processing unit). In addition, it is needless to say that a configuration other than those described above may be added to the configuration of each apparatus (or each processing unit). Further, as long as the configuration and an operation of the entire system are substantially the same, a portion of the configuration of a certain apparatus (or processing unit) may be included in the configuration of another apparatus (or another processing unit).

In addition, for example, as the system configurations described above, it is possible for the present technology to adopt a configuration of cloud computing in which one function is distributed to a plurality of apparatuses via a network and processed in cooperation.

Further, for example, it is possible to execute the program described above in any apparatus. In this case, it is sufficient if the apparatus have a necessary function (a functional block or the like) and is able to obtain necessary information.

In addition, for example, it is possible to execute the respective steps described in the flowcharts described above with one apparatus, and it is also possible to distribute the respective steps to a plurality of apparatuses for execution. Further, in a case where a plurality of processing is included in one step, it is possible to execute the plurality of processing included in the one step with one apparatus, and it is also possible to distribute the plurality of processing to a plurality of apparatuses for execution.

It is to be noted that, in a program executed by a computer, processing of steps describing the program may be executed chronologically in the order described herein or may be executed in parallel or individually at necessary timings such as when the processing is invoked. Further, the processing of the steps describing this program may be executed in parallel with processing of another program, or may be executed in combination with processing of another program.

It is to be noted that each of a plurality of present technologies described herein may be implemented as a single technology independently as long as no contradiction arises. Needless to say, any number of the present technologies may be implemented in combination. For example, the present technology described in any of the embodiments may be implemented in combination with the present technology described in another embodiment. In addition, any of the technologies described above may be implemented in combination with another technology not described above.

It is to be noted that the present technology may also be configured as below.

(1)
An information processing apparatus including:
a stress level measuring unit that measures a stress level of a user on the basis of a result of detection by a sensor; and
a stress factor specifying unit that specifies a factor causing an increase or decrease in the stress level on the basis of an action of the user in a period in which the stress level is increased or decreased.

(2)
The information processing apparatus according to (1), in which the stress factor specifying unit further specifies the factor on the basis of an environment of the user in the period in which the stress level is increased or decreased.

(3)
The information processing apparatus according to (1) or (2), further including a processing executing unit that executes an event corresponding to the factor.

(4)
The information processing apparatus according to (3), in which the processing executing unit executes the event corresponding to the factor having caused a decrease in the stress level in a case where the stress level is higher than a threshold value, and executes the event corresponding to the factor having caused an increase in the stress level in a case where the stress level is lower than the threshold value.

(5)
The information processing apparatus according to (3), in which the processing executing unit executes, as the event, processing for causing the user to take an action corresponding to the factor or a suggestion about an action corresponding to the factor.

(6)
The information processing apparatus according to (3), further including an action analyzer that analyzes an action of the user on the basis of the result of detection by the sensor, in which
the processing executing unit executes the event corresponding to the action of the user.

(7)
The information processing apparatus according to any one of (1) to (6), further including an output controller that outputs information representing the increase or decrease in the stress level together with information representing the factor.

(8)
The information processing apparatus according to (7), in which the output controller outputs information representing the factor that is discrete or information representing the factor that is continuous.

(9)
The information processing apparatus according to (8), in which the output controller outputs information representing an action of the user in each time zone as the information representing the factor that is discrete and information representing a change in the result of detection by the sensor as the information representing the factor that is continuous.

(10)
The information processing apparatus according to (7), in which the output controller outputs the information representing the increase or decrease in the stress level together with a moving route of the user with use of a location of the user as the factor.

(11)
The information processing apparatus according to (7), in which the output controller outputs information representing the stress level to a position on a map corresponding to a position where the stress level has been measured with use of a location of the user as the factor.

(12)
The information processing apparatus according to (7), in which the output controller outputs information representing the stress level measured in each period with use of a predetermined period as the factor.

(13)
The information processing apparatus according to (7), in which the output controller outputs information representing the stress level together with information representing a companion of the user with use of the companion of the user as the factor.

(14)
The information processing apparatus according to (5), further including an output unit that makes the suggestion about the action corresponding to the factor with use of voice or AR display.

(15)
The information processing apparatus according to (3), in which the processing executing unit includes:
a target value setting unit that sets a target value of sleep quality on the basis of the increase or decrease in the stress level, and a scheduled time determining unit that determines a scheduled bedtime and a scheduled wake-up time on the basis of the target value.

(16)

The information processing apparatus according to (15), in which the processing executing unit further includes:

a pre-sleep processing executing unit that executes processing relating to before sleep, and a sleeping processing executing unit that executes processing relating to during sleep.

(17)

The information processing apparatus according to (16), in which the pre-sleep processing executing unit performs at least one of a suggestion about an action before the sleep or control of a sleep environment as the processing relating to before the sleep, and the sleeping processing executing unit performs at least one of measurement of a sleep state, control of the sleep environment, or adjustment of a wake-up timing as the processing relating to during the sleep.

(18)

An information processing method including the processes of:

measuring a stress level of a user on the basis of a result of detection by a sensor; and specifying a factor causing an increase or decrease in the stress level on the basis of an action of the user in a period in which the stress level is increased or decreased.

(19)

A program causing a computer to serve as:

a stress level measuring unit that measures a stress level of a user on the basis of a result of detection by a sensor; and a stress factor specifying unit that specifies a factor causing an increase or decrease in the stress level on the basis of an action of the user in a period in which the stress level is increased or decreased.

REFERENCE SIGNS LIST

1: portable terminal
2: server
3: output device
4: network
10: stress control system
11: input unit
12: interface
13: processing unit
14: interface
15: output unit
31: action analyzer
32: stress level measuring unit
33: database
34: stress factor specifying unit
35: stress increase/decrease threshold value specifying unit
36: stress level increase/decrease processing unit
311: target value setting unit
312: scheduled time determining unit
313: pre-sleep action controller
314: sleeping controller
401, 411, 421: information processing apparatus

The invention claimed is:

1. An information processing apparatus, comprising:
a processor configured to:
measure a stress level of a user based on a result of detection by a sensor;
specify a factor causing an increase in the stress level, based on a first action of the user in a period in which the stress level is decreased; and
execute, based on the stress level that is lower than a threshold value, a first event corresponding to the factor that causes the increase in the stress level.

2. The information processing apparatus according to claim 1, wherein the processor is further configured to specify the factor based on an environment of the user in the period in which the stress level is decreased.

3. The information processing apparatus according to claim 1, wherein the processor is further configured to:
execute a second event corresponding to a factor having caused a decrease in the stress level based on the stress level higher than the threshold value.

4. The information processing apparatus according to claim 1, wherein the processor is further configured to execute, as the first event, a process that causes the user to take at least one of a second action corresponding to the factor or a suggestion about the second action corresponding to the factor.

5. The information processing apparatus according to claim 4, wherein the processor is further configured to control output of the suggestion about the second action corresponding to the factor with use of voice or AR display.

6. The information processing apparatus according to claim 1, wherein
the processor is further configured to control analysis of a third action of the user based on the result of detection by the sensor, and
the first event is executed corresponding to the third action of the user.

7. The information processing apparatus according to claim 1, wherein the processor is further configured to output information representing the increase in the stress level together with information representing the factor.

8. The information processing apparatus according to claim 7, wherein the processor is further configured to output information representing the factor that is discrete or information representing the factor that is continuous.

9. The information processing apparatus according to claim 8, wherein the processor is further configured to output information representing a fourth action of the user in each time zone as the information representing the factor that is discrete and information representing a change in the result of detection by the sensor as the information representing the factor that is continuous.

10. The information processing apparatus according to claim 7, wherein the processor is further configured to output the information representing the increase in the stress level together with a moving route of the user with use of a location of the user as the factor.

11. The information processing apparatus according to claim 7, wherein the processor is further configured to output information representing the stress level to a position on a map corresponding to a position where the stress level has been measured with use of a location of the user as the factor.

12. The information processing apparatus according to claim 7, wherein the processor is further configured to output information representing the stress level measured in each period with use of a specific period as the factor.

13. The information processing apparatus according to claim 7, wherein the processor is further configured to output information representing the stress level together with information representing a companion of the user with use of the companion of the user as the factor.

14. The information processing apparatus according to claim 1, wherein the processor is further configured to:
  set a target value of sleep quality based on the decrease in the stress level, and
  determine a scheduled bedtime and a scheduled wake-up time based on the target value.

15. The information processing apparatus according to claim 14, wherein the processor is further configured to:
  execute a process before sleep, and
  execute a process at a time of the sleep.

16. The information processing apparatus according to claim 15, wherein the processor is further configured to:
  perform at least one of a suggestion about a fifth action before the sleep or control of a sleep environment as the process before the sleep, and
  perform at least one of measurement of a sleep state, control of the sleep environment, or adjustment of a wake-up timing as the process at the time of the sleep.

17. An information processing, method comprising:
  measuring a stress level of a user based on a result of detection by a sensor;
  specifying a factor causing an increase in the stress level, based on an action of the user in a period in which the stress level is decreased; and
  executing, based on the stress level that is lower than a threshold value, an event corresponding to the factor that causes the increase in the stress level.

18. A non-transitory computer-readable medium having stored thereon, computer-executable instructions which, when executed by a processor, cause the processor to execute operations, the operations comprising:
  measuring a stress level of a user based on a result of detection by a sensor;
  specifying a factor causing an increase in the stress level, based on an action of the user in a period in which the stress level is decreased; and
  executing, based on the stress level that is lower than a threshold value, an event corresponding to the factor that causes the increase in the stress level.

* * * * *